(12) United States Patent
Chen et al.

(10) Patent No.: US 9,353,089 B2
(45) Date of Patent: May 31, 2016

(54) COMPOSITIONS AND METHODS FOR THE TREATMENT OF MALARIA

(71) Applicants: Saint Louis University, St. Louis, MO (US); Guangzhou Institutes of Biomedicine and Health, Chinese Academy of Sciences, Guangzhou (CN)

(72) Inventors: Xiaoping Chen, Guangzhou (CN); Ke Ding, Guangzhou (CN); Marvin J. Meyers, Wentzville, MO (US); Micky D. Tortorella, Guangzhou (CN); Jing Xu, Guangzhou (CN)

(73) Assignees: Saint Louis University, St. Louis, MO (US); Guangzhou Institutes of Biomedicine and Health, Chinese Academy of Sciences, Guangzhou (CN)

( * ) Notice: Subject to any disclaimer, the term of this patent is extended or adjusted under 35 U.S.C. 154(b) by 3 days.

(21) Appl. No.: 14/226,295

(22) Filed: Mar. 26, 2014

(65) Prior Publication Data
US 2014/0296532 A1   Oct. 2, 2014

Related U.S. Application Data

(60) Provisional application No. 61/805,208, filed on Mar. 26, 2013.

(51) Int. Cl.
| | | |
|---|---|---|
| C07D 405/14 | (2006.01) |
| C07D 233/02 | (2006.01) |
| C07D 401/10 | (2006.01) |
| C07D 403/04 | (2006.01) |

(52) U.S. Cl.
CPC ............ *C07D 405/14* (2013.01); *C07D 233/02* (2013.01); *C07D 401/10* (2013.01); *C07D 403/04* (2013.01)

(58) Field of Classification Search
CPC .. C07D 401/04; C07D 401/06; C07D 233/88; C07D 405/14
USPC .............................. 546/210, 274.4; 548/321.5
See application file for complete search history.

(56) References Cited

U.S. PATENT DOCUMENTS

| | | |
|---|---|---|
| 2007/0027199 A1 | 2/2007 | Malamas et al. |
| 2008/0200445 A1* | 8/2008 | Zhu et al. ................. 514/210.02 |
| 2008/0287460 A1 | 11/2008 | Burrows et al. |
| 2009/0291946 A1 | 11/2009 | Yao et al. |

FOREIGN PATENT DOCUMENTS

| | | |
|---|---|---|
| WO | WO 2007/058602 | 5/2007 |
| WO | WO 2008/103351 | 8/2008 |
| WO | WO 2010/105179 | 9/2010 |

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003).*
Barré et al., "Equilibrium dialysis, ultrafiltration, and ultracentrifugation compared for determining the plasma-protein-binding characteristics of valproic acid", Clin Chem., 31(1):60-4, 1985.
Calderón et al., "An Invitation to Open Innovation in Malaria Drug Discovery: 47 Quality Starting Points from the TCAMS", *ACS Medicinal Chemistry Letters*, 2(10):741-746, 2011.
Cumming et al., "Structure based design of iminohydantoin BACE1 inhibitors: identification of an orally available, centrally active BACE1 inhibitor", *Bioorganic & Medicinal Chemistry Letters*, 22:2444-2449, 2012.
Malamas et al., "Design and synthesis of 5,5'-disubstituted aminohydantoins as potent and selective human beta-secretase (BACE1) inhibitors", *Journal of Medicinal Chemistry*, 53:1146-1158, 2010.
Malamas et al., "Di-substituted pyridinyl aminohydantoins as potent and highly selective human beta-secretase (BACE1) inhibitors", *Bioorganic & Medicinal Chemistry*, 18:630-639, 2010.
Malamas et al., "New pyrazolyl and thienyl aminohydantoins as potent BACE1 inhibitors: exploring the S2' region", *Bioorganic & Medicinal Chemistry Letters*, 21:5164-5170, 2011.
Meyers et al., "Evaluation of Aminohydantoins as a Novel Class of Antimalarial Agents", *ACS Medicinal Chemistry Letters*, 5(1):89-93, 2014.
Peters, "Editorial: New antimalarial agents", J Trop Med Hyg., 78(8):167-70, 1975.
Smilkstein et al., "Simple and inexpensive fluorescence-based technique for high-throughput antimalarial drug screening", *Antimicrob. Agents Chemother.*, 48:1803-1806, 2004.
Winter et al., "Evaluation and lead optimization of anti-malarial acridones", *Exp. Parasitol.*, 114:47-56, 2006.
Zhou et al., "Pyridinyl aminohydantoins as small molecule BACE1 inhibitors", *Bioorganic & Medicinal Chemistry Letters*, 20:2326-2329, 2010.

* cited by examiner

*Primary Examiner* — David K O Dell
(74) *Attorney, Agent, or Firm* — Parker Highlander PLLC

(57) ABSTRACT

The present invention provides aminohydantoin anti-malarial agents. In some embodiments, these agents have the property of functions of targeting malarial aspartic proteases while at the same time having low activity against human BACE. Methods of employing such agents are also provided.

8 Claims, 2 Drawing Sheets

COMPOSITIONS AND METHODS FOR THE TREATMENT OF MALARIA

This application claims the benefit of U.S. Provisional Patent Application No. 61/805,208, filed on Mar. 26, 2013, the entirety of which is incorporated herein by reference.

This invention was made with government support under Grant No. R01AI106498 awarded by the National Institutes of Health. The government has certain rights in the invention.

BACKGROUND OF THE INVENTION

I. Field of the Invention

The present invention relates to the fields of medicine, pharmacology and infectious disease. More particular, the invention relates to methods and compositions for treating malarial infections.

II. Related Art

Malaria is a devastating mosquito-borne infectious disease caused by a parasite of the genus *Plasmodium*, placing over one billion people at high risk for infection. According to the World Health Organization, there were 225 million cases of malaria in 2009 with 781,000 deaths. Although there are a number of drugs used to treat the disease, resistance to most of these drugs is widespread. As a consequence, there is an urgent push for developing antimalarial therapies targeting novel modes of action. Despite this urgent need, most antimalarial drugs in late stage clinical development do not target new mechanisms of action. Rather, these efforts have been focused on enhancing existing antimalarials such as artemisinin. Recently, scientists at GlaxoSmithKline and elsewhere have published on the antimalarial activity of thousands of compounds (Calderon et al., 2011).

*Plasmodium* has multiple aspartic proteases, including Plasmepsin V (PM-V), which has been demonstrated to be essential to the parasite's survival due to its role in the export of hundreds of *Plasmodium* proteins to the host erythrocyte. Most early drug discovery efforts in this area have focused on inhibition of the plasmepsins of the digestive vacuole (PM-I, II, IV and III or HAP), but these efforts have not been very successful due to the redundancy of their function. The function of the other plasmepsins (PM-VI, VII, VIII, IX, X) is unknown. It is likely that inhibition of one or more of the plasmepsins, particularly PMs V-X, would be lethal to the parasite. However, there are currently few tools available to identify inhibitors of PMs V-X and no high throughput assays. The only known inhibitors of PM-V are pepstatin A and HIV protease inhibitors such as lopinavir and ritonavir. These inhibitors are weak inhibitors of PM-V ($IC_{50}$>20 μM) and, due to their large molecular weights and peptidomimetic character, make poor starting points for drug discovery.

SUMMARY OF THE INVENTION

In one aspect, the invention provides compounds of the formula I:

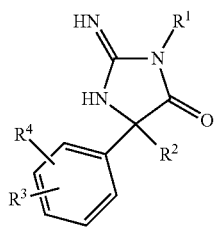

Formula I wherein:
$R^1$ is cycloalkyl$_{(C3-7)}$, heterocycloalkyl$_{(C3-10)}$, or a substituted version of any of these groups, or

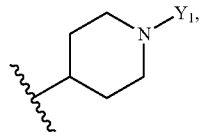

wherein $Y_1$ is aralkyl$_{(C7-12)}$, acyl$_{(C1-8)}$ or a substituted version of any of these groups;

$R^2$ is aryl$_{(C6-10)}$, -arenediyl$_{(C6-10)}$-alkoxy$_{(C1-7)}$, -arenediyl$_{(C6-10)}$-heteroaryl$_{(C1-5)}$, heteroaryl$_{(C1-5)}$, alkyl$_{(C2-7)}$, cycloalkyl$_{(C3-7)}$, —CH$_2$-cycloalkyl$_{(C3-7)}$, cycloalkoxyl$_{(C3-7)}$, or a substituted version of any of these groups;

$R^3$ is:
hydroxy, halo, —C(O)NH$_2$, —C(O)NHCH$_3$, —C(O)N(CH$_3$)$_2$, or —CN; or
alkyl$_{(C1-7)}$, haloalkyl$_{(C1-7)}$, alkoxy$_{(C1-7)}$, haloalkoxy$_{(C1-7)}$, aryl$_{(C6-10)}$, —O-aryl$_{(C6-10)}$, heteroaryl$_{(C1-9)}$, —O-heteroaryl$_{(C1-9)}$, —O—CH$_2$-aryl$_{(C6-10)}$, -arenediyl$_{(C6-C10)}$, -alkynyl$_{(C2-6)}$, substituted -arenediyl$_{(C6-C10)}$-alkynyl$_{(C2-6)}$, -heteroarenediyl$_{(C6-C10)}$-alkynyl$_{(C2-6)}$, substituted -heteroarenediyl$_{(C6-C10)}$-alkynyl$_{(C2-6)}$, —O—CH$_2$-heteroaryl$_{(C1-9)}$, substituted aryl$_{(C6-10)}$, substituted —O-aryl$_{(C6-10)}$, substituted heteroaryl$_{(C1-9)}$, substituted —O-heteroaryl$_{(C1-9)}$, substituted —O—CH$_2$-aryl$_{(C6-10)}$, or substituted —O—CH$_2$-heteroaryl$_{(C1-9)}$; and $R^4$ is:
H, halo, hydroxy, or —CN; or
alkyl$_{(C1-7)}$, halo alkyl$_{(C1-7)}$, alkoxy$_{(C1-7)}$, or halo alkoxy$_{(C1-7)}$,
provided that when $R^2$ is cyclopropyl, $R^3$ is not 3-chlorophenyl;
or pharmaceutically acceptable salts thereof.

In one embodiment, $R^1$ may be cycloalkyl$_{(C3-7)}$, for example, cyclopropyl, cyclobutyl, cyclopentyl, cyclohexyl, or cycloheptyl. In another embodiment, $R^1$ may be heterocycloalkyl$_{(C3-7)}$ or substituted heterocycloalkyl$_{(C3-7)}$, for example, tetrahydropyranyl, piperidin-4-yl, 1-methylpiperidin-4-yl, N-Boc-piperidin-4-yl, 1-benzylpiperidin-4-yl, 1-acetylpiperidin-4-yl, 1-benzoylpiperidin-4-yl, or 1-[3-(dimethylamino)propanoyl]-piperidin-4-yl.

In one embodiment, $R^2$ may be aryl$_{(C6-10)}$ or substituted aryl$_{(C6-10)}$, for example, phenyl, 4-methoxyphenyl, 3-methoxyphenyl, 4-bromophenyl, 4-chlorophenyl, 4-methylphenyl, 4-ethoxyphenyl, 3,4-dimethoxyphenyl, 4-trifluoromethoxyphenyl, 2-chlorophenyl, 3-methylphenyl, or 3-chlorophenyl. In another embodiment, $R^2$ may be -arenediyl$_{(C6-10)}$-alkoxy$_{(C1-7)}$, for example, 3-(2-methylpropoxy) phenyl or 4-(2-methylpropoxy)phenyl. In yet another embodiment, $R^2$ may be -arenediyl$_{(C6-10)}$-heteroaryl$_{(C1-5)}$, for example, (3-pyridin-3-yl)phenyl. In yet another embodiment, $R^2$ may be heteroaryl$_{(C1-5)}$ or substituted heteroaryl$_{(C1-5)}$, for example, pyridin-3-yl, pyridin-2-yl, pyrimidin-5-yl, pyridin-4-yl, or 1-methyl-1H-pyrazol-4-yl. In yet another embodiment, $R^2$ may be cycloalkyl$_{(C3-7)}$, for example, cyclopropyl, cyclopentyl, or cyclohexyl.

In one embodiment, $R^3$ may be alkyl$_{(C1-7)}$, for example, methyl. In another embodiment, $R^3$ may be alkoxy$_{(C1-7)}$, for example, methoxy, ethoxy or 2-methylpropoxy. In yet another embodiment, $R^3$ may be haloalkoxy$_{(C1-7)}$, for example, trifluoromethoxy. In yet another embodiment, $R^3$ may be aryl$_{(C6-10)}$ or substituted aryl$_{(C6-10)}$, for example, phenyl, 3-methoxyphenyl or 3-cyanophenyl. In yet another embodiment, $R^3$ may be —O-aryl$_{(C6-10)}$, for example, —O-phenyl. In yet another embodiment, $R^3$ may be heteroaryl$_{(C1-9)}$, for example, pyridin-2-yl, pyridin-3-yl, or pyridin-4-yl. In yet another embodiment, $R^3$ may be —O—CH$_2$-aryl$_{(C6-10)}$, for example, —O—CH$_2$-phenyl.

Examples of specific compounds provided by the embodiments of Formula I include:

3-cyclohexyl-2-imino-5,5-bis(4-methoxyphenyl)imidazolidin-4-one;
3-cyclohexyl-2-imino-5,5-bis(3-methoxyphenyl)imidazolidin-4-one;
3-cyclohexyl-2-imino-5-phenyl-5-[3-(pyridin-3-yl)phenyl]imidazolidin-4-one;
3-cyclohexyl-2-imino-5-(4-methoxyphenyl)-5-phenylimidazolidin-4-one;
3-cyclohexyl-2-imino-5-(3-methoxyphenyl)-5-phenylimidazolidin-4-one;
5,5-bis(4-bromophenyl)-3-cyclohexyl-2-iminoimidazolidin-4-one;
5,5-bis(4-chlorophenyl)-3-cyclohexyl-2-iminoimidazolidin-4-one;
3-cyclohexyl-2-imino-5,5-bis(4-methylphenyl)imidazolidin-4-one;
3-cyclohexyl-5,5-bis(4-ethoxyphenyl)-2-iminoimidazolidin-4-one;
3-cyclopropyl-2-imino-5,5-bis(4-methoxyphenyl)imidazolidin-4-one;
3-cyclopentyl-2-imino-5,5-bis(4-methoxyphenyl)imidazolidin-4-one;
2-imino-5,5-bis(4-methoxyphenyl)-3-(1-methylpiperidin-4-yl)imidazolidin-4-one;
3-cyclopropyl-2-imino-5,5-bis(3-methoxyphenyl)imidazolidin-4-one;
3-cyclopentyl-2-imino-5,5-bis(3-methoxyphenyl)imidazolidin-4-one;
3-cyclohexyl-2-imino-5-(4-methoxyphenyl)-5-[3-(pyridin-3-yl)phenyl]-imidazolidin-4-one;
3-cyclohexyl-2-imino-5-(4-methoxyphenyl)-5-[3-(pyridin-4-yl)phenyl]-imidazolidin-4-one;
3-cyclohexyl-5,5-bis(3,4-dimethoxyphenyl)-2-iminoimidazolidin-4-one;
2-imino-5,5-bis(4-methoxyphenyl)-3-(oxan-4-yl)imidazolidin-4-one;
3-cyclohexyl-2-imino-5-(4-methoxyphenyl)-5-(3-phenylphenyl)imidazolidin-4-one;
3-cyclohexyl-2-imino-5,5-bis[4-(trifluoromethoxy)phenyl]imidazolidin-4-one;
5,5-bis(2-chlorophenyl)-3-cyclohexyl-2-iminoimidazolidin-4-one;
3-cyclobutyl-2-imino-5,5-bis(4-methoxyphenyl)imidazolidin-4-one;
tert-butyl 4-[2-imino-4,4-bis(4-methoxyphenyl)-5-oxoimidazolidin-1-yl]-piperidine-1-carboxylate;
2-imino-5,5-bis(4-methoxyphenyl)-3-(piperidin-4-yl)imidazolidin-4-one;
3-cyclohexyl-2-imino-5-(4-methoxyphenyl)-5-[3-(pyridin-2-yl)phenyl]-imidazolidin-4-one;
3-cyclohexyl-2-imino-5-phenyl-5-[3-(pyridin-4-yl)phenyl]imidazolidin-4-one;
3-cyclohexyl-2-imino-5-phenyl-5-(3-phenylphenyl)imidazolidin-4-one;
3-cyclohexyl-2-imino-5-(3-methoxyphenyl)-5-[3-(pyridin-3-yl)phenyl]-imidazolidin-4-one;
3-cycloheptyl-2-imino-5,5-bis(4-methoxyphenyl)imidazolidin-4-one;
3-cyclohexyl-2-imino-5-(3-methoxyphenyl)-5-[3-(pyridin-4-yl)phenyl]-imidazolidin-4-one;
3-cyclohexyl-2-imino-5-(3-methoxyphenyl)-5-[3-(pyridin-2-yl)phenyl]-imidazolidin-4-one;
5-[3-(benzyloxy)phenyl]-3-cyclohexyl-2-imino-5-phenylimidazolidin-4-one;
5-[3-(benzyloxy)phenyl]-3-cyclohexyl-2-imino-5-(3-methoxyphenyl)-imidazolidin-4-one;
3-cyclohexyl-2-imino-5,5-bis(3-methylphenyl)imidazolidin-4-one;
3-cyclohexyl-2-imino-5-(3-phenoxyphenyl)-5-phenylimidazolidin-4-one;
3-(1-benzylpiperidin-4-yl)-2-imino-5,5-bis(4-methoxyphenyl)imidazolidin-4-one;
5,5-bis(3-chlorophenyl)-3-cyclohexyl-2-iminoimidazolidin-4-one;
3-cyclohexyl-2-imino-5,5-bis[3-(pyridin-3-yl)phenyl]imidazolidin-4-one;
3-(1-cyclohexyl-2-imino-5-oxo-4-phenylimidazolidin-4-yl)-N-methylbenz amide;
3-(1-acetylpiperidin-4-yl)-2-imino-5,5-bis(4-methoxyphenyl)imidazolidin-4-one;
3-(1-benzoylpiperidin-4-yl)-2-imino-5,5-bis(4-methoxyphenyl)imidazolidin-4-one;
3-{1-[3-(dimethylamino)propanoyl]piperidin-4-yl}-2-imino-5,5-bis(4-methoxy-phenyl)imidazolidin-4-one;
2-imino-5-(4-methoxyphenyl)-3-(oxan-4-yl)-5-(pyridin-3-yl)imidazolidin-4-one;
2-imino-5-[3-(3-methoxyphenyl)phenyl]-3-(oxan-4-yl)-5-phenylimidazolidin-4-one;
5-cyclopropyl-2-imino-5-(4-methoxyphenyl)-3-(oxan-4-yl)imidazolidin-4-one;
3-cyclohexyl-2-imino-5-[3-(3-methoxyphenyl)phenyl]-5-phenylimidazolidin-4-one;
3-cyclohexyl-5-cyclopropyl-2-imino-5-[3-(3-methoxyphenyl)phenyl]-imidazolidin-4-one;
5-cyclopropyl-2-imino-5-[3-(3-methoxyphenyl)phenyl]-3-(oxan-4-yl)-imidazolidin-4-one;
5-cyclohexyl-2-imino-5-(4-methoxyphenyl)-3-(oxan-4-yl)imidazolidin-4-one;
2-imino-5-(4-methoxyphenyl)-3-(oxan-4-yl)-5-(pyridin-2-yl)imidazolidin-4-one;
2-imino-5-(4-methoxyphenyl)-3-(oxan-4-yl)-5-(pyrimidin-5-yl)imidazolidin-4-one;
2-imino-5-(4-methoxyphenyl)-3-(oxan-4-yl)-5-(pyridin-4-yl)imidazolidin-4-one;
5-cyclopentyl-2-imino-5-(4-methoxyphenyl)-3-(oxan-4-yl)imidazolidin-4-one;
2-imino-5-(4-methoxyphenyl)-5-(1-methyl-1H-pyrazol-4-yl)-3-(oxan-4-yl)-imidazolidin-4-one;
2-imino-5,5-bis[3-(2-methylpropoxy)phenyl]-3-(oxan-4-yl)imidazolidin-4-one;
2-imino-5,5-bis[4-(2-methylpropoxy)phenyl]-3-(oxan-4-yl)imidazolidin-4-one;
2-imino-5,5-bis(4-methoxyphenyl)-3-(4-methylcyclohexyl)imidazolidin-4-one;
2-imino-5-(3-isobutoxyphenyl)-5-(3-(pyridin-3-yl)phenyl)-3-(tetrahydro-2H-pyran-4-yl)imidazolidin-4-one;
2-imino-5-(4-isobutoxyphenyl)-5-(3-(pyridin-3-yl)phenyl)-3-(tetrahydro-2H-pyran-4-yl)imidazolidin-4-one;
3'-(2-imino-5-oxo-4-phenyl-1-(tetrahydro-2H-pyran-4-yl)imidazolidin-4-yl)-[1,1'-biphenyl]-3-carbonitrile;
3'-(4-cyclopropyl-2-imino-5-oxo-1-(tetrahydro-2H-pyran-4-yl)imidazolidin-4-yl)-[1,1'-biphenyl]-3-carbonitrile;

3,5-dicyclohexyl-2-imino-5-(4-methoxyphenyl)imidazolidin-4-one;
3'-(1-cyclohexyl-4-cyclopropyl-2-imino-5-oxoimidazolidin-4-yl)-[1,1'-biphenyl]-3-carbonitrile;
5-cyclopropyl-2-imino-5-(3-(pyridin-3-yl)phenyl)-3-(tetrahydro-2H-pyran-4-yl)-imidazolidin-4-one;
5-(3-(4-cyclopropyl-2-imino-5-oxo-1-(tetrahydro-2H-pyran-4-yl)imidazolidin-4-yl)phenyl)nicotinonitrile;
5-(3-(5-chloropyridin-3-yl)phenyl)-5-cyclopropyl-2-imino-3-(tetrahydro-2H-pyran-4-yl)imidazolidin-4-one;
5-cyclopropyl-2-imino-5-(4-methoxy-3-(pyridin-3-yl)phenyl)-3-(tetrahydro-2H-pyran-4-yl)imidazolidin-4-one;
5'-(4-cyclopropyl-2-imino-5-oxo-1-(tetrahydro-2H-pyran-4-yl)imidazolidin-4-yl)-2'-methoxy-[1,1'-biphenyl]-3-carbonitrile;
3'-(4-cyclohexyl-2-imino-5-oxo-1-(tetrahydro-2H-pyran-4-yl)imidazolidin-4-yl)-[1,1'-biphenyl]-3-carbonitrile;
3-cyclohexyl-5-cyclopentyl-2-imino-5-(4-methoxyphenyl)imidazolidin-4-one;
5-cyclopropyl-2-imino-3-(tetrahydro-2H-pyran-4-yl)-5-(4-(trifluoromethoxy)-phenyl)imidazolidin-4-one;
5-(3-chlorophenyl)-5-cyclopropyl-2-imino-3-(tetrahydro-2H-pyran-4-yl)-imidazolidin-4-one;
5-(4-chlorophenyl)-5-cyclopropyl-2-imino-3-(tetrahydro-2H-pyran-4-yl)-imidazolidin-4-one;
5-cyclopropyl-5-(3'-ethynyl-[1,1'-biphenyl]-3-yl)-2-imino-3-(tetrahydro-2H-pyran-4-yl)imidazolidin-4-one;
5-cyclopropyl-5-(3,4-difluorophenyl)-2-imino-3-(tetrahydro-2H-pyran-4-yl)-imidazolidin-4-one;
5-cyclopropyl-2-imino-5-(3-methoxyphenyl)-3-(tetrahydro-2H-pyran-4-yl)-imidazolidin-4-one;
5-(2-chlorophenyl)-5-cyclopropyl-2-imino-3-(tetrahydro-2H-pyran-4-yl)-imidazolidin-4-one;
5-(4-chloro-3-methoxyphenyl)-5-cyclohexyl-2-imino-3-(tetrahydro-2H-pyran-4-yl)imidazolidin-4-one;
3-cyclohexyl-5-cyclopropyl-2-imino-5-(3-(pyridin-3-yl)phenyl)imidazolidin-4-one;
5-(3-(1-cyclohexyl-4-cyclopropyl-2-imino-5-oxoimidazolidin-4-yl)phenyl)-nicotinonitrile;
5-(3-(5-chloropyridin-3-yl)phenyl)-3-cyclohexyl-5-cyclopropyl-2-iminoimidazolidin-4-one;
3-cyclohexyl-5-cyclopropyl-2-imino-5-(3-(5-(prop-1-yn-1-yl)pyridin-3-yl)-phenyl)imidazolidin-4-one;
5-(3-(5-chloropyridin-3-yl)phenyl)-5-cyclohexyl-2-imino-3-(tetrahydro-2H-pyran-4-yl)imidazolidin-4-one;
5-cyclohexyl-2-imino-5-(3-(pyridin-3-yl)phenyl)-3-(tetrahydro-2H-pyran-4-yl)-imidazolidin-4-one;
5-cyclopropyl-2-imino-5-(2-methoxyphenyl)-3-(tetrahydro-2H-pyran-4-yl)-imidazolidin-4-one;
5-cyclopropyl-5-(3-hydroxyphenyl)-2-imino-3-(tetrahydro-2H-pyran-4-yl)-imidazolidin-4-one;
3-cyclohexyl-5,5-bis(4-hydroxyphenyl)-2-iminoimidazolidin-4-one;
5-cyclopropyl-2-imino-5-(4-(pyridin-3-yl)phenyl)-3-(tetrahydro-2H-pyran-4-yl)-imidazolidin-4-one;
3-cyclohexyl-5-cyclopropyl-5-(3-hydroxyphenyl)-2-iminoimidazolidin-4-one;
5,5-bis(4-hydroxyphenyl)-2-imino-3-(tetrahydro-2H-pyran-4-yl)imidazolidin-4-one;
3-cyclohexyl-5-cyclopropyl-5-(4-hydroxyphenyl)-2-iminoimidazolidin-4-one;
5-(4'-chloro-[1,1'-biphenyl]-3-yl)-5-cyclopropyl-2-imino-3-(tetrahydro-2H-pyran-4-yl)imidazolidin-4-one;
4-((4-(1-cyclohexyl-4-cyclopropyl-2-imino-5-oxoimidazolidin-4-yl)phenoxy)-methyl)benzonitrile;
3-cyclohexyl-5-cyclopropyl-2-imino-5-(2-methoxyphenyl)imidazolidin-4-one;
5-cyclopropyl-5-(2-hydroxyphenyl)-2-imino-3-(tetrahydro-2H-pyran-4-yl)-imidazolidin-4-one;
4-((3-(1-cyclohexyl-4-cyclopropyl-2-imino-5-oxoimidazolidin-4-yl)phenoxy)-methyl)benzonitrile;
4-((3-(1-cyclohexyl-4-cyclopropyl-2-imino-5-oxoimidazolidin-4-yl)phenoxy)-methyl)benzamide;
3-cyclohexyl-5-cyclopropyl-2-imino-5-(3-phenoxyphenyl)imidazolidin-4-one;
5-cyclopropyl-5-(3,4-dichlorophenyl)-2-imino-3-(tetrahydro-2H-pyran-4-yl)-imidazolidin-4-one;
3-cyclohexyl-5-cyclopropyl-5-(2-hydroxyphenyl)-2-iminoimidazolidin-4-one;
5-(4-chlorophenyl)-5-cyclohexyl-2-imino-3-(tetrahydro-2H-pyran-4-yl)-imidazolidin-4-one;
5-(4-chlorophenyl)-3,5-dicyclohexyl-2-iminoimidazolidin-4-one;
5-(4-chlorophenyl)-3-cyclohexyl-5-cyclopropyl-2-iminoimidazolidin-4-one;
3-(1-(5-chloro-2-hydroxybenzyl)piperidin-4-yl)-2-imino-5,5-bis(4-methoxyphenyl)imidazolidin-4-one; and
3-(1-(2-hydroxybenzyl)piperidin-4-yl)-2-imino-5,5-bis(4-methoxyphenyl)-imidazolidin-4-one;
or a pharmaceutically acceptable salt thereof.

Examples of preferred compounds provided by the embodiments of Formula I include:
3-cyclohexyl-2-imino-5,5-bis(4-methoxyphenyl)imidazolidin-4-one;
2-imino-5,5-bis(4-methoxyphenyl)-3-(oxan-4-yl)imidazolidin-4-one;
5-cyclohexyl-2-imino-5-(4-methoxyphenyl)-3-(oxan-4-yl)imidazolidin-4-one; and
5-cyclopentyl-2-imino-5-(4-methoxyphenyl)-3-(oxan-4-yl)imidazolidin-4-one;
or a pharmaceutically acceptable salt thereof In one aspect, the invention provides compounds of the formula:

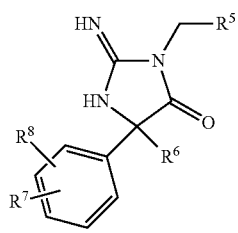

Formula II wherein:
R$^5$ is cycloalkyl$_{(C3-7)}$, heterocycloalkyl$_{(C3-10)}$, or substituted versions of any of these groups, or

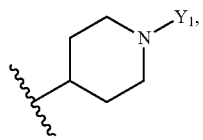

wherein: Y$_1$ is aralkyl$_{(C7-12)}$, acyl$_{(C1-8)}$ or a substituted version of any of these groups;
R$^6$ is aryl$_{(C6-10)}$, heteroaryl$_{(C1-5)}$, cycloalkyl$_{(C3-7)}$, —CH$_2$-cycloalkyl$_{(C3-7)}$, cycloalkoxy$_{(C3-7)}$, or substituted versions of any of these groups;

R⁷ is:
  hydroxy, halo, —C(O)NH₂, —C(O)NHCH₃, —C(O)N(CH₃)₂, or —CN; or
  alkyl$_{(C1-7)}$, halo alkyl$_{(C1-7)}$, alkoxy$_{(C1-7)}$, halo alkoxy$_{(C1-7)}$, aryl$_{(C6-10)}$, —O-aryl$_{(C6-10)}$, heteroaryl$_{(C1-9)}$, —O-heteroaryl$_{(C1-9)}$, —O—CH₂-aryl$_{(C6-10)}$, —O—CH₂-heteroaryl$_{(C1-9)}$, -arenediyl$_{(C6-C10)}$-alkynyl$_{(C2-6)}$, substituted -arenediyl$_{(C6-C10)}$-alkynyl$_{(C2-6)}$, -heteroarenediyl$_{(C6-C10)}$-alkynyl$_{(C2-6)}$, substituted -heteroarenediyl$_{(C2-C10)}$-alkynyl$_{(C2-6)}$, substituted aryl$_{(C6-10)}$, substituted —O-aryl$_{(C6-10)}$, substituted heteroaryl$_{(C1-9)}$, substituted —O-heteroaryl$_{(C1-9)}$, substituted —O—CH₂-aryl$_{(C6-10)}$, or substituted —O—CH₂-heteroaryl$_{(C1-9)}$; and R⁸ is:
  H, halo, hydroxy, or CN; or
  alkyl$_{(C1-7)}$, haloalkyl$_{(C1-7)}$, alkoxy$_{(C1-7)}$, or haloalkoxy$_{(C1-7)}$;
  provided that when R⁶ is cyclopropyl, R⁷ is not 3-chlorophenyl;
or a pharmaceutically acceptable salt thereof.

In one embodiment, R⁵ may be cycloalkyl$_{(C3-7)}$, for example, cyclohexyl. In other embodiment, R⁵ may be heterocycloalkyl$_{(C3-7)}$ or substituted heterocycloalkyl$_{(C3-7)}$, for example, tetrahydrofuryl, tetrahydropyranyl, piperidin-4-yl, 1-methylpiperidin-4-yl, or N-Boc-piperidin-4-yl.

In one embodiment, R⁶ may be aryl$_{(C6-10)}$ or substituted aryl$_{(C6-10)}$, for example, 4-methoxyphenyl.

In one embodiment, R⁷ may be alkoxy$_{(C1-7)}$, for example, methoxy.

Examples of specific compounds provided by the embodiments of Formula II include:
3-(cyclohexylmethyl)-2-imino-5,5-bis(4-methoxyphenyl)imidazolidin-4-one;
2-imino-5,5-bis(4-methoxyphenyl)-3-(oxolan-2-ylmethyl)imidazolidin-4-one;
2-imino-5,5-bis(4-methoxyphenyl)-3-(oxan-4-ylmethyl)imidazolidin-4-one;
2-imino-5,5-bis(4-methoxyphenyl)-3-[(1-methylpiperidin-4-yl)methyl]-imidazolidin-4-one; and
tert-butyl 4-{[2-imino-4,4-bis(4-methoxyphenyl)-5-oxoimidazolidin-1-yl]-methyl}piperidine-1-carboxylate;
or a pharmaceutically acceptable salt thereof.

In one aspect, the present invention provides compounds of the formula:

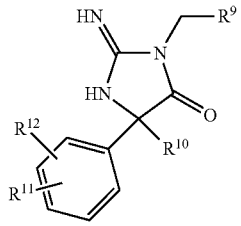

Formula III wherein:
  R⁹ is t-butyl, adamantanyl, aryl$_{(C6-10)}$, heteroaryl$_{(C1-6)}$ or substituted versions of any of these groups;
  R¹⁰ is phenyl, 2-methoxyphenyl, 3-methoxyphenyl, 4-methoxyphenyl, cyclobutyl, cyclopentyl, cyclohexyl or substituted versions of any of these groups;

R¹¹ is:
  hydroxy, methoxy, methyl, trifluoromethyl, trifluoromethoxy, halo, or —CN; or
  aryl$_{(C6-10)}$, heteroaryl$_{(C1-9)}$, substituted aryl$_{(C6-10)}$, or substituted heteroaryl$_{(C1-9)}$; and
R¹ is H, halo, hydroxy, or —CN;
or a pharmaceutically acceptable salt thereof.

In one embodiment, R⁹ may be heteroaryl$_{(C1-5)}$ or substituted heteroaryl$_{(C6-10)}$, for example, pyridyl or picolinyl. In one embodiment, R¹⁰ may be 4-methoxyphenyl or 3-methoxyphenyl. In one embodiment, R¹¹ may be 4-methoxy or 3-methoxy.

Examples of specific compounds provided by the embodiments of Formula III include:
3-benzyl-2-imino-5,5-bis(3-methoxyphenyl)imidazolidin-4-one;
3-benzyl-2-imino-5,5-bis(4-methoxyphenyl)imidazolidin-4-one;
2-imino-5,5-bis(4-methoxyphenyl)-3-(pyridin-4-ylmethyl)imidazolidin-4-one;
2-imino-5,5-bis(4-methoxyphenyl)-3-(pyridin-3-ylmethyl)imidazolidin-4-one;
2-imino-5,5-bis(4-methoxyphenyl)-3-(naphthalen-1-ylmethyl)imidazolidin-4-one;
2-imino-5,5-bis(4-methoxyphenyl)-3-(pyridin-2-ylmethyl)imidazolidin-4-one;
2-imino-5,5-bis(4-methoxyphenyl)-3-[(4-methylphenyl)methyl]imidazolidin-4-one;
3-[(4-chlorophenyl)methyl]-2-imino-5,5-bis(4-methoxyphenyl)imidazolidin-4-one;
2-imino-5,5-bis(4-methoxyphenyl)-3-[(4-methoxyphenyl)methyl]imidazolidin-4-one;
3-[(2-chlorophenyl)methyl]-2-imino-5,5-bis(4-methoxyphenyl)imidazolidin-4-one;
3-[(3-chlorophenyl)methyl]-2-imino-5,5-bis(4-methoxyphenyl)imidazolidin-4-one;
2-imino-5,5-bis(4-methoxyphenyl)-3-[(3-methoxyphenyl)methyl]imidazolidin-4-one;
2-imino-5,5-bis(4-methoxyphenyl)-3-[(2-methoxyphenyl)methyl]imidazolidin-4-one;
2-imino-5,5-bis(4-methoxyphenyl)-3-{[3-(trifluoromethyl)phenyl]methyl}-imidazolidin-4-one;
3-(2,2-dimethylpropyl)-2-imino-5,5-bis(4-methoxyphenyl)imidazolidin-4-one;
2-imino-5,5-bis(4-methoxyphenyl)-3-[(3-methylphenyl)methyl]imidazolidin-4-one;
3-[(2,5-dimethylphenyl)methyl]-2-imino-5,5-bis(4-methoxyphenyl)imidazolidin-4-one;
3-(adamantan-1-ylmethyl)-2-imino-5,5-bis(4-methoxyphenyl)imidazolidin-4-one;
3-[(2,3-dimethylphenyl)methyl]-2-imino-5,5-bis(4-methoxyphenyl)imidazolidin-4-one;
3-[(2,6-dimethylphenyl)methyl]-2-imino-5,5-bis(4-methoxyphenyl)imidazolidin-4-one;
2-imino-5,5-bis(4-methoxyphenyl)-3-[(3-methylpyridin-2-yl)methyl]imidazolidin-4-one;
2-imino-5,5-bis(4-methoxyphenyl)-3-[(2-methylphenyl)methyl]imidazolidin-4-one;
2-imino-5,5-bis(4-methoxyphenyl)-3-{[2-(trifluoromethyl)phenyl]methyl}-imidazolidin-4-one;
2-{[2-imino-4,4-bis(4-methoxyphenyl)-5-oxoimidazolidin-1-yl]methyl}-benzonitrile;
3-[(2-fluorophenyl)methyl]-2-imino-5,5-bis(4-methoxyphenyl)imidazolidin-4-one; and
3-[(2-bromophenyl)methyl]-2-imino-5,5-b is (4-methoxyphenyl)imidazolidin-4-one;
or a pharmaceutically acceptable salt thereof In some embodiments, compounds of the present disclosure are in the form of pharmaceutically acceptable salts. In other embodiments, compounds of the present disclosure are not in the form of a pharmaceutically acceptable salt.

Other general aspects of the present disclosure contemplate a pharmaceutical composition comprising as a therapeutically effective amount of a compound of the present disclosure and a pharmaceutically acceptable carrier. In certain embodiments, the pharmaceutical composition may further comprise a therapeutically effective amount of one or more compounds selected from the group consisting of other antimalarial compounds including quinine, chloroquine, amodiaquine, proguanil, cycloquanil, sulfadoxine, primaquine, pyrimethamine, chlorproquanil, tetracycline, dapsone, doxycycline, clindamycin, mefloquine, halofantrine, bulaquine, artemisinin, artemether, arteether, atovaquone, lumefantrine, dihydroartemisinin, piperaquine, artesunate, pyronaridine, azithromycin, tafenoquine, trimethoprim, sulfamethoxazole, artemisone, ferroquine, fosmidomycin, tinidazole, naphthoquine, methylene blue, (+)-erythromefloquine, tert-butyl isoquine, trioxaquine, an endoperoxide, a dihydrofolate reductase inhibitor, and a dihydroorotate dehydrogenase inhibitor.

In one embodiment, the pharmaceutical composition may be present in a fixed dosage form, for example, a tablet, a capsule, or a lyophilized powder.

Another general aspect of the present disclosure contemplates a therapeutic method for treating malaria comprising administering a therapeutically effective compound of the present disclosure to a subject. The subject may, for example, be a human. The subject may also by a non-human mammal. The compound may be administered orally, subcutaneously, intravenously, intra-arterially, or intramuscularly. The treatment may take place over a period of time exceeding 1 week, for example 2 weeks, 3 weeks, 4 weeks, one month, two months, three months, 6 months, 9 months or 12 months. The method of treatment may produce a reduction in parasitic load in the subject.

In certain embodiments, the therapeutic method comprises administering a second anti-malarial treatment, such as quinine, chloroquine, amodiaquine, proguanil, cycloquanil, sulfadoxine, primaquine, pyrimethamine, chlorproquanil, tetracycline, dapsone, doxycycline, clindamycin, mefloquine, halofantrine, bulaquine, artemisinin, artemether, arteether, atovaquone, lumefantrine, dihydroartemisinin, piperaquine, artesunate, pyronaridine, azithromycin, tafenoquine, trimethoprim, sulfamethoxazole, artemisone, ferroquine, fosmidomycin, tinidazole, naphthoquine, methylene blue, (+)-erythromefloquine, tert-butyl isoquine, trioxaquine, an endoperoxide, a dihydrofolate reductase inhibitor, or a dihydroorotate dehydrogenase inhibitor.

Yet another general aspect of the present invention contemplates a prophylactic method for preventing malaria comprising administering a prophylactically effective amount of a compound of the present disclosure to a subject.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
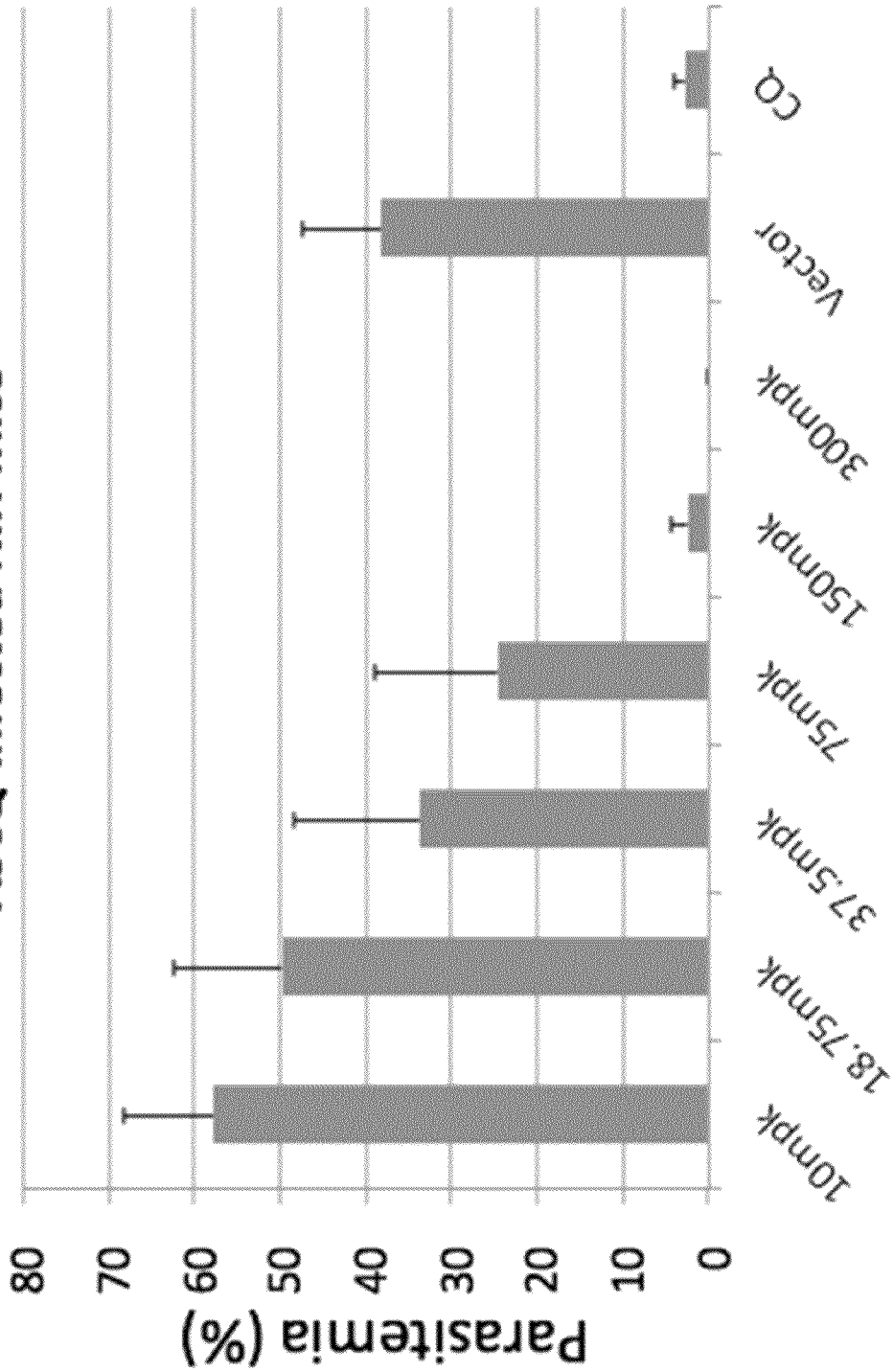
FIG. 1—Antimalarial Activity of 117 in Mice. This figure shows a 117 dose response assay in *P. chabaudi* ASCQ-infected NIH mice.

The present disclosure provides compounds which are useful for the treatment of malaria and other diseases caused by *Plasmodium* parasites. In some embodiments, the present invention provides compound which can be used to inhibit one of the multiple aspartic proteases found in *Plasmodium*. In some embodiments, an aspartic protease is inhibited by the compounds of the present invention selected from PM-I through PM-X. Furthermore, in some embodiments, more than one of the aspartic proteases PM-I through PM-X is inhibited by the compound. In some embodiments, inhibition of PM-I through PM-X results in a decreased parasitic load. In some embodiments, the compounds provided are used to treated malaria on their own or in combination with one or more other therapies. Furthermore, in some embodiments, the compounds can be administered to a patient as a prophylactic therapy.

I. Malaria

The mosquito genus *Anopheles* carries the malaria parasite (see *Plasmodium*). Worldwide, malaria is a leading cause of premature mortality, particularly in children under the age of five. It is widespread in tropical and subtropical regions, including parts of the Americas (22 countries), Asia, and Africa. Each year, there are approximately 350-500 million cases of malaria, killing between one and three million people, the majority of whom are young children in sub-Saharan Africa. Ninety percent of malaria-related deaths occur in sub-Saharan Africa. Malaria is commonly associated with poverty, and can indeed be a cause of poverty and a major hindrance to economic development.

Five species of the *plasmodium* parasite can infect humans; the most serious forms of the disease are caused by *Plasmodium falciparum*. Malaria caused by *Plasmodium vivax*, *Plasmodium ovale* and *Plasmodium malariae* causes milder disease in humans that is not generally fatal. A fifth species, *Plasmodium knowlesi*, is a zoonosis that causes malaria in macaques but can also infect humans.

Malaria is naturally transmitted by the bite of a female *Anopheles* mosquito. When a mosquito bites an infected person, a small amount of blood is taken, which contains malaria parasites. These develop within the mosquito, and about one week later, when the mosquito takes its next blood meal, the parasites are injected with the mosquito's saliva into the person being bitten. After a period of between two weeks and several months (occasionally years) spent in the liver, the malaria parasites start to multiply within red blood cells, causing symptoms that include fever, and headache. In severe cases the disease worsens leading to hallucinations, coma, and death.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travelers to malaria-endemic countries (prophylaxis). Resistance has developed to several antimalarial drugs, most notably chloroquine.

Malaria transmission can be reduced by preventing mosquito bites by distribution of inexpensive mosquito nets and insect repellents, or by mosquito-control measures such as spraying insecticides inside houses and draining standing water where mosquitoes lay their eggs. Although many are under development, the challenge of producing a widely available vaccine that provides a high level of protection for a sustained period is still to be met.

II. Active Agents and Intermediates

A. Compounds of the Present Invention

In one aspect, the invention provides compounds of the formula I:

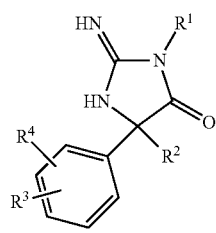

Formula I wherein:

$R^1$ is cycloalkyl$_{(C3-7)}$, heterocycloalkyl$_{(C3-10)}$, or a substituted version of any of these groups, or

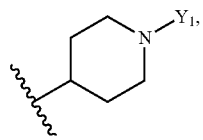

wherein $Y_1$ is aralkyl$_{(C7-12)}$, acyl$_{(C1-8)}$ or a substituted version of any of these groups;

$R^2$ is aryl$_{(C6-10)}$, -arenediyl$_{(C6-10)}$-alkoxy$_{(C1-7)}$, -arenediyl$_{(C6-10)}$-heteroaryl$_{(C1-5)}$, heteroaryl$_{(C1-5)}$, alkyl$_{(C2-7)}$, cycloalkyl$_{(C3-7)}$, —CH$_2$-cycloalkyl$_{(C3-7)}$, cycloalkoxyl$_{(C3-7)}$, or a substituted version of any of these groups;

$R^3$ is:

hydroxy, halo, —C(O)NH$_2$, —C(O)NHCH$_3$, —C(O)N(CH$_3$)$_2$, or —CN; or alkyl$_{(C1-7)}$, haloalkyl$_{(C1-7)}$, alkoxy$_{(C1-7)}$, haloalkoxy$_{(C1-7)}$, aryl$_{(C6-10)}$, —O-aryl$_{(C6-10)}$, heteroaryl$_{(C1-9)}$, —O-heteroaryl$_{(C1-9)}$, —O—CH$_2$-aryl$_{(C6-10)}$, —O—CH$_2$-heteroaryl$_{(C1-9)}$, -arenediyl$_{(C6-C10)}$, -alkynyl$_{(C2-6)}$, substituted -arenediyl$_{(C6-C10)}$, -alkynyl$_{(C2-6)}$, -heteroarenediyl$_{(C6-C10)}$-alkynyl$_{(C2-6)}$, substituted -heteroarenediyl$_{(C6-C10)}$-alkynyl$_{(C2-6)}$, substituted aryl$_{(C6-10)}$, substituted —O-aryl$_{(C6-10)}$, substituted heteroaryl$_{(C1-9)}$, substituted —O-heteroaryl$_{(C1-9)}$, substituted —O—CH$_2$-aryl$_{(C6-10)}$, or substituted —O—CH$_2$-heteroaryl$_{(C1-9)}$; and $R^4$ is:

H, halo, hydroxy, or —CN; or alkyl$_{(C1-7)}$, halo alkyl$_{(C1-7)}$, alkoxy$_{(C1-7)}$, or halo alkoxy$_{(C1-7)}$, provided that when $R^2$ is cyclopropyl, $R^3$ is not 3-chlorophenyl;

or pharmaceutically acceptable salts thereof.

In one embodiment, $R^1$ may be cycloalkyl$_{(C3-7)}$, for example, cyclopropyl, cyclobutyl, cyclopentyl, cyclohexyl, or cycloheptyl. In another embodiment, $R^1$ may be heterocycloalkyl$_{(C3-7)}$ or substituted heterocycloalkyl$_{(C3-7)}$, for example, tetrahydropyranyl, piperidin-4-yl, 1-methylpiperidin-4-yl, N-Boc-piperidin-4-yl, 1-benzylpiperidin-4-yl, 1-acetylpiperidin-4-yl, 1-benzoylpiperidin-4-yl, or 1-[3-(dimethylamino)propanoyl]piperidin-4-yl.

In one embodiment, $R^2$ may be aryl$_{(C6-10)}$ or substituted aryl$_{(C6-10)}$, for example, phenyl, 4-methoxyphenyl, 3-methoxyphenyl, 4-bromophenyl, 4-chlorophenyl, 4-methylphenyl, 4-ethoxyphenyl, 3,4-dimethoxyphenyl, 4-trifluoromethoxyphenyl, 2-chlorophenyl, 3-methylphenyl, or 3-chlorophenyl. In another embodiment, $R^2$ may be -arenediyl$_{(C6-10)}$-alkoxy$_{(C1-7)}$, for example, 3-(2-methylpropoxy)phenyl or 4-(2-methylpropoxy)phenyl. In yet another embodiment, $R^2$ may be -arenediyl$_{(C6-10)}$-heteroaryl$_{(C1-5)}$, for example, (3-pyridin-3-yl)phenyl. In yet another embodiment, $R^2$ may be heteroaryl$_{(C1-5)}$ or substituted heteroaryl$_{(C1-5)}$, for example, pyridin-3-yl, pyridin-2-yl, pyrimidin-5-yl, pyridin-4-yl, or 1-methyl-1H-pyrazol-4-yl. In yet another embodiment, $R^2$ may be cycloalkyl$_{(C3-7)}$, for example, cyclopropyl, cyclopentyl, or cyclohexyl.

In one embodiment, $R^3$ may be alkyl$_{(C1-7)}$, for example, methyl. In another embodiment, $R^3$ may be alkoxy$_{(C1-7)}$, for example, methoxy, ethoxy or 2-methylpropoxy. In yet another embodiment, $R^3$ may be haloalkoxy$_{(C1-7)}$, for example, trifluoromethoxy. In yet another embodiment, $R^3$ may be aryl$_{(C6-10)}$ or substituted aryl$_{(C6-10)}$, for example, phenyl, 3-methoxyphenyl or 3-cyanophenyl. In yet another embodiment, $R^3$ may be —O-aryl$_{(C6-10)}$, for example, —O-phenyl. In yet another embodiment, $R^3$ may be heteroaryl$_{(C1-9)}$, for example, pyridin-2-yl, pyridin-3-yl, or pyridin-4-yl. In yet another embodiment, $R^3$ may be —O—CH$_2$-aryl$_{(C6-10)}$, for example, —O—CH$_2$-phenyl.

Examples of specific compounds provided by the embodiments of Formula I include:

3-cyclohexyl-2-imino-5,5-bis(4-methoxyphenyl)imidazolidin-4-one;

3-cyclohexyl-2-imino-5,5-bis(3-methoxyphenyl)imidazolidin-4-one;

3-cyclohexyl-2-imino-5-phenyl-5-[3-(pyridin-3-yl)phenyl]imidazolidin-4-one;

3-cyclohexyl-2-imino-5-(4-methoxyphenyl)-5-phenylimidazolidin-4-one;

3-cyclohexyl-2-imino-5-(3-methoxyphenyl)-5-phenylimidazolidin-4-one;
5,5-bis(4-bromophenyl)-3-cyclohexyl-2-iminoimidazolidin-4-one;
5,5-bis(4-chlorophenyl)-3-cyclohexyl-2-iminoimidazolidin-4-one;
3-cyclohexyl-2-imino-5,5-bis(4-methylphenyl)imidazolidin-4-one;
3-cyclohexyl-5,5-bis(4-ethoxyphenyl)-2-iminoimidazolidin-4-one;
3-cyclopropyl-2-imino-5,5-bis(4-methoxyphenyl)imidazolidin-4-one;
3-cyclopentyl-2-imino-5,5-bis(4-methoxyphenyl)imidazolidin-4-one;
2-imino-5,5-bis(4-methoxyphenyl)-3-(1-methylpiperidin-4-yl)imidazolidin-4-one;
3-cyclopropyl-2-imino-5,5-bis(3-methoxyphenyl)imidazolidin-4-one;
3-cyclopentyl-2-imino-5,5-bis(3-methoxyphenyl)imidazolidin-4-one;
3-cyclohexyl-2-imino-5-(4-methoxyphenyl)-5-[3-(pyridin-3-yl)phenyl]-imidazolidin-4-one;
3-cyclohexyl-2-imino-5-(4-methoxyphenyl)-5-[3-(pyridin-4-yl)phenyl]-imidazolidin-4-one;
3-cyclohexyl-5,5-bis(3,4-dimethoxyphenyl)-2-iminoimidazolidin-4-one;
2-imino-5,5-bis(4-methoxyphenyl)-3-(oxan-4-yl)imidazolidin-4-one;
3-cyclohexyl-2-imino-5-(4-methoxyphenyl)-5-(3-phenylphenyl)imidazolidin-4-one;
3-cyclohexyl-2-imino-5,5-bis[4-(trifluoromethoxy)phenyl]imidazolidin-4-one;
5,5-bis(2-chlorophenyl)-3-cyclohexyl-2-iminoimidazolidin-4-one;
3-cyclobutyl-2-imino-5,5-bis(4-methoxyphenyl)imidazolidin-4-one;
tert-butyl 4-[2-imino-4,4-bis(4-methoxyphenyl)-5-oxoimidazolidin-1-yl]-piperidine-1-carboxylate;
2-imino-5,5-bis(4-methoxyphenyl)-3-(piperidin-4-yl)imidazolidin-4-one;
3-cyclohexyl-2-imino-5-(4-methoxyphenyl)-5-[3-(pyridin-2-yl)phenyl]-imidazolidin-4-one;
3-cyclohexyl-2-imino-5-phenyl-5-[3-(pyridin-4-yl)phenyl]imidazolidin-4-one;
3-cyclohexyl-2-imino-5-phenyl-5-(3-phenylphenyl)imidazolidin-4-one;
3-cyclohexyl-2-imino-5-(3-methoxyphenyl)-5-[3-(pyridin-3-yl)phenyl]-imidazolidin-4-one;
3-cycloheptyl-2-imino-5,5-bis(4-methoxyphenyl)imidazolidin-4-one;
3-cyclohexyl-2-imino-5-(3-methoxyphenyl)-5-[3-(pyridin-4-yl)phenyl]-imidazolidin-4-one;
3-cyclohexyl-2-imino-5-(3-methoxyphenyl)-5-[3-(pyridin-2-yl)phenyl]-imidazolidin-4-one;
5-[3-(benzyloxy)phenyl]-3-cyclohexyl-2-imino-5-phenylimidazolidin-4-one;
5-[3-(benzyloxy)phenyl]-3-cyclohexyl-2-imino-5-(3-methoxyphenyl)-imidazolidin-4-one;
3-cyclohexyl-2-imino-5,5-bis(3-methylphenyl)imidazolidin-4-one;
3-cyclohexyl-2-imino-5-(3-phenoxyphenyl)-5-phenylimidazolidin-4-one;
3-(1-benzylpiperidin-4-yl)-2-imino-5,5-bis(4-methoxyphenyl)imidazolidin-4-one;
5,5-bis(3-chlorophenyl)-3-cyclohexyl-2-iminoimidazolidin-4-one;
3-cyclohexyl-2-imino-5,5-bis[3-(pyridin-3-yl)phenyl]imidazolidin-4-one;
3-(1-cyclohexyl-2-imino-5-oxo-4-phenylimidazolidin-4-yl)-N-methylbenzamide;
3-(1-acetylpiperidin-4-yl)-2-imino-5,5-bis(4-methoxyphenyl)imidazolidin-4-one;
3-(1-benzoylpiperidin-4-yl)-2-imino-5,5-bis(4-methoxyphenyl)imidazolidin-4-one;
3-{1-[3-(dimethylamino)propanoyl]piperidin-4-yl}-2-imino-5,5-bis(4-methoxyphenyl)imidazolidin-4-one;
2-imino-5-(4-methoxyphenyl)-3-(oxan-4-yl)-5-(pyridin-3-yl)imidazolidin-4-one;
2-imino-5-[3-(3-methoxyphenyl)phenyl]-3-(oxan-4-yl)-5-phenylimidazolidin-4-one;
5-cyclopropyl-2-imino-5-(4-methoxyphenyl)-3-(oxan-4-yl)imidazolidin-4-one;
3-cyclohexyl-2-imino-5-[3-(3-methoxyphenyl)phenyl]-5-phenylimidazolidin-4-one;
3-cyclohexyl-5-cyclopropyl-2-imino-5-[3-(3-methoxyphenyl)phenyl]-imidazolidin-4-one;
5-cyclopropyl-2-imino-5-[3-(3-methoxyphenyl)phenyl]-3-(oxan-4-yl)-imidazolidin-4-one;
5-cyclohexyl-2-imino-5-(4-methoxyphenyl)-3-(oxan-4-yl)imidazolidin-4-one;
2-imino-5-(4-methoxyphenyl)-3-(oxan-4-yl)-5-(pyridin-2-yl)imidazolidin-4-one;
2-imino-5-(4-methoxyphenyl)-3-(oxan-4-yl)-5-(pyrimidin-5-yl)imidazolidin-4-one;
2-imino-5-(4-methoxyphenyl)-3-(oxan-4-yl)-5-(pyridin-4-yl)imidazolidin-4-one;
5-cyclopentyl-2-imino-5-(4-methoxyphenyl)-3-(oxan-4-yl)imidazolidin-4-one;
2-imino-5-(4-methoxyphenyl)-5-(1-methyl-1H-pyrazol-4-yl)-3-(oxan-4-yl)-imidazolidin-4-one;
2-imino-5,5-bis[3-(2-methylpropoxy)phenyl]-3-(oxan-4-yl)imidazolidin-4-one;
2-imino-5,5-bis[4-(2-methylpropoxy)phenyl]-3-(oxan-4-yl)imidazolidin-4-one;
2-imino-5,5-bis(4-methoxyphenyl)-3-(4-methylcyclohexyl)imidazolidin-4-one;
2-imino-5-(3-isobutoxyphenyl)-5-(3-(pyridin-3-yl)phenyl)-3-(tetrahydro-2H-pyran-4-yl)imidazolidin-4-one;
2-imino-5-(4-isobutoxyphenyl)-5-(3-(pyridin-3-yl)phenyl)-3-(tetrahydro-2H-pyran-4-yl)imidazolidin-4-one;
3'-(2-imino-5-oxo-4-phenyl-1-(tetrahydro-2H-pyran-4-yl)imidazolidin-4-yl)-[1,1'-biphenyl]-3-carbonitrile;
3'-(4-cyclopropyl-2-imino-5-oxo-1-(tetrahydro-2H-pyran-4-yl)imidazolidin-4-yl)-[1,1'-biphenyl]-3-carbonitrile;
3,5-dicyclohexyl-2-imino-5-(4-methoxyphenyl)imidazolidin-4-one;
3'-(1-cyclohexyl-4-cyclopropyl-2-imino-5-oxoimidazolidin-4-yl)-[1,1'-biphenyl]-3-carbonitrile;
5-cyclopropyl-2-imino-5-(3-(pyridin-3-yl)phenyl)-3-(tetrahydro-2H-pyran-4-yl)-imidazolidin-4-one;
5-(3-(4-cyclopropyl-2-imino-5-oxo-1-(tetrahydro-2H-pyran-4-yl)imidazolidin-4-yl)phenyl)nicotinonitrile;
5-(3-(5-chloropyridin-3-yl)phenyl)-5-cyclopropyl-2-imino-3-(tetrahydro-2H-pyran-4-yl)imidazolidin-4-one;
5-cyclopropyl-2-imino-5-(4-methoxy-3-(pyridin-3-yl)phenyl)-3-(tetrahydro-2H-pyran-4-yl)imidazolidin-4-one;
5'-(4-cyclopropyl-2-imino-5-oxo-1-(tetrahydro-2H-pyran-4-yl)imidazolidin-4-yl)-2'-methoxy-[1,1'-biphenyl]-3-carbonitrile;
3'-(4-cyclohexyl-2-imino-5-oxo-1-(tetrahydro-2H-pyran-4-yl)imidazolidin-4-yl)-[1,1'-biphenyl]-3-carbonitrile;
3-cyclohexyl-5-cyclopentyl-2-imino-5-(4-methoxyphenyl)imidazolidin-4-one;

5-cyclopropyl-2-imino-3-(tetrahydro-2H-pyran-4-yl)-5-(4-(trifluoromethoxy)-phenyl)imidazolidin-4-one;
5-(3-chlorophenyl)-5-cyclopropyl-2-imino-3-(tetrahydro-2H-pyran-4-yl)-imidazolidin-4-one;
5-(4-chlorophenyl)-5-cyclopropyl-2-imino-3-(tetrahydro-2H-pyran-4-yl)-imidazolidin-4-one;
5-cyclopropyl-5-(3'-ethynyl-[1,1'-biphenyl]-3-yl)-2-imino-3-(tetrahydro-2H-pyran-4-yl)imidazolidin-4-one;
5-cyclopropyl-5-(3,4-difluorophenyl)-2-imino-3-(tetrahydro-2H-pyran-4-yl)-imidazolidin-4-one;
5-cyclopropyl-2-imino-5-(3-methoxyphenyl)-3-(tetrahydro-2H-pyran-4-yl)-imidazolidin-4-one;
5-(2-chlorophenyl)-5-cyclopropyl-2-imino-3-(tetrahydro-2H-pyran-4-yl)-imidazolidin-4-one;
5-(4-chloro-3-methoxyphenyl)-5-cyclohexyl-2-imino-3-(tetrahydro-2H-pyran-4-yl)imidazolidin-4-one;
3-cyclohexyl-5-cyclopropyl-2-imino-5-(3-(pyridin-3-yl)phenyl)imidazolidin-4-one;
5-(3-(1-cyclohexyl-4-cyclopropyl-2-imino-5-oxoimidazolidin-4-yl)phenyl)-nicotinonitrile;
5-(3-(5-chloropyridin-3-yl)phenyl)-3-cyclohexyl-5-cyclopropyl-2-iminoimidazolidin-4-one;
3-cyclohexyl-5-cyclopropyl-2-imino-5-(3-(5-(prop-1-yn-1-yl)pyridin-3-yl)-phenyl)imidazolidin-4-one;
5-(3-(5-chloropyridin-3-yl)phenyl)-5-cyclohexyl-2-imino-3-(tetrahydro-2H-pyran-4-yl)-imidazolidin-4-one;
5-cyclohexyl-2-imino-5-(3-(pyridin-3-yl)phenyl)-3-(tetrahydro-2H-pyran-4-yl)-imidazolidin-4-one;
5-cyclopropyl-2-imino-5-(2-methoxyphenyl)-3-(tetrahydro-2H-pyran-4-yl)-imidazolidin-4-one;
5-cyclopropyl-5-(3-hydroxyphenyl)-2-imino-3-(tetrahydro-2H-pyran-4-yl)-imidazolidin-4-one;
3-cyclohexyl-5,5-bis(4-hydroxyphenyl)-2-iminoimidazolidin-4-one;
5-cyclopropyl-2-imino-5-(4-(pyridin-3-yl)phenyl)-3-(tetrahydro-2H-pyran-4-yl)-imidazolidin-4-one;
3-cyclohexyl-5-cyclopropyl-5-(3-hydroxyphenyl)-2-iminoimidazolidin-4-one;
5,5-bis(4-hydroxyphenyl)-2-imino-3-(tetrahydro-2H-pyran-4-yl)imidazolidin-4-one;
3-cyclohexyl-5-cyclopropyl-5-(4-hydroxyphenyl)-2-iminoimidazolidin-4-one;
5-(4'-chloro-[1,1'-biphenyl]-3-yl)-5-cyclopropyl-2-imino-3-(tetrahydro-2H-pyran-4-yl)imidazolidin-4-one;
4-((4-(1-cyclohexyl-4-cyclopropyl-2-imino-5-oxoimidazolidin-4-yl)phenoxy)-methyl)benzonitrile;
3-cyclohexyl-5-cyclopropyl-2-imino-5-(2-methoxyphenyl)imidazolidin-4-one;
5-cyclopropyl-5-(2-hydroxyphenyl)-2-imino-3-(tetrahydro-2H-pyran-4-yl)-imidazolidin-4-one;
4-((3-(1-cyclohexyl-4-cyclopropyl-2-imino-5-oxoimidazolidin-4-yl)phenoxy)-methyl)benzonitrile;
4-((3-(1-cyclohexyl-4-cyclopropyl-2-imino-5-oxoimidazolidin-4-yl)phenoxy)-methyl)benzamide;
3-cyclohexyl-5-cyclopropyl-2-imino-5-(3-phenoxyphenyl)imidazolidin-4-one;
5-cyclopropyl-5-(3,4-dichlorophenyl)-2-imino-3-(tetrahydro-2H-pyran-4-yl)-imidazolidin-4-one;
3-cyclohexyl-5-cyclopropyl-5-(2-hydroxyphenyl)-2-iminoimidazolidin-4-one;
5-(4-chlorophenyl)-5-cyclohexyl-2-imino-3-(tetrahydro-2H-pyran-4-yl)-imidazolidin-4-one;
5-(4-chlorophenyl)-3,5-dicyclohexyl-2-iminoimidazolidin-4-one;
5-(4-chlorophenyl)-3-cyclohexyl-5-cyclopropyl-2-iminoimidazolidin-4-one;
3-(1-(5-chloro-2-hydroxybenzyl)piperidin-4-yl)-2-imino-5,5-bis(4-methoxyphenyl)imidazolidin-4-one; and
3-(1-(2-hydroxybenzyl)piperidin-4-yl)-2-imino-5,5-bis(4-methoxyphenyl)-imidazolidin-4-one;
or a pharmaceutically acceptable salt thereof.

Examples of preferred compounds provided by the embodiments of Formula I include:
3-cyclohexyl-2-imino-5,5-bis(4-methoxyphenyl)imidazolidin-4-one;
2-imino-5,5-bis(4-methoxyphenyl)-3-(oxan-4-yl)imidazolidin-4-one;
5-cyclohexyl-2-imino-5-(4-methoxyphenyl)-3-(oxan-4-yl)imidazolidin-4-one; and
5-cyclopentyl-2-imino-5-(4-methoxyphenyl)-3-(oxan-4-yl)imidazolidin-4-one;
or a pharmaceutically acceptable salt thereof.

In one aspect, the invention provides compounds of the formula:

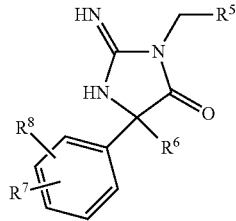

Formula II wherein:
R⁵ is cycloalkyl$_{(C3-7)}$, heterocycloalkyl$_{(C3-10)}$, or substituted versions of any of these groups, or

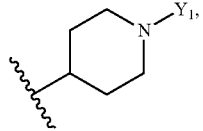

wherein Y₁ is aralkyl$_{(C7-12)}$, acyl$_{(C1-8)}$ or a substituted version of any of these groups;
R⁶ is aryl$_{(C6-10)}$, heteroaryl$_{(C1-5)}$, cycloalkyl$_{(C3-7)}$, —CH₂-cycloalkyl$_{(C3-7)}$, cycloalkoxyl$_{(C3-7)}$, or substituted versions of any of these groups;
R⁷ is:
hydroxy, halo, —C(O)NH₂, —C(O)NHCH₃, —C(O)N(CH₃)₂, or —CN; or
alkyl$_{(C1-7)}$, haloalkyl$_{(C1-7)}$, alkoxy$_{(C1-7)}$, haloalkoxy$_{(C1-7)}$, aryl$_{(C6-10)}$, —O-aryl$_{(C6-10)}$, heteroaryl$_{(C1-9)}$, —O-heteroaryl$_{(C1-9)}$, —O—CH₂-aryl$_{(C6-10)}$, —O—CH₂-heteroaryl$_{(C1-9)}$, -arenediyl$_{(C6-C10)}$-alkynyl$_{(C2-6)}$, substituted -arenediyl$_{(C6-C10)}$-alkynyl$_{(C2-6)}$, -heteroarenediyl$_{(C6-C10)}$-alkynyl$_{(C2-6)}$, substituted -heteroarenediyl$_{(C6-C10)}$-alkynyl$_{(C2-6)}$, substituted aryl$_{(C6-10)}$, substituted —O-aryl$_{(C6-10)}$, substituted heteroaryl$_{(C1-9)}$, substituted —O-heteroaryl$_{(C1-9)}$, substituted —O—CH₂-aryl$_{(C6-10)}$, or substituted —O—CH₂-heteroaryl$_{(C1-9)}$; and
R⁸ is:
H, halo, hydroxy, or CN; or
alkyl$_{(C1-7)}$, haloalkyl$_{(C1-7)}$, alkoxy$_{(C1-7)}$, or haloalkoxy$_{(C1-7)}$;

provided that when $R^6$ is cyclopropyl, $R^7$ is not 3-chlorophenyl;
or a pharmaceutically acceptable salt thereof In one embodiment, $R^5$ may be cycloalkyl$_{(C3-7)}$, for example, cyclohexyl. In other embodiment, $R^5$ may be heterocycloalkyl$_{(C3-7)}$ or substituted heterocycloalkyl$_{(C3-7)}$, for example, tetrahydrofuryl, tetrahydropyranyl, piperidin-4-yl, 1-methylpiperidin-4-yl, or N-Boc-piperidin-4-yl.

In one embodiment, $R^6$ may be aryl$_{(C6-10)}$ or substituted aryl$_{(C6-10)}$, for example, 4-methoxyphenyl.

In one embodiment, $R^7$ may be alkoxy$_{(C1-7)}$, for example, methoxy.

Examples of specific compounds provided by the embodiments of Formula II include:

3-(cyclohexylmethyl)-2-imino-5,5-bis(4-methoxyphenyl) imidazolidin-4-one;
2-imino-5,5-bis(4-methoxyphenyl)-3-(oxolan-2-ylmethyl) imidazolidin-4-one;
2-imino-5,5-bis(4-methoxyphenyl)-3-(oxan-4-ylmethyl) imidazolidin-4-one;
2-imino-5,5-bis(4-methoxyphenyl)-3-[(1-methylpiperidin-4-yl)methyl]-imidazolidin-4-one; and
tert-butyl 4-{[2-imino-4,4-bis(4-methoxyphenyl)-5-oxoimidazolidin-1-yl]-methyl}piperidine-1-carboxylate;
or a pharmaceutically acceptable salt thereof.

In one aspect, the present invention provides compounds of the formula:

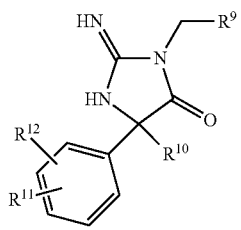

Formula III wherein:
$R^9$ is t-butyl, adamantanyl, aryl$_{(C6-10)}$, heteroaryl$_{(C1-6)}$ or substituted versions of any of these groups;
$R^{10}$ is phenyl, 2-methoxyphenyl, 3-methoxyphenyl, 4-methoxyphenyl, cyclobutyl, cyclopentyl, cyclohexyl or substituted versions of any of these groups;
$R^{11}$ is:
  hydroxy, methoxy, methyl, trifluoromethyl, trifluoromethoxy, halo, or —CN; or
  aryl$_{(C6-10)}$, heteroaryl$_{(C1-9)}$, substituted aryl$_{(C6-10)}$, or substituted heteroaryl$_{(C1-9)}$; and
$R^{12}$ is H, halo, hydroxy, or —CN;
or a pharmaceutically acceptable salt thereof In one embodiment, $R^9$ may be heteroaryl$_{(C1-5)}$ or substituted heteroaryl$_{(C6-10)}$, for example, pyridyl or picolinyl. In one embodiment, $R^{10}$ may be 4-methoxyphenyl or 3-methoxyphenyl. In one embodiment, $R^{11}$ may be 4-methoxy or 3-methoxy.

Examples of specific compounds provided by the embodiments of Formula III include:

3-benzyl-2-imino-5,5-bis(3-methoxyphenyl)imidazolidin-4-one;
3-benzyl-2-imino-5,5-bis(4-methoxyphenyl)imidazolidin-4-one;
2-imino-5,5-bis(4-methoxyphenyl)-3-(pyridin-4-ylmethyl) imidazolidin-4-one;
2-imino-5,5-bis(4-methoxyphenyl)-3-(pyridin-3-ylmethyl) imidazolidin-4-one;
2-imino-5,5-bis(4-methoxyphenyl)-3-(naphthalen-1-ylmethyl)imidazolidin-4-one;
2-imino-5,5-bis(4-methoxyphenyl)-3-(pyridin-2-ylmethyl) imidazolidin-4-one;
2-imino-5,5-bis(4-methoxyphenyl)-3-[(4-methylphenyl)methyl]imidazolidin-4-one;
3-[(4-chlorophenyl)methyl]-2-imino-5,5-bis(4-methoxyphenyl)imidazolidin-4-one;
2-imino-5,5-bis(4-methoxyphenyl)-3-[(4-methoxyphenyl) methyl]imidazolidin-4-one;
3-[(2-chlorophenyl)methyl]-2-imino-5,5-bis(4-methoxyphenyl)imidazolidin-4-one;
3-[(3-chlorophenyl)methyl]-2-imino-5,5-bis(4-methoxyphenyl)imidazolidin-4-one;
2-imino-5,5-bis(4-methoxyphenyl)-3-[(3-methoxyphenyl) methyl]imidazolidin-4-one;
2-imino-5,5-bis(4-methoxyphenyl)-3-[(2-methoxyphenyl) methyl]imidazolidin-4-one;
2-imino-5,5-bis(4-methoxyphenyl)-3-{[3-(trifluoromethyl) phenyl]methyl}-imidazolidin-4-one;
3-(2,2-dimethylpropyl)-2-imino-5,5-bis(4-methoxyphenyl) imidazolidin-4-one;
2-imino-5,5-bis(4-methoxyphenyl)-3-[(3-methylphenyl)methyl]imidazolidin-4-one;
3-[(2,5-dimethylphenyl)methyl]-2-imino-5,5-bis(4-methoxyphenyl)imidazolidin-4-one;
3-(adamantan-1-ylmethyl)-2-imino-5,5-bis(4-methoxyphenyl)imidazolidin-4-one;
3-[(2,3-dimethylphenyl)methyl]-2-imino-5,5-bis(4-methoxyphenyl)imidazolidin-4-one;
3-[(2,6-dimethylphenyl)methyl]-2-imino-5,5-bis(4-methoxyphenyl)imidazolidin-4-one;
2-imino-5,5-bis(4-methoxyphenyl)-3-[(3-methylpyridin-2-yl)methyl]-imidazolidin-4-one;
2-imino-5,5-bis(4-methoxyphenyl)-3-[(2-methylphenyl)methyl]imidazolidin-4-one;
2-imino-5,5-bis(4-methoxyphenyl)-3-{[2-(trifluoromethyl) phenyl]methyl}-imidazolidin-4-one;
2-{[2-imino-4,4-bis(4-methoxyphenyl)-5-oxoimidazolidin-1-yl]methyl}-benzonitrile;
3-[(2-fluorophenyl)methyl]-2-imino-5,5-bis(4-methoxyphenyl)imidazolidin-4-one; and
3-[(2-bromophenyl)methyl]-2-imino-5,5-bis(4-methoxyphenyl)imidazolidin-4-one;
or a pharmaceutically acceptable salt thereof.

In some embodiments, compounds of the present disclosure are in the form of pharmaceutically acceptable salts. In other embodiments, compounds of the present disclosure are not in the form of a pharmaceutically acceptable salt.

Other general aspects of the present disclosure contemplate a pharmaceutical composition comprising as a therapeutically effective amount of a compound of the present disclosure and a pharmaceutically acceptable carrier. In certain embodiments, the pharmaceutical composition may further comprise a therapeutically effective amount of one or more compounds selected from the group consisting of other antimalarial compounds including quinine, chloroquine, amodiaquine, proguanil, cycloquanil, sulfadoxine, primaquine, pyrimethamine, chlorproquanil, tetracycline, dapsone, doxycycline, clindamycin, mefloquine, halofantrine, bulaquine, artemisinin, artemether, arteether, atovaquone, lumefantrine, dihydroartemisinin, piperaquine, artesunate, pyronaridine, azithromycin, tafenoquine, trimethoprim, sulfamethoxazole, artemisone, ferroquine, fosmidomycin, tinidazole, naphthoquine, methylene blue, (+)-erythromefloquine, tert-butyl isoquine, trioxaquine, an endoperoxide, a dihydrofolate reductase inhibitor, and a dihydroorotate dehydrogenase inhibitor.

In one embodiment, the pharmaceutical composition may be present in a fixed dosage form, for example, a tablet, a capsule, or a lyophilized powder.

The compounds provided by the present disclosure are shown, for example, above in the summary of the invention section and in the claims below. They may be made using the methods outlined in the Synthesis and Examples sections below.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

B. Chemical Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol "⇌" represents a single bond or a double bond. Thus, for example, the structure

includes the structures

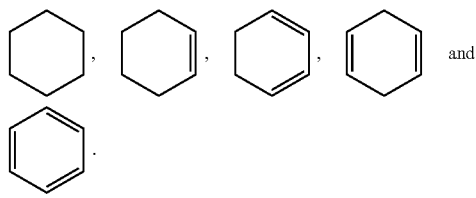

As will be understood by a person of skill in the art, no one such ring atom forms part of more than one double bond. The symbol " ⁓ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂" means a single bond where the group attached to the thick end of the wedge is "out of the page." The symbol "◁" means a single bond where the group attached to the thick end of the wedge is "into the page". The symbol " ⁓ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

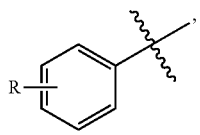

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

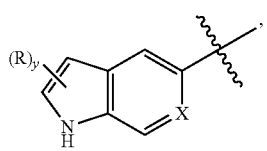

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "cycloalkyl" when used without the "substituted" modifier refers to a monovalent group with a carbon atom as the point of attachment, said carbon atom forming part of one or more aliphatic ring structures wherein the cycloalkyl group consists of no atoms other than carbon and hydrogen. As used herein, the term does not preclude the presence of one or more alkyl groups (carbon number limitation permitting) attached to the ring or ring system. If more than one ring is present, the rings may be fused or unfused. Non-limiting examples of cycloalkyl groups include —CH(CH$_2$)$_2$ (cyclopropyl), cyclobutyl, cyclopentyl, cyclohexyl, and cycloheptyl. When the term "cycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH$_3$) CH$_2$—, —CH═CHCH$_2$—, and

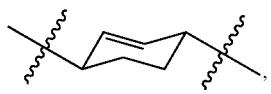 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH═CHF, —CH═CHCl and —CH═CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$, —OC(O)CH$_3$, or —S(O)$_2$ NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl) phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

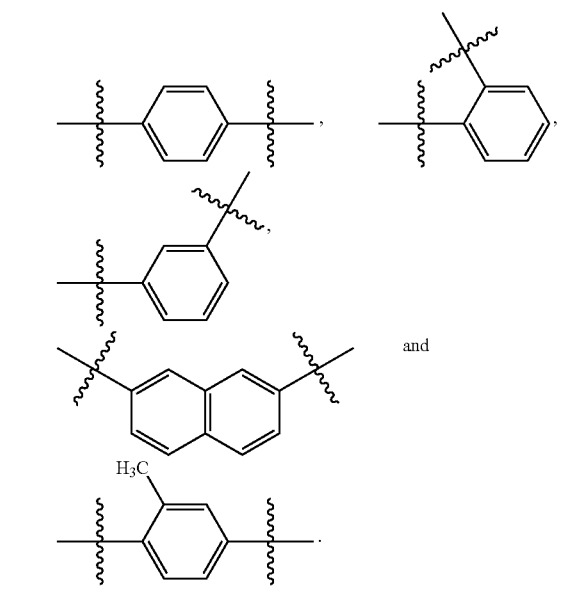

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$, —OC(O)CH$_3$, or —S(O)$_2$ NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted"

modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

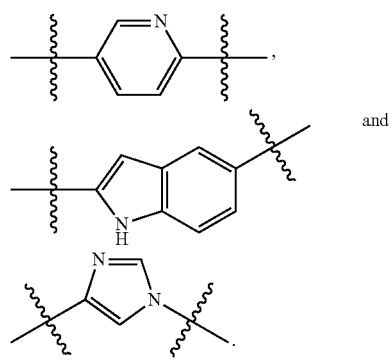

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, —S(O)₂NH₂, C(O)OC(CH₃)₃ (tert-butyloxycarbonyl, BOC), aralkyl, substituted aralkyl, acyl, or substituted acyl.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, C(O)CH(CH₃)₂, C(O)CH(CH₂)₂, C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylenebis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, ml is milliliter, mL is milliliter, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methyl pyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and Δ is heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

C. Synthetic Methods

The compounds provided by the present disclosure may be made using the methods outlined below and further described in the Examples section. General synthetic sequences for preparing the compounds useful in the present invention are outlined in Schemes I-VII. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention. Starting materials and equipment employed were either commercially available prepared by methods previously reported and readily duplicated by those skilled in the art.

The aminohydantoins of the present invention can be synthesized by the means described herein as well as by methods analogous to those described in the following references, which are incorporated by reference herein:

Meyers, et al., *ACS Medicinal Chemistry Letters*, 5(1):89-93, 2014

Cumming et al., *Bioorganic & Medicinal Chemistry Letters*, 22:2444-2449, 2012

Malamas et al., *Bioorganic & Medicinal Chemistry Letters*, 21:5164-5170, 2011

Malamas et al., *Bioorganic & Medicinal Chemistry*, 18:630-639, 2010

Malamas et al., *Journal of Medicinal Chemistry*, 53:1146-1158, 2010

Zhou et al., *Bioorganic & Medicinal Chemistry Letters*, 20:2326-2329, 2010

WO2007/058602

US2008/0287460

These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Scheme I

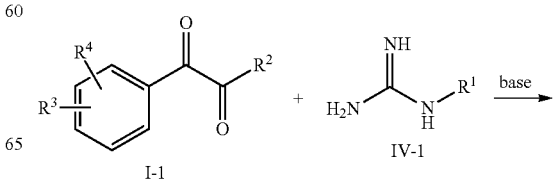

Scheme I illustrates methodology useful for preparing aminohydantoins of Formula I of the present invention. Briefly, in a method analogous to that described in WO2007/058602 and US2008/0287460, dione I-1 is condensed with a thiourea I-2 in a solvent such as DMSO and a strong base such as potassium hydroxide to give thiohydantoin I-3. A mixture of thiohydantoin I-3 in ammonium hydroxide and methanol is then treated with tert-butylperoxide to give aminohydantoins of Formula I.

Scheme II

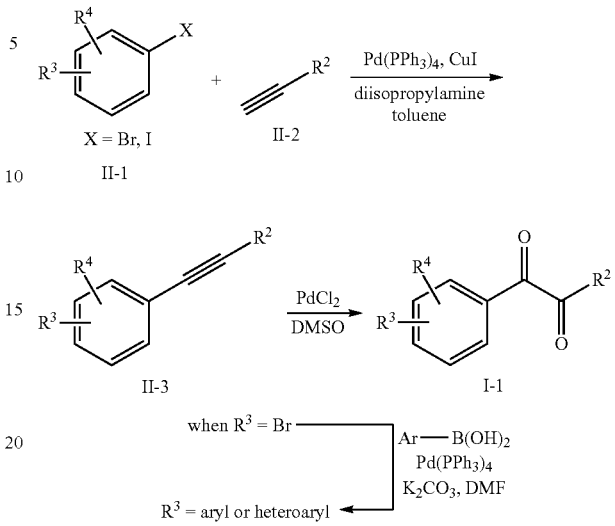

Scheme II illustrates methodology useful for preparing dione synthetic intermediates I-1. Briefly, an aryl halide is coupled to an alkyne II-2 wherein $R^2$ may be an aryl, heteroaryl, alkyl or cycloalkyl group under common Sonogashira coupling conditions using a catalyst such as tetrakis(triphenylphosphine)palladium, a base such as diisopropylamine or triethylamine and a solvent such as toluene or DMF. The Sonogashira yields an alkyne intermediate II-3 which may be oxidized to the dione I-1 in a solvent such as DMSO with a catalyst such as palladium chloride at elevated temperatures. Alkynes II-3 and diones I-1 wherein $R^3$ is aryl or heteroaryl may be prepared by treatment of either alkyne II-3 ($R^3$ = Br) or dione I-1 ($R^3$ = Br) with an aryl or heteroaryl boronic acid or ester under routine Suzuki coupling conditions with a palladium catalyst and base in a suitable solvent.

Scheme III

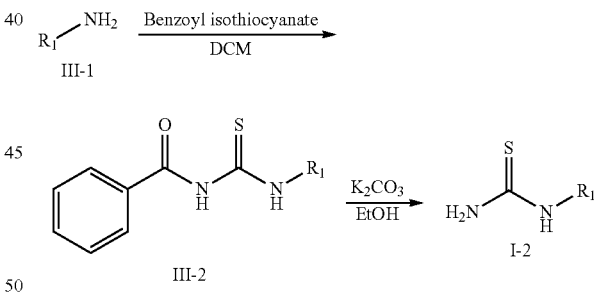

Scheme III illustrates methodology useful for preparing thiourea synthetic intermediates I-2. Briefly, an amine III-1 can be reacted with benzoyl isothiocyanate in a suitable solvent such as dichloromethane at 0° C. to room temperature to give benzoylthiourea intermediate III-2. Treatment with a base such as potassium carbonate in an alcohol such as ethanol at room temperature to refluxing conditions gives thiourea I-2.

Scheme IV

-continued

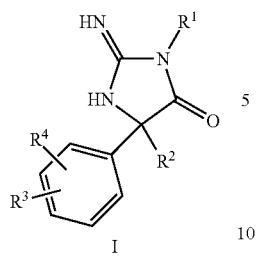

Scheme IV illustrates an alternative methodology useful for preparing aminohydantoins of Formula I of the present invention. An alkyl guanidine IV-1 may be condensed with dione I-1 in the presence of a base such as sodium carbonate, potassium carbonate, potassium hydroxide or triethylamine in a suitable solvent or combination of solvents such as DMSO, ethanol, water or dioxane to give aminohydantoins of Formula I. Similar procedures are described in Malamas et. al., *Bioorganic & Medicinal Chemistry Letters*, 21:5164-5170, 2011 and Cumming et al., *Bioorganic & Medicinal Chemistry Letters*, 22:2444-2449, 2012.

Scheme V

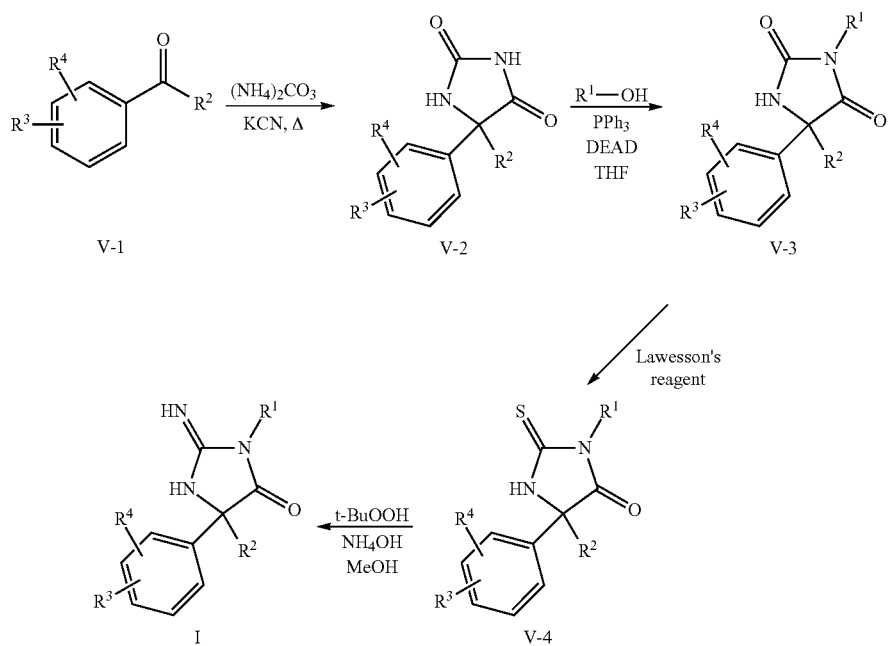

Scheme V illustrates methodology useful for preparing aminohydantoins of Formula I from aryl ketones such as V-1 where $R^2$ may be an aryl, heteroaryl, alkyl or cycloalkyl group. Aryl ketones can be readily purchased or prepared by well-established means (e.g., from an aryl acid chloride and a Grignard reagent). Aryl ketone V-1 may then be condensed with potassium cyanide and ammonium carbonate under Bucherer-Berg conditions to generate hydantoin V-2 (Cumming et al., *Bioorganic & Medicinal Chemistry Letters*, 22:244-2449, 2012). Hydantoin V-2 may be alkylated selectively at the more acidic N3 position under Mitsunobu conditions with an alkyl or cycloalkyl alcohol, triphenylphosphine, DEAD and appropriate solvent (e.g., THF) to give alkylated hydantoin V-3 (e.g., U.S. Patent Application publication US2009/0291946). Reaction of hydantoin V-3 with Lawesson's reagent at an elevated temperature (e.g., 100° C.) can yield thiohydantoin V-4 (Cumming et al., *Bioorganic & Medicinal Chemistry Letters*, 22:2444-2449, 2012) which can then be readily converted to aminohydantoins of Formula I as described above.

Scheme VI

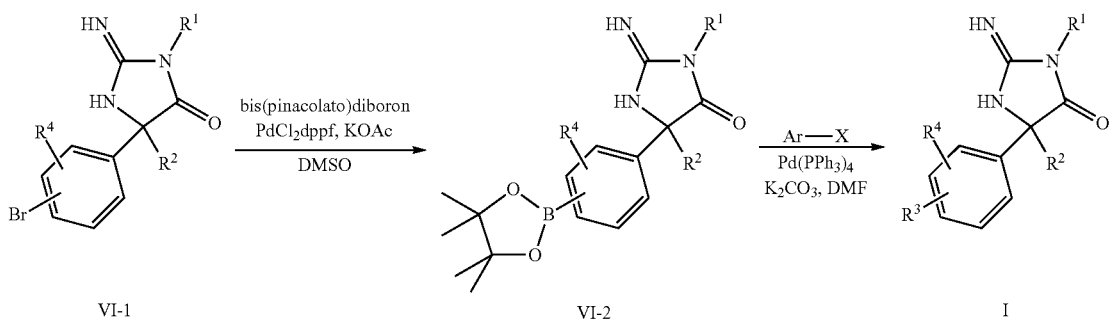

Scheme VI (continued)

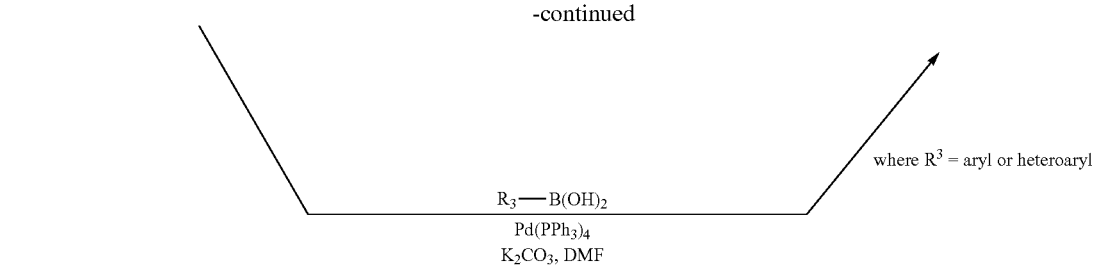

where R³ = aryl or heteroaryl

Scheme VI illustrates methodology useful for preparing compounds of Formula I wherein R³ is aryl or heteroaryl. Briefly, a bromo aminohydantoin VI-1, prepared according to the procedures described above, can be reacted directly under standard Suzuki coupling conditions with an aryl or heteroaryl boronic acid or boronate ester and base in a suitable solvent to give aminohydantoins of Formula I wherein R³ is aryl or heteroaryl. Alternatively, reaction of VI-1 with bis(pinacolato)diboron, PdCl₂dppf and potassium acetate in DMSO at 120° C. can give boronate ester intermediate VI-2. VI-2 can be reacted under standard Suzuki conditions with aryl or heteroaryl halides to give aminohydantoins of Formula I wherein R³ is aryl or heteroaryl.

Scheme VII

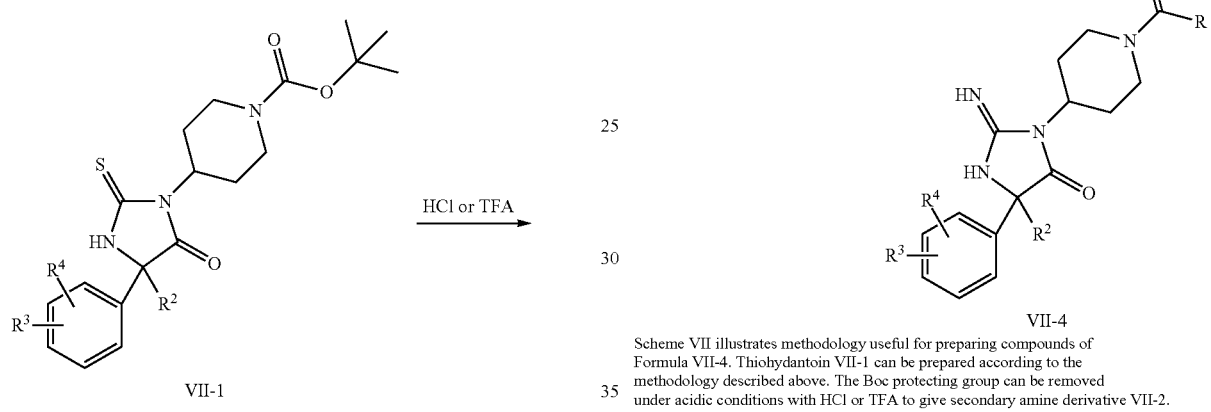

Scheme VII illustrates methodology useful for preparing compounds of Formula VII-4. Thiohydantoin VII-1 can be prepared according to the methodology described above. The Boc protecting group can be removed under acidic conditions with HCl or TFA to give secondary amine derivative VII-2. Treatment with an acid chloride and a base such as triethylamine in a suitable solvent such as dichloromethane give the acylated intermediate VII-3 which can be converted to aminohydantoin VII-4 with ammonium hydroxide and T-butylperoxide as described above.

III. Therapeutic Methods

The invention provides methods to treat patients with a malarial infection or at danger of acquiring one, or to inhibit the spread of the malaria parasite. These methods comprise administering to a patient a compound according to the present invention. The inhibition of parasitemia can be determined by many methods well known in the art, such as assessing parasitemia in malaria-infected human red blood cells.

The invention provides methods to reduce one more symptoms of infection by a malaria parasite by administering an effective amount of a compound of the present invention. The patients that may be treated by this method are any mammal that can be infected by a malaria parasite, and specifically are human patients. Malaria parasites known to infect mammals include, but are not limited to, *Plasmodium falciparum, P. vivax, P. berghei* (rodent-specific), *P. yoelli* (murine-specific), *P. cynomolgi* and *P. knowlesi* (monkey-specific).

The invention also provides methods to treat a patient suspected of having contact with a malaria parasite by administering an effective amount of at least one compound of the present invention. A patient can be suspected of having contact with a malaria parasite, for example, if that patient lives or has traveled in a region of the world where malaria infection of others of the patient's species is common. Treatment by this method may be commenced when the patient is about to, or has already, come into contact with the malaria parasite. Contact with malaria parasites most often occurs by contact with an insect vector such as mosquitoes, so that areas abundant in these insects and the malaria parasite are considered to be among the areas where a patient would have a high probability of coming in contact with a malaria parasite. Such areas of the world include, but are not limited to, parts of Africa, Asia and Latin America. Further, a patient can be suspected of having contact with the malaria parasite if they have come into contact with blood infected with a malaria parasite, are intentionally exposed to the malaria parasite, or accidentally injected with blood or drugs contaminated with the parasite.

A. Pharmaceutical Formulations and Routes of Administration

For administration to a mammal in need of such treatment, the compounds in a therapeutically effective amount are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

It is contemplated that that the concentrations of active agents can vary. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein. In non-limiting aspects, the percentage can be calculated by weight or volume of the total composition. A person of ordinary skill in the art would understand that the concentrations can vary depending on the addition, substitution, and/or subtraction of the compounds, agents, or active ingredients, to the disclosed methods and compositions.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s)

may taken orally and that the timing of which is or is not dependent upon food intake. Thus, for example, the agent can be taken every morning and/or every evening, regardless of when the subject has eaten or will eat.

B. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include intravenous or intramuscular quinine or, increasingly, the artemisinin derivative artesunate. The following is a general discussion of anti-malarial agents.

Quinine and Related Agents.

Quinine has a long history stretching from Peru, and the discovery of the cinchona tree, and the potential uses of its bark, to the current day and a collection of derivatives that are still frequently used in the prevention and treatment of malaria. Quinine is an alkaloid that acts as a blood schizonticidal and weak gametocide against *Plasmodium vivax* and *Plasmodium malariae*. As an alkaloid, it is accumulated in the food vacuoles of *Plasmodium* species, especially *Plasmodium falciparum*. It acts by inhibiting the hemozoin biocrystallization, thus facilitating an aggregation of cytotoxic heme. Quinine is less effective and more toxic as a blood schizonticidal agent than chloroquine; however, it is still very effective and widely used in the treatment of acute cases of severe *P. falciparum*. It is especially useful in areas where there is known to be a high level of resistance to chloroquine, mefloquine, and sulfa drug combinations with pyrimethamine. Quinine is also used in post-exposure treatment of individuals returning from an area where malaria is endemic.

The treatment regimen of quinine is complex and is determined largely by the parasite's level of resistance and the reason for drug therapy (i.e., acute treatment or prophylaxis). The World Health Organization recommendation for quinine is 20 mg/kg first times and 10 mg/kg 8 hr for 5 days where parasites are sensitive to quinine, combined with doxycycline, tetracycline or clindamycin. Doses can be given by oral, intravenous or intramuscular routes. The recommended method depends on the urgency of treatment and the available resources (i.e., sterilized needles for IV or IM injections).

Use of quinine is characterised by a frequently experienced syndrome called cinchonism. Tinnitus (a hearing impairment), rashes, vertigo, nausea, vomiting and abdominal pain are the most common symptoms. Neurological effects are experienced in some cases due to the drug's neurotoxic properties. These actions are mediated through the interactions of Quinine causing a decrease in the excitability of the motor neuron end plates. This often results in functional impairment of the eighth cranial nerve, resulting in confusion, delirium and coma. Quinine can cause hypoglycaemia through its action of stimulating insulin secretion; this occurs in therapeutic doses and therefore it is advised that glucose levels are monitored in all patients every 4-6 hours. This effect can be exaggerated in pregnancy and therefore additional care in administering and monitoring the dosage is essential. Repeated or over-dosage can result in renal failure and death through depression of the respiratory system.

Quinimax and quinidine are the two most commonly used alkaloids related to quinine in the treatment or prevention of malaria. Quinimax is a combination of four alkaloids (quinine, quinidine, cinchoine and cinchonidine). This combination has been shown in several studies to be more effective than quinine, supposedly due to a synergistic action between the four cinchona derivatives. Quinidine is a direct derivative of quinine. It is a distereoisomer, thus having similar antimalarial properties to the parent compound. Quinidine is recommended only for the treatment of severe cases of malaria.

Chloroquine.

Chloroquine was until recently the most widely used antimalarial. It was the original prototype from which most methods of treatment are derived. It is also the least expensive, best tested and safest of all available drugs. The emergence of drug-resistant parasitic strains is rapidly decreasing its effectiveness; however, it is still the first-line drug of choice in most sub-Saharan African countries. It is now suggested that it is used in combination with other antimalarial drugs to extend its effective usage. Popular drugs based on chloroquine phosphate (also called nivaquine) are Chloroquine FNA, Resochin and Dawaquin.

Chloroquine is a 4-aminoquinolone compound with a complicated and still unclear mechanism of action. It is believed to reach high concentrations in the vacuoles of the parasite, which, due to its alkaline nature, raises the internal pH. It controls the conversion of toxic heme to hemozoin by inhibiting the biocrystallization of hemozoin, thus poisoning the parasite through excess levels of toxicity. Other potential mechanisms through which it may act include interfering with the biosynthesis of parasitic nucleic acids and the formation of a chloroquine-haem or chloroquine-DNA complex. The most significant level of activity found is against all forms of the schizonts (with the obvious exception of chloroquine-resistant *P. falciparum* and *P. vivax* strains) and the gametocytes of *P. vivax, P. malariae, P. ovale* as well as the immature gametocytes of *P. falciparum*. Chloroquine also has a significant anti-pyretic and anti-inflammatory effect when used to treat *P. vivax* infections, and thus it may still remain useful even when resistance is more widespread. According to a report on the Science and Development Network website's sub-Saharan Africa section, there is very little drug resistance among children infected with malaria on the island of Madagascar, but what drug resistance there is exists against chloroquinine.

Children and adults should receive 25 mg of chloroquine per kg given over 3 days. A pharmacokinetically superior regime, recommended by the WHO, involves giving an initial dose of 10 mg/kg followed 6-8 hours later by 5 mg/kg, then 5 mg/kg on the following 2 days. For chemoprophylaxis: 5 mg/kg/week (single dose) or 10 mg/kg/week divided into 6 daily doses is advised. Chloroquine is only recommended as a prophylactic drug in regions only affected by *P. vivax* and sensitive *P. falciparum* strains. Chloroquine has been used in the treatment of malaria for many years and no abortifacient or teratogenic effects have been reported during this time; therefore, it is considered very safe to use during pregnancy. However, itching can occur at intolerable level and Chloroquinine can be a provocation factor of psoriasis.

Amodiaquine.

Amodiaquine is a 4-aminoquinolone anti-malarial drug similar in structure and mechanism of action to chloroquine. Amodiaquine has tended to be administered in areas of chloroquine resistance while some patients prefer its tendency to cause less itching than chloroquine. Amodiaquine is now available in a combined formulation with artesunate (ASAQ) and is among the artemisinin-combination therapies recommended by the World Health Organization.

The drug should be given in doses between 25 mg/kg and 35 mg/kg over 3 days in a similar method to that used in chloroquine administration. Adverse reactions are generally similar in severity and type to that seen in chloroquine treatment. In addition, bradycardia, itching, nausea, vomiting and some abdominal pain have been recorded. Some blood and hepatic disorders have also been seen in a small number of patients.

Pyrimethamine.

Pyrimethamine is used in the treatment of uncomplicated malaria. It is particularly useful in cases of chloroquine-resistant *P. falciparum* strains when combined with sulfadoxine. It acts by inhibiting dihydrofolate reductase in the parasite thus preventing the biosynthesis of purines and pyrimidines, thereby halting the processes of DNA synthesis, cell division and reproduction. It acts primarily on the schizonts during the erythrocytic phase, and nowadays is only used in concert with a sulfonamide.

Proguanil.

Proguanil (chloroguanide) is a biguanide; a synthetic derivative of pyrimidine. It was developed in 1945 by a British Antimalarial research group. It has many mechanisms of action but primarily is mediated through conversion to the active metabolite cycloguanil. This inhibits the malarial dihydrofolate reductase enzyme. Its most prominent effect is on the primary tissue stages of *P. falciparum, P. vivax* and *P. ovale*. It has no known effect against hypnozoites therefore is not used in the prevention of relapse. It has a weak blood schizonticidal activity and is not recommended for therapy of acute infection. However it is useful in prophylaxis when combined with atovaquone or chloroquine (in areas where there is no chloroquine resistance). 3 mg/kg is the advised dosage per day, (hence approximate adult dosage is 200 mg). The pharmacokinetic profile of the drugs indicates that a half dose, twice daily maintains the plasma levels with a greater level of consistency, thus giving a greater level of protection. The proguanil-chloroquine combination does not provide effective protection against resistant strains of *P. falciparum*. There are very few side effects to proguanil, with slight hair loss and mouth ulcers being occasionally reported following prophylactic use. Proguanil hydrochloride is marketed as Paludrine by AstraZeneca.

Sulfonamides.

Sulfadoxine and sulfamethoxypyridazine are specific inhibitors of the enzyme dihydropteroate synthetase in the tetrahydrofolate synthesis pathway of malaria parasites. They are structural analogs of p-aminobenzoic acid (PABA) and compete with PABA to block its conversion to dihydrofolic acid. Sulfonamides act on the schizont stages of the erythrocytic (asexual) cycle. When administered alone sulfonamides are not efficacious in treating malaria but co-administration with the antifolate pyrimethamine, most commonly as fixed-dose sulfadoxine-pyrimethamine (Fansidar), produces synergistic effects sufficient to cure sensitive strains of malaria. Sulfonamides are not recommended for chemoprophylaxis because of rare but severe skin reactions experienced. However it is used frequently for clinical episodes of the disease.

Mefloquine.

Mefloquine was developed during the Vietnam War and is chemically related to quinine. It was developed to protect American troops against multi-drug resistant *P. falciparum*. It is a very potent blood schizonticide with a long half-life. It is thought to act by forming toxic heme complexes that damage parasitic food vacuoles. It is now used solely for the prevention of resistant strains of *P. falciparum* despite being effective against *P. vivax, P. ovale* and *P. marlariae*. Mefloquine is effective in prophylaxis and for acute therapy. It is now strictly used for resistant strains (and is usually combined with Artesunate). Chloroquine/proguanil or sulfa drug-pyrimethamine combinations should be used in all other Plasmodia infections. The major commercial manufacturer of mefloquine-based malaria treatment is Roche Pharmaceuticals, which markets the drug under the trade name Lariam.

A dose of 15-25 mg/kg is recommended, depending on the prevalence of mefloquine resistance. The increased dosage is associated with a much greater level of intolerance, most noticeably in young children; with the drug inducing vomiting and oesophagitis. It was not recommended for use during the first trimester, although considered safe during the second and third trimesters; nevertheless, in October 2011, the Centers for Disease Control and Prevention (CDC) changed its recommendation and approved use of Mefloquine for both prophylaxis and treatment of malaria in all trimesters, after the Food and Drug Administration (FDA) changed its categorization from C to B. Mefloquine frequently produces side effects, including nausea, vomiting, diarrhea, abdominal pain and dizziness. Several associations with neurological events have been made, namely affective and anxiety disorders, hallucinations, sleep disturbances, psychosis, toxic encephalopathy, convulsions and delirium. Cardiovascular effects have been recorded with bradycardia and sinus arrhythmia being consistently recorded in 68% of patients treated with mefloquine (in one hospital-based study). Mefloquine can only be taken for a period up to 6 months due to side effects. After this, other drugs (such as those based on paludrine/nivaquine) again need to be taken.

Atovaquone.

Atovaquone is only available in combination with proguanil under the name Malarone, albeit at a price higher than Lariam. It is commonly used in prophylaxis by travellers and used to treat falciparum malaria in developed countries.

Primaquine.

Primaquine is a highly active 8-aminoquinolone that is used in treating all types of malaria infection. It is most effective against gametocytes but also acts on hypnozoites, blood schizonticytes and the dormant plasmodia in *P. vivax* and *P. ovale*. It is the only known drug to cure both relapsing malaria infections and acute cases. The mechanism of action is not fully understood but it is thought to block oxidative metabolism in Plasmodia.

For the prevention of relapse in *P. vivax* and *P. ovale* 0.15 mg/kg should be given for 14 days. As a gametocytocidal drug in *P. falciparum* infections a single dose of 0.75 mg/kg repeated 7 days later is sufficient. This treatment method is only used in conjunction with another effective blood schizonticidal drug. There are few significant side effects although it has been shown that primaquine may cause anorexia, nausea, vomiting, cramps, chest weakness, anaemia, some suppression of myeloid activity and abdominal pains. In cases of over-dosage granulocytopenia may occur.

Artemisinin and Derivatives.

Artemisinin is a Chinese herb (qinghaosu) that has been used in the treatment of fevers for over 1,000 years, thus predating the use of Quinine in the western world. It is derived from the plant *Artemisia annua*. The active compound was isolated first in 1971 and named artemsinin. It is a sesquiterpene lactone with a chemically rare peroxide bridge linkage. It is this that is thought to be responsible for the majority of its anti-malarial action, although the target within the parasite remains controversial. At present it is strictly controlled under WHO guidelines as it has proven to be effective against all forms of multi-drug resistant *P. falciparum*, thus every care is taken to ensure compliance and adherence together with other behaviors associated with the development of resistance. It is also only given in combination with other anti-malarials.

Artemisinin has a very rapid action and the vast majority of acute patients treated show significant improvement within 1-3 days of receiving treatment. It has demonstrated the fastest clearance of all anti-malarials currently used and acts primarily on the trophozite phase, thus preventing progression of the disease. Semi-synthetic artemisinin derivatives (e.g. artesunate, artemether) are easier to use than the parent compound and are converted rapidly once in the body to the active compound dihydroartemesinin. On the first day of treatment 20 mg/kg should be given, this dose is then reduced to 10 mg/kg per day for the 6 following days. Few side effects are associated with artemesinin use. However, headaches, nausea, vomiting, abnormal bleeding, dark urine, itching and some drug fever have been reported by a small number of patients. Some cardiac changes were reported during a clinical trial, notably non specific ST changes and a first degree atrioventricular block (these disappeared when the patients recovered from the malarial fever).

Artemether is a methyl ether derivative of dihydroartemesinin. It is similar to artemesinin in mode of action but demonstrates a reduced ability as a hypnozoiticidal compound, instead acting more significantly to decrease gametocyte carriage. Similar restrictions are in place, as with artemesinin, to prevent the development of resistance, therefore it is only used in combination therapy for severe acute cases of drug-resistant *P. falciparum*. It should be administered in a 7 day course with 4 mg/kg given per day for 3 days, followed by 1.6 mg/kg for 3 days. Side effects of the drug are few but include potential neurotoxicity developing if high doses are given.

Artesunate is a hemisuccinate derivative of the active metabolite dihydroartemisin. Currently it is the most frequently used of all the artemesinin-type drugs. Its only effect is mediated through a reduction in the gametocyte transmission. It is used in combination therapy and is effective in cases of uncomplicated *P. falciparum*. The dosage recommended by the WHO is a 5 or 7 day course (depending on the predicted adherence level) of 4 mg/kg for 3 days (usually given in combination with mefloquine) followed by 2 mg/kg for the remaining 2 or 4 days. In large studies carried out on over 10,000 patients in Thailand no adverse effects have been shown.

Dihydroartemisinin is the active metabolite to which artemesinin is reduced. It is the most effective artemesinin compound and the least stable. It has a strong blood schizonticidal action and reduces gametocyte transmission. It is used for therapeutic treatment of cases of resistant and uncomplicated *P. falciparum*. 4 mg/kg doses are recommended on the first day of therapy followed by 2 mg/kg for 6 days. As with artesunate, no side effects to treatment have thus far been recorded.

Arteether is an ethyl ether derivative of dihydroartemisinin. It is used in combination therapy for cases of uncomplicated resistant *P. falciparum*. The recommended dosage is 150 mg/kg per day for 3 days given by IM injections. With the exception of a small number of cases demonstrating neurotoxicity following parenteral administration no side effects have been recorded.

Halofantrine.

Halofantrine is a relatively new drug developed by the Walter Reed Army Institute of Research in the 1960s. It is a phenanthrene methanol, chemically related to Quinine and acts acting as a blood schizonticide effective against all *plasmodium* parasites. Its mechanism of action is similar to other anti-malarials. Cytotoxic complexes are formed with ferritoporphyrin XI that cause plasmodial membrane damage. Despite being effective against drug resistant parasites, halofantrine is not commonly used in the treatment (prophylactic or therapeutic) of malaria due to its high cost. It has very variable bioavailability and has been shown to have potentially high levels of cardiotoxicity. It is still a useful drug and can be used in patients that are known to be free of heart disease and are suffering from severe and resistant forms of acute malaria. A popular drug based on halofantrine is Halfan. The level of governmental control and the prescription-only basis on which it can be used contributes to the cost, thus halofantrine is not frequently used.

A dose of 8 mg/kg of halofantrine is advised to be given in three doses at six hour intervals for the duration of the clinical episode. It is not recommended for children under 10 kg despite data supporting the use and demonstrating that it is well tolerated. The most frequently experienced side-effects include nausea, abdominal pain, diarrhea, and itch. Severe ventricular dysrhythmias, occasionally causing death are seen when high doses are administered. This is due to prolongation of the QTc interval. Halofantrine is not recommended for use in pregnancy and lactation, in small children, or in patients that have taken mefloquine previously. Lumefantrine is a relative of halofantrine that is used in some combination antimalarial regimens.

Doxycycline.

Probably one of the more prevalent antimalarial drugs prescribed, due to its relative effectiveness and cheapness, doxycycline is a tetracycline compound derived from oxytetracycline. The tetracyclines were one of the earliest groups of antibiotics to be developed and are still used widely in many types of infection. It is a bacteriostatic agent that acts to inhibit the process of protein synthesis by binding to the 30S ribosomal subunit thus preventing the 50s and 30s units from bonding. Doxycycline is used primarily for chemoprophylaxis in areas where chloroquine resistance exists. It can also be used in combination with quinine to treat resistant cases of *P. falciparum* but has a very slow action in acute malaria, and should not be used as monotherapy. When treating acute cases and given in combination with quinine; 100 mg of doxycycline should be given per day for 7 days. In prophylactic therapy, 100 mg (adult dose) of doxycycline should be given every day during exposure to malaria.

The most commonly experienced side effects are permanent enamel hypoplasia, transient depression of bone growth, gastrointestinal disturbances and some increased levels of photosensitivity. Due to its effect of bone and tooth growth it is not used in children under 8, pregnant or lactating women and those with a known hepatic dysfunction.

Tetracycline is only used in combination for the treatment of acute cases of *P. falciparum* infections. This is due to its slow onset. Unlike doxycycline it is not used in chemoprophylaxis. For tetracycline, 250 mg is the recommended adult dosage (it should not be used in children) for 5 or 7 days depending on the level of adherence and compliance expected. Esophageal ulceration, gastrointestinal upset and interferences with the process of ossification and depression of bone growth are known to occur. The majority of side effects associated with doxycycline are also experienced.

Clindamycin.

Clindamycin is a derivative of lincomycin, with a slow action against blood schizonticides. It is only used in combination with quinine in the treatment of acute cases of resistant *P. falciparum* infections and not as a prophylactic. Being more expensive and toxic than the other antibiotic alternatives, it is used only in cases where the Tetracyclines are contraindicated (for example in children).

Clindamycin should be given in conjunction with quinine as a 300 mg dose (in adults) four times a day for 5 days. The only side effects recorded in patients taking clindamycin are nausea, vomiting and abdominal pains and cramps. However, these can be alleviated by consuming large quantities of water and food when taking the drug. Pseudomembranous colitis (caused by *Clostridium difficile*) has also developed in some patients; this condition may be fatal in a small number of cases.

IV. Examples

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

General Methods.

All materials were obtained from commercial sources and used as purchased. Chromatography solvents were chromatography grade and were used without further purification. Thin layer chromatography (TLC) analysis was performed using Merck silica gel 60 F-254 thin layer plates. LC-MS analyses were performed on an Agilent 1200HPLC/MCD electrospray mass spectrometer in positive ion mode. The scan range was 100-1000d. Preparative reverse phase HPLC was performed on a SHIMADZU LC-20AP equipped with a C18 column and a methanol/water gradient. The purity of tested compounds was ≥95% as determined by combustion analysis or by HPLC conducted on a DIONEX P-680A system using a reverse phase C18 column with diode array detector unless stated otherwise. NMR spectra were recorded on a Bruker 400 MHz spectrometer. The signal of the deuterated solvent was used as internal reference. Chemical shifts (δ) are given in ppm and are referenced to residual not fully deuterated solvent signal. Coupling constants (J) are given in Hz.

Intermediate A1

Preparation of 1-Cyclohexylthiourea

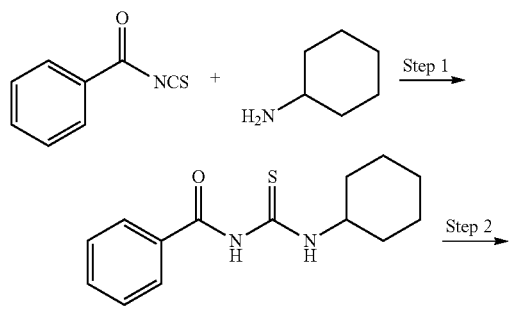

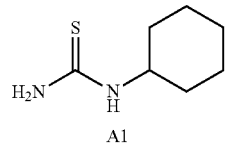

Step 1. Preparation of N-(cyclohexylcarbamothioyl)benzamide

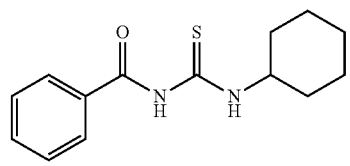 [SMILES: O=C(NC(=S)NC1CCCCC1)c1ccccc1]

Benzoyl isothiocyanate (19.4 g, 118.9 mmol) was dissolved in dichloromethane and cooled to 0° C. Cyclohexylamine (13 g, 131.1 mmol) was added dropwise. Then the reaction was stirred at room temperature for 2 h. The mixture was washed with water, dried over sodium sulfate. Concentration under vaccum gave the title compound as a pale white solid in quantitative yield.

Step 2. Preparation of 1-cyclohexylthiourea

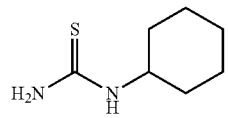

To a solution of N-(cyclohexylcarbamothioyl)benzamide (17.1 g, 65.5 mmol) in ethanol was added aqueous potassium carbonate (18.2 g, 132.2 mmol). The mixture was stirred at reflux temperature for 4 h. The organic layer was concentrated to a small volume, after which the product could be collected by filtration, then washed with petroleum ether and dried in vacuo to give the title compound as a white solid (9.8 g, 95% two steps).

Intermediates A2-A41

Preparation of Thioureas A2-A41

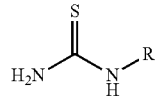

Thioureas A2-A41 were prepared according to the procedure for Intermediate A1 from the corresponding alkyl amine. Examples of Intermediates A2-A41 are shown in Table 1.

TABLE 1

Examples of Intermediates A2-A41.

| Intermediate | Name | Yield (%) |
|---|---|---|
| A2 | 1-(tetrahydro-2H-pyran-4-yl)thiourea | ~62 |
| A3 | 1-(cyclohexylmethyl)thiourea | ~96 |
| A4 | 1-((tetrahydro-2H-pyran-4-yl)methyl)-thiourea | ~60 |
| A5 | 1-cyclopropylthiourea | ~90 |
| A6 | 1-cyclobutylthiourea | ~92 |
| A7 | 1-cyclopentylthiourea | ~90 |
| A8 | 1-cycloheptylthiourea | ~50 |
| A9 | tert-butyl 4-thioureidopiperidine-1-carboxylate | ~94 |
| A10 | 1-benzylthiourea | ~90 |
| A11 | 1-(pyridin-4-ylmethyl)thiourea | ~80 |
| A12 | 1-(pyridin-3-ylmethyl)thiourea | ~80 |
| A13 | 1-(pyridin-2-ylmethyl)thiourea | ~80 |
| A14 | 1-(naphthalen-1-ylmethyl)thiourea | ~85 |
| A15 | 1-(1-methylpiperidin-4-yl)thiourea | ~90 |
| A16 | 1-(4-methylbenzyl)thiourea | ~95 |
| A17 | 1-(4-chlorobenzyl)thiourea | ~95 |
| A18 | 1-(4-methoxybenzyl)thiourea | ~95 |
| A19 | 1-(2-chlorobenzyl)thiourea | ~95 |
| A20 | 1-(3-chlorobenzyl)thiourea | ~95 |
| A21 | 1-(3-methoxybenzyl)thiourea | ~95 |
| A22 | 1-(2-methoxybenzyl)thiourea | ~95 |
| A23 | 1-(3-(trifluoromethyl)benzyl)thiourea | ~95 |
| A24 | 1-(1-benzylpiperidin-4-yl)thiourea | quantitative |
| A25 | 1-neopentylthiourea | ~85 |
| A26 | 1-(3-methylbenzyl)thiourea | ~95 |
| A27 | 1-(2,5-dimethylbenzyl)thiourea | ~92 |
| A28 | 1-((tetrahydrofuran-2-yl)methyl)thiourea | ~60 |
| A29 | 1-(adamantan-1-yl)methyl)thiourea | ~90 |
| A30 | 1-(2,3-dimethylbenzyl)thiourea | ~95 |
| A31 | 1-(2,6-dimethylbenzyl)thiourea | ~95 |
| A32 | 1-((3-methylpyridin-2-yl)methyl)thiourea | ~80 |
| A33 | 1-(2-methylbenzyl)thiourea | ~95 |
| A34 | 1-(2-(trifluoromethyl)benzyl)thiourea | ~92 |
| A35 | 1-(2-fluorobenzyl)thiourea | ~90 |
| A36 | 1-(2-bromobenzyl)thiourea | ~90 |
| A37 | 1-((1-methylpiperidin-4-yl)methyl)-thiourea | ~95 |
| A38 | tert-butyl 4-(thioureidomethyl)piperidine-1-carboxylate | ~95 |
| A39 | 1-(4-methylcyclohexyl)thiourea | |

Intermediate B1

Preparation of 1-phenyl-2-(3-(pyridin-3-yl)phenyl)ethane-1,2-dione

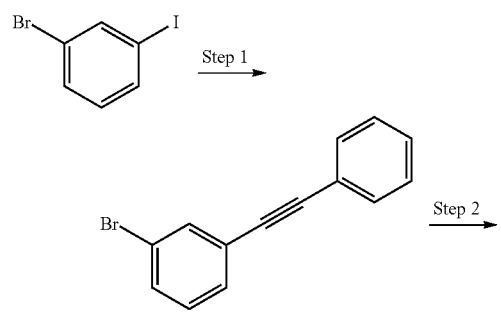

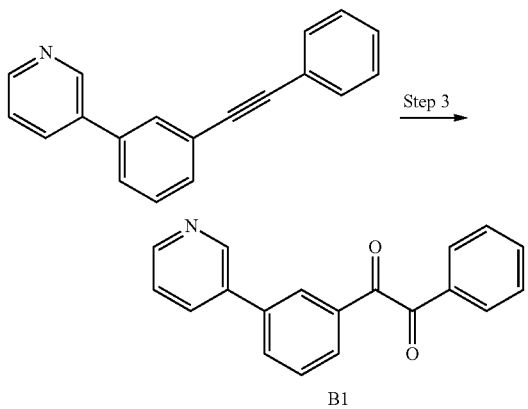

Step 1. Preparation of 1-bromo-3-(phenylethynyl)benzene

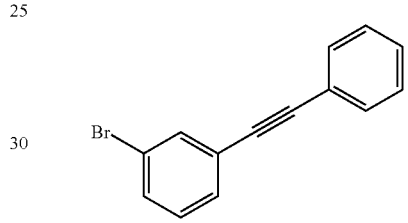

1-bromo-3-iodobenzene (15.3 g, 54.0 mmol), phenylacetylene (5 g, 49.0 mmol), tetrakis(triphenylphosphine)palladium (2.8 g, 2.4 mmol) and copper(I) iodide (0.46 g, 2.4 mmol) were dissolved in dry toluene and diisopropylamine (35 mL, 196 mmol) under a nitrogen atmosphere. The reaction was stirred at room temperature overnight. The mixture was extracted with ethyl acetate and the organic layer was dried in vacuo to give the title compound as a residue that was used without further purification.

Step 2. Preparation of 3-(3-(phenylethynyl)phenyl)pyridine

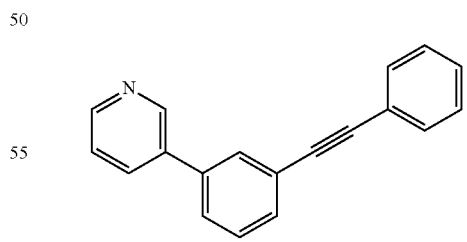

1-Bromo-3-(phenylethynyl)benzene (3 g, 11.7 mmol), 3-pyridylboronic acid (1.6 g, 13.0 mmol), Tetrakis(triphenylphosphine)palladium (0.3 g, 0.26 mmol) and potassium carbonate (3.2 g, 23.2 mmol) were dissolved in N,N-dimethylformamide and the reaction was stirred at 100° C. overnight under nitrogen. The mixture was extracted with dichloromethane and the combined organic phases were washed with water, dried over sodium sulfate and concentrated in vacuo to give the title compound as oil (1.3 g, 43% yield).

Step 3. Preparation of 1-phenyl-2-(3-(pyridin-3-yl)phenyl)ethane-1,2-dione

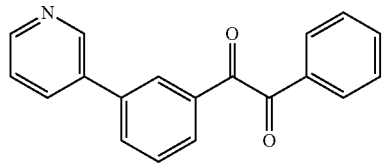

B1

To a solution of 3-(3-(phenylethynyl)phenyl)pyridine (5.4 g, 21.2 mmol) in dimethyl sulfoxide was added palladium chloride (0.87 g, 4.9 mmol) under nitrogen. The reaction was heated to 110° C. overnight. The mixture was extracted with dichloromethane. The combined organic phases were washed with water, dried over sodium sulfate and concentrated in vacuo. The residue was purified over a silica column to give the title compound as a white solid (2.3 g, 38% yield).

Intermediates B2-B21

Preparation of Diones B2-B21

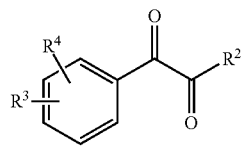

Diones B2-B21 were prepared according to the procedure for Intermediate B1, Steps 1-3 from the corresponding aryl/cycloalkyl alkyne and aryl/heteroaryl halide in Step 1 and aryl boronic acid in Step 2. Examples of Intermediates B2-B21 are shown in Table 2.

TABLE 2

Examples of dione Intermediates B2-B21.

| Intermediate | Name | Yield (%) |
|---|---|---|
| B2 | 1-([1,1'-biphenyl]-3-yl)-2-phenylethane-1,2-dione | ~50 |
| B3 | 1-phenyl-2-(3-(pyridin-4-yl)phenyl)ethane-1,2-dione | ~30 |
| B4 | 1-phenyl-2-(3-(pyridin-2-yl)phenyl)ethane-1,2-dione | ~30 |
| B5 | 1-(3'-methoxy-[1,1'-biphenyl]-3-yl)-2-phenylethane-1,2-dione | ~50 |
| B6 | 1-(4-methoxyphenyl)-2-(3-(pyridin-3-yl)phenyl)ethane-1,2-dione | ~30 |
| B7 | 1-(4-methoxyphenyl)-2-(3-(pyridin-4-yl)phenyl)ethane-1,2-dione | ~30 |
| B8 | 1-([1,1'-biphenyl]-3-yl)-2-(4-methoxyphenyl)ethane-1,2-dione | ~50 |
| B9 | 1-(4-methoxyphenyl)-2-(3-(pyridin-2-yl)phenyl)ethane-1,2-dione | ~30 |
| B10 | 1-(3-methoxyphenyl)-2-(3-(pyridin-3-yl)phenyl)ethane-1,2-dione | ~30 |
| B11 | 1-(3-methoxyphenyl)-2-(3-(pyridin-4-yl)phenyl)ethane-1,2-dione | ~30 |
| B12 | 1-(3-methoxyphenyl)-2-(3-(pyridin-2-yl)phenyl)ethane-1,2-dione | ~30 |
| B13 | 1-(4-methoxyphenyl)-2-(pyridin-3-yl)ethane-1,2-dione | ~50 |

TABLE 2-continued

Examples of dione Intermediates B2-B21.

| Intermediate | Name | Yield (%) |
|---|---|---|
| B14 | 1-cyclopropyl-2-(4-methoxyphenyl)ethane-1,2-dione | ~50 |
| B15 | 1-cyclopropyl-2-(3'-methoxy-[1,1'-biphenyl]-3-yl)ethane-1,2-dione | ~30 |
| B16 | 1-cyclohexyl-2-(4-methoxyphenyl)ethane-1,2-dione | ~50 |
| B17 | 1-(4-methoxyphenyl)-2-(pyridin-2-yl)ethane-1,2-dione | ~50 |
| B18 | 1-(4-methoxyphenyl)-2-(pyrimidin-5-yl)ethane-1,2-dione | ~30 |
| B19 | 1-(4-methoxyphenyl)-2-(pyridin-4-yl)ethane-1,2-dione | ~40 |
| B20 | 1-cyclopentyl-2-(4-methoxyphenyl)ethane-1,2-dione | ~30 |
| B21 | 1-(4-methoxyphenyl)-2-(1-methyl-1H-pyrazol-4-yl)ethane-1,2-dione | ~40 |
| B22 | 5'-(2-cyclopropyl-2-oxoacetyl)-2'-methoxy-[1,1'-biphenyl]-3-carbonitrile | |
| B23 | 1-(4-chlorophenyl)-2-cyclopropylethane-1,2-dione | |
| B24 | 1-cyclopropyl-2-(3-methoxyphenyl)ethane-1,2-dione | |
| B25 | 1-(4-chloro-3-methoxyphenyl)-2-cyclohexylethane-1,2-dione | |
| B26 | 1-cyclopropyl-2-(3-hydroxyphenyl)ethane-1,2-dione | |
| B27 | 1-cyclopropyl-2-(4-(pyridin-3-yl)phenyl)ethane-1,2-dione | |
| B28 | 1-cyclopropyl-2-(4-hydroxyphenyl)ethane-1,2-dione | |
| B29 | 4-((4-(2-cyclopropyl-2-oxoacetyl)phenoxy)methyl)benzonitrile | |
| B30 | 1-cyclopropyl-2-(2-hydroxyphenyl)ethane-1,2-dione | |
| B31 | 1-(3-isobutoxyphenyl)-2-(3-(pyridin-3-yl)phenyl)-ethane-1,2-dione | |
| B32 | 1-(4-isobutoxyphenyl)-2-(3-(pyridin-3-yl)phenyl)-ethane-1,2-dione | |
| B33 | 3'-(2-oxo-2-phenylacetyl)-[1,1'-biphenyl]-3-carbonitrile | |
| B34 | 3'-(2-cyclopropyl-2-oxoacetyl)-[1,1'-biphenyl]-3-carbonitrile | |
| B35 | 1-cyclopropyl-2-(3-(pyridin-3-yl)phenyl)ethane-1,2-dione | |
| B36 | 5-(3-(2-cyclopropyl-2-oxoacetyl)phenyl)nicotinonitrile | |
| B37 | 1-(3-(5-chloropyridin-3-yl)phenyl)-2-cyclopropylethane-1,2-dione | |
| B38 | 1-cyclopropyl-2-(4-methoxy-3-(pyridin-3-yl)phenyl)-ethane-1,2-dione | |
| B39 | 3'-(2-cyclohexyl-2-oxoacetyl)-[1,1'-biphenyl]-3-carbonitrile | |
| B40 | 1-cyclopropyl-2-(4-(trifluoromethoxy)phenyl)-ethane-1,2-dione | |
| B41 | 1-(3-chlorophenyl)-2-cyclopropylethane-1,2-dione | |
| B42 | 1-cyclopropyl-2-(3'-ethynyl-[1,1'-biphenyl]-3-yl)ethane-1,2-dione | |
| B43 | 1-cyclopropyl-2-(3,4-difluorophenyl)ethane-1,2-dione | |
| B44 | 1-(2-chlorophenyl)-2-cyclopropylethane-1,2-dione | |
| B45 | 1-cyclopropyl-2-(3-(5-(prop-1-yn-1-yl)pyridin-3-yl)-phenyl)ethane-1,2-dione | |
| B46 | 1-(3-(5-chloropyridin-3-yl)phenyl)-2-cyclohexylethane-1,2-dione | |
| B47 | 1-cyclohexyl-2-(3-(pyridin-3-yl)phenyl)ethane-1,2-dione | |
| B48 | 1-cyclopropyl-2-(2-methoxyphenyl)ethane-1,2-dione | |
| B49 | 1,2-bis(4-hydroxyphenyl)ethane-1,2-dione | |
| B50 | 1-cyclopropyl-2-(3-hydroxyphenyl)ethane-1,2-dione | |
| B51 | 1-(4'-chloro-[1,1'-biphenyl]-3-yl)-2-cyclopropylethane-1,2-dione | |
| B52 | 1-cyclopropyl-2-(2-methoxyphenyl)ethane-1,2-dione | |
| B53 | 4-((3-(2-cyclopropyl-2-oxoacetyl)phenoxy)methyl)benzonitrile | |
| B54 | 1-cyclopropyl-2-(3-phenoxyphenyl)ethane-1,2-dione | |
| B55 | 1-cyclopropyl-2-(3,4-dichlorophenyl)ethane-1,2-dione | |
| B56 | 1-(4-chlorophenyl)-2-cyclohexylethane-1,2-dione | |
| B57 | 1-(4-chlorophenyl)-2-cyclopropylethane-1,2-dione | |

Example 117

Preparation of 3-cyclohexyl-2-imino-5,5-bis(4-methoxyphenyl)imidazolidin-4-one

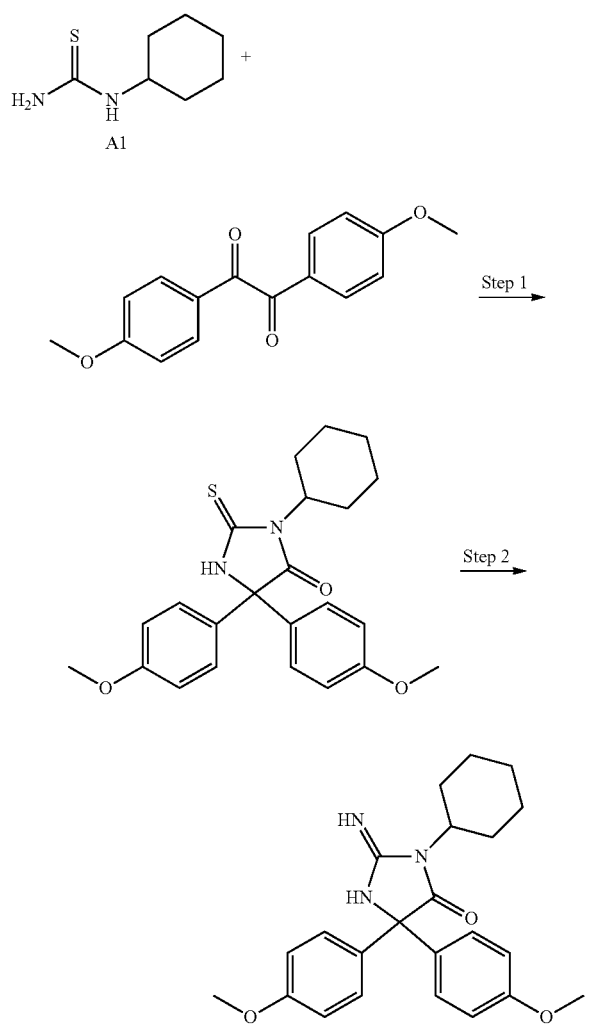

Step 1. Preparation of 3-cyclohexyl-5,5-bis(4-methoxyphenyl)-2-thioxoimidazolidin-4-one

Intermediate A1

(1.3 g, 8.2 mmol) and 4,4'-dimethoxybenzil (CAS 1226-42-2; 2 g, 7.4 mmol) were dissolved in dimethyl sulfoxide and the solution was heated to 110° C. An aqueous solution of potassium hydroxide (0.62 g, 11.1 mmol) was added drop wise and the resulting mixture was stirred for 10 min, allowed to cool, and then extracted with dichloromethane. The combined organic phases were washed with water, dried over sodium sulfate and concentrated in vacuo to give the title compound as a residue which was used without further purification.

Step 2. Preparation of 3-cyclohexyl-2-imino-5,5-bis (4-methoxyphenyl)-imidazolidin-4-one (117)

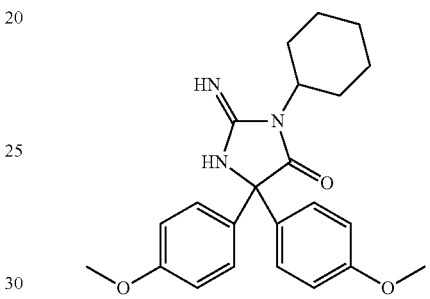

To a solution of 3-cyclohexyl-5,5-bis(4-methoxyphenyl)-2-thioxoimidazolidin-4-one (3.0 g, 7.3 mmol) in methanol was added aqueous ammonium (25%, 40 mL) and tert-butyl hydroperoxide (70%, 10 mL) separately, and the resulting solution was stirred at room temperature overnight. The mixture was extracted with dichloromethane and the organic layer was concentrated in vacuo. The residue was purified over a silica column to give the title compound as a white solid (1.7 g, 59% two steps). $^1$H NMR (400 MHz, d$^6$-DMSO) δ 7.25 (d, J=8.0 Hz, 4H), 6.84 (d, J=7.6 Hz, 4H), 6.47 (s, 1H), 3.71 (s, 6H), 3.70 (s, 1H), 2.09 (m, 2H), 1.74 (m, 2H), 1.52-1.60 (m, 3H), 1.26 (m, 2H), 1.13 (m, 1H). LC-MS m/z 394.2 (M+H).

Examples 100 to 336

Preparation of Aminohydantoins 100 to 336

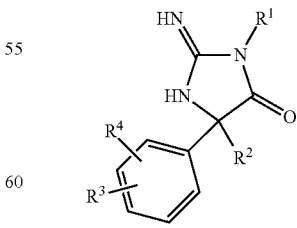

Aminohydantoins 100 to 336 (Table 3) were prepared according to the procedure for 117 from the corresponding thiourea Intermediates A1-A38 and corresponding dione (Intermediates B1-B21 or commercially available diones).

TABLE 3

Examples 100 to 336.
This table includes both compounds of the present invention as well as comparison compounds.

| Ex. | IUPAC Name | Structure | Yield (%) | ¹H NMR | LC-MS m/z (M + H) |
| --- | --- | --- | --- | --- | --- |
| 100 | 3-cyclohexyl-2-imino-5,5-diphenyl-imidazolidin-4-one | 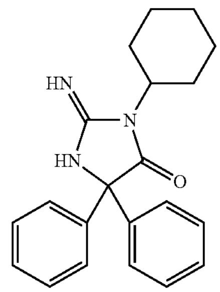 [SMILES: N=C1NC(c2ccccc2)(c2ccccc2)C(=O)N1C1CCCCC1] | 55 | (400 MHz, d⁶-DMSO) δ 7.22-7.37 (m, 10H), 6.54 (s, 1H), 3.70 (m, 1H), 2.09 (m, 2H), 1.75 (m, 2H), 1.55 (m, 3H), 1.08-1.28 (m, 3H) | 334.1 |
| 102 | 3-benzyl-2-imino-5,5-diphenyl-imidazolidin-4-one | 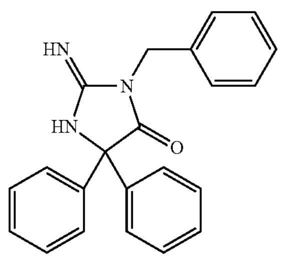 [SMILES: N=C1NC(c2ccccc2)(c2ccccc2)C(=O)N1Cc1ccccc1] | 55 | (400 MHz, d⁶-DMSO,) δ 7.41-7.43 (m, 4H), 7.18-7.29 (m, 11H), 6.70 (s, 1H), 4.73 (s, 2H) | 342.1 |
| 105 | 3-benzyl-2-imino-5,5-bis(3-methoxy-phenyl)imidazolidin-4-one | 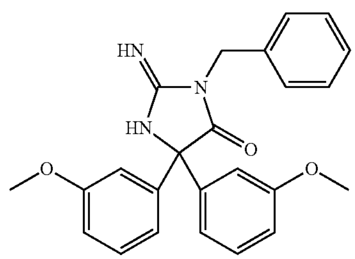 [SMILES: COc1cccc(C2(c3cccc(OC)c3)NC(=N)N(Cc3ccccc3)C2=O)c1] | 42 | (400 MHz, d⁶-DMSO) δ 7.19-7.24 (m, 7H), 6.96-7.02 (m, 4H), 6.80 (m, 2H), 6.72 (s, 1H), 4.71 (s, 2H), 3.67 (s, 6H) | 402.1 |
| 128 | 3-cyclohexyl-2-imino-5,5-bis(3-methoxyphenyl)-imidazolidin-4-one | 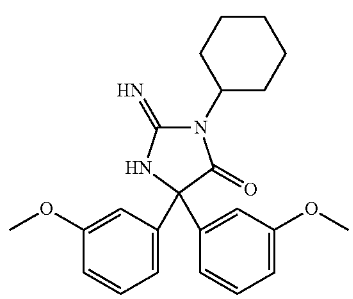 | 55 | (400 MHz, d⁶-DMSO) δ 7.20 (m, 2H), 6.78-6.98 (m, 6H), 6.56 (s, 1H), 3.71 (m, 1H), 3.70 (s, 6H), 2.08 (m, 2H), 1.74 (m, 2H), 1.52 (m, 3H), 1.10-1.30 (m, 3H) | 394.2 |
| 135 | 2-imino-3-methyl-5-phenyl-5-[3-(pyridin-3-yl)phenyl]-imidazolidin-4-one | 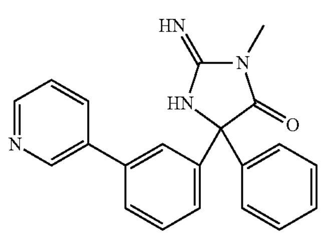 [SMILES: CN1C(=N)NC(c2ccccc2)(c2cccc(-c3cccnc3)c2)C1=O] | 30 | ¹H NMR (d⁶-DMSO, 400 MHz) δ 8.75 (s, 1H), 7.60 (dd, J = 1.6, 4.8 Hz, 1H), 7.93 (d, J = 8.0 Hz, 1H), 7.76 (s, 1H), 7.42-7.59 (m, 6H), 7.20-7.32 (m, 3H), 6.69 (s, 1H), 2.99 (s, 3H) | 343.1 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 136 | 3-cyclohexyl-2-imino-5-phenyl-5-[3-(pyridin-3-yl)-phenyl]imidazolidin-4-one | 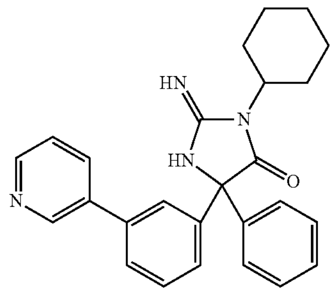 [SMILES: N=C1NC(c2ccccc2)(c2cccc(-c3cccnc3)c2)C(=O)N1C1CCCCC1] | 40 | (400 MHz, d⁶-DMSO) δ 8.74 (s, 1H), 8.57 (d, J = 3.2 Hz, 1H), 7.91 (d, J = 7.6 Hz, 1H), 7.69 (s, 1H), 7.58 (d, J = 7.2 Hz, 1H), 7.41-7.50 (m, 6H), 7.30 (t, J = 7.2, 7.6 Hz, 2H), 7.23 (d, J = 7.2 Hz, 1H), 6.60 (s, 1H), 3.72 (m, 1H), 2.10 (m, 2H), 1.73-1.76 (m, 2H), 1.51-1.59 (m, 3H), 1.07-1.35 (m, 3H) | 411.2 |
| 141 | 3-cyclohexyl-2-imino-5-(4-methoxyphenyl)-5-phenylimidazolidin-4-one | 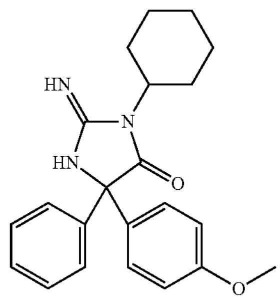 [SMILES: COc1ccc(C2(c3ccccc3)NC(=N)N(C3CCCCC3)C2=O)cc1] | 42 | (400 MHz, d⁶-DMSO) δ 7.26-7.34 (m, 7H), 6.85 (d, J = 8.8 Hz, 2H), 6.50 (s, 1H), 3.71 (m, 4H), 2.10 (m, 2H), 1.74 (m, 2H), 1.54 (m, 3H), 1.24 (m, 2H), 1.17 (m, 1H) | 364.2 |
| 142 | 3-cyclopropyl-2-imino-5,5-diphenylimidazolidin-4-one | 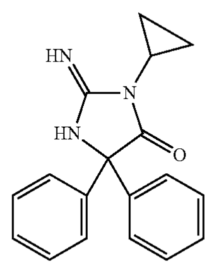 [SMILES: N=C1NC(c2ccccc2)(c2ccccc2)C(=O)N1C1CC1] | 52 | (400 MHz, d⁶-DMSO) δ 7.39 (m, 4H), 7.28 (m, 4H), 7.20 (m, 2H), 6.53 (s, 1H), 2.55 (m, 1H), 0.90-0.95 (m, 2H), 0.70-0.74 (m, 2H). | 292.1 |
| 153 | 3-cyclohexyl-2-imino-5-(3-methoxyphenyl)-5-phenylimidazolidin-4-one | 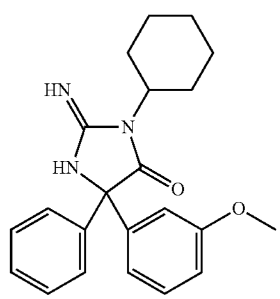 [SMILES: COc1cccc(C2(c3ccccc3)NC(=N)N(C3CCCCC3)C2=O)c1] | 45 | (400 MHz, d⁶-DMSO) δ 7.19-7.37 (m, 6H), 6.93-6.98 (m, 3H), 6.80 (d, J = 6.8 Hz, 1H), 3.70 (m, 1H), 3.68 (s, 3H), 2.09 (m, 2H), 1.75 (m, 2H), 1.51-1.59 (m, 3H), 1.07-1.35 (m, 3H) | 364.1 |
| 154 | 5,5-bis(4-bromophenyl)-3-cyclohexyl-2-iminoimidazolidin-4-one | 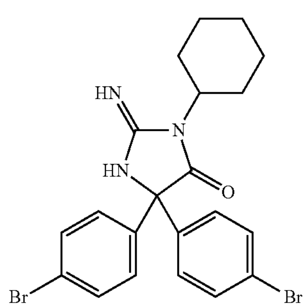 [SMILES: N=C1NC(c2ccc(Br)cc2)(c2ccc(Br)cc2)C(=O)N1C1CCCCC1] | 45 | (400 MHz, d⁶-DMSO) δ 7.50 (d, 8.4 Hz, 4H), 7.29 (d, J = 8.4 Hz, 4H), 6.67 (s, 1H), 3.69 (m, 1H), 2.01-2.10 (m, 2H), 1.74 (m, 2H), 1.56 (m, 3H), 1.04-1.30 (m, 3H) | 490.0 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 155 | 5,5-bis(4-chlorophenyl)-3-cyclohexyl-2-iminoimidazolidin-4-one | 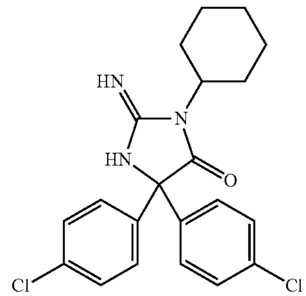 [SMILES: N=C1NC(c2ccc(Cl)cc2)(c2ccc(Cl)cc2)C(=O)N1C1CCCCC1] | 45 | (400 MHz, d$^6$-DMSO) δ 7.34-7.39 (m, 8H), 6.67 (s, 1H), 3.70 (m, 1H), 2.02-2.10 (m, 2H), 1.73 (m, 2H), 1.56 (m, 3H), 1.09-1.29 (m, 3H) | 402.1 |
| 156 | 3-cyclohexyl-2-imino-5,5-bis(4-methylphenyl)-imidazolidin-4-one | 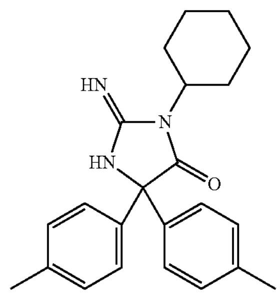 | 45 | (400 MHz, d$^6$-DMSO) δ 7.20 (d, J = 8.4 Hz, 4H), 7.12 (d, J = 8.4 Hz, 4H), 3.80 (m, 1H), 2.26 (s, 6H), 2.07 (m, 2H), 1.73 (m, 2H), 1.58 (m, 3H), 1.07-1.31 (m, 3H) | 362.2 |
| 157 | 3-cyclohexyl-5,5-bis(4-ethoxyphenyl)-2-iminoimidazolidin-4-one | 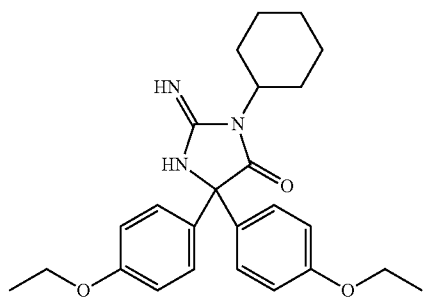 [SMILES: CCOc1ccc(C2(c3ccc(OCC)cc3)NC(=N)N(C3CCCCC3)C2=O)cc1] | 50 | (400 MHz, d$^6$-DMSO) δ 7.22 (d, J = 8.4 Hz, 4H), 6.82 (d, J = 8.4 Hz, 4H), 6.44 (s, 1H), 3.98 (m, 4H), 3.69 (s, 1H), 2.08 (m, 2H), 1.74 (m, 2H), 1.51-1.59 (m, 3H), 1.07-1.35 (m, 9H) | 422.2 |
| 158 | 3-cyclopropyl-2-imino-5,5-bis(4-methoxyphenyl)-imidazolidin-4-one | 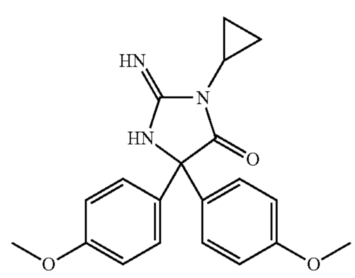 | 55 | (400 MHz, d$^6$-DMSO) δ 7.27 (d, J = 8.8 Hz, 4H), 6.83 (d, J = 8.8 Hz, 4H), 6.50 (s, 1H), 3.70 (s, 6H), 2.50-2.55 (m, 1H), 1.92 (m, 2H), 0.71 (m, 2H) | 352.1 |
| 159 | 3-cyclopentyl-2-imino-5,5-bis(4-methoxyphenyl)-imidazolidin-4-one | 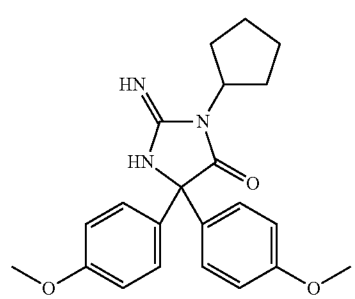 | 50 | (400 MHz, d$^6$-DMSO) δ 7.25 (d, J = 8.4 Hz, 4H), 6.85 (d, J = 8.4 Hz, 4H), 6.47 (s, 1H), 4.21 (s, 1H), 3.71 (s, 6H), 1.94 (m, 2H), 1.74-1.79 (m, 4H), 1.50 (m, 2H) | 380.1 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 162 | 3-benzyl-2-imino-5,5-bis(4-methoxyphenyl)-imidazolidin-4-one | 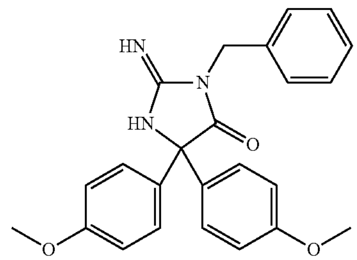 [SMILES: COc1ccc(C2(c3ccc(OC)cc3)NC(=N)N(Cc3ccccc3)C2=O)cc1] | 45 | (400 MHz, d$^6$-DMSO) δ 7.17-7.31 (m, 9H), 6.84 (d, J = 8.8 Hz, 4H), 6.60 (s, 1H), 4.70 (s, 2H), 3.71 (s, 6H) | 402.1 |
| 166 | 2-imino-5,5-bis(4-methoxyphenyl)-3-(1-methylpiperidin-4-yl)imidazolidin-4-one | 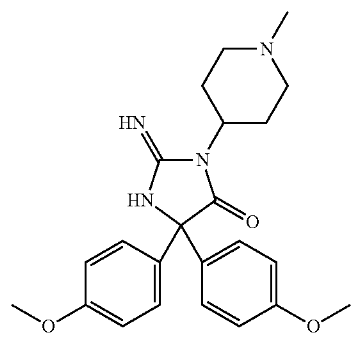 | 52 | (400 MHz, d$^6$-DMSO) δ 7.24 (d, J = 0.8 Hz, 1H), 6.83 (d, J = 0.8 Hz, 1H), 6.46 (s, 1H), 3.71 (m, 1H), 3.70 (s, 6H), 2.79 (m, 2H), 2.35 (m, 2H), 2.14 (s, 3H), 1.87 (m, 2H), 145 (m, 2H) | 409.2 |
| 167 | 3-cyclopropyl-2-imino-5,5-bis(3-methoxyphenyl)-imidazolidin-4-one | 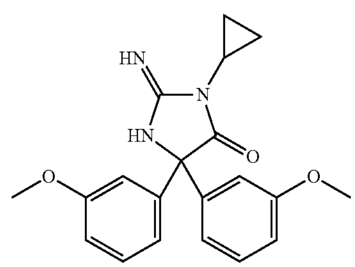 | 50 | (400 MHz, d$^6$-DMSO) δ 7.20 (t, J = 7.6, 8.0 Hz, 2H), 6.99 (d, J = 8.0 Hz, 2H), 6.95 (m, 2H), 6.79 (dd, J = 2.4, 8.0 Hz, 2H), 6.56 (s, 1H), 3.68 (s, 6H), 2.53 (m, 1H), 0.92 (m, 2H), 0.71 (m, 2H) | 352.1 |
| 168 | 3-cyclopentyl-2-imino-5,5-bis(3-methoxyphenyl)-imidazolidin-4-one | 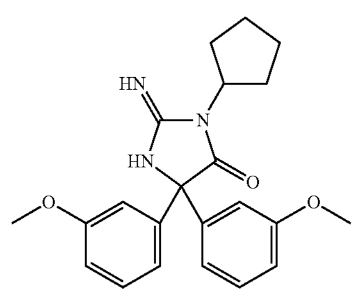 | 50 | (400 MHz, d$^6$-DMSO) δ 7.20 (m, 2H), 6.99 (m, 2H), 6.93 (s, 2H), 6.79 (m, 2H), 6.59 (s, 1H), 4.39 (m, 1H), 3.68 (s, 6H), 1.96 (m, 2H), 1.77 (m, 4H), 1.50 (m, 2H) | 380.2 |
| 171 | 3-cyclohexyl-2-imino-5-(4-methoxyphenyl)-5-[3-(pyridin-3-yl)phenyl]-imidazolidin-4-one | 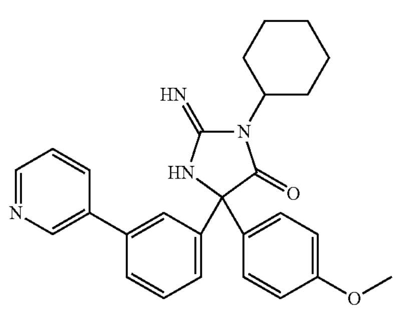 [SMILES: COc1ccc(C2(c3cccc(-c4cccnc4)c3)NC(=N)N(C3CCCCC3)C2=O)cc1] | 40 | (400 MHz, d$^6$-DMSO) δ 8.73 (s, 1H), 8.56 (d, J = 1.6 Hz, 1H), 7.92 (m, 1H), 7.65 (s, 1H), 7.58 (m, 1H), 7.44-7.50 (m, 4H), 7.31 (d, J = 8.8 Hz, 2H), 6.87 (d, J = 8.8 Hz, 2H), 3.77 (m, 1H), 3.70 (s, 3H), 2.10 (m, 2H), 1.74 (m, 2H), 1.51-1.59 (m, 3H), 1.07-1.35 (m, 3H) | 441.2 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 172 | 3-cyclohexyl-2-imino-5-(4-methoxyphenyl)-5-[3-(pyridin-4-yl)phenyl]-imidazolidin-4-one | 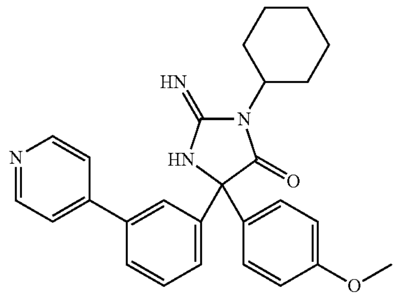 [SMILES: COc1ccc(C2(c3cccc(-c4ccncc4)c3)NC(=N)N(C3CCCCC3)C2=O)cc1] | 40 | (400 MHz, d⁶-DMSO) δ 8.63 (dd, J = 1.6 Hz, 4.8 Hz, 2H), 7.75 (s, 1H), 7.65 (d, J = 8.8 Hz, 1H), 7.44-7.56 (m, 4H), 7.30 (d, J = 8.8 Hz, 2H), 6.86 (d, J = 8.8 Hz, 2H), 6.60 (s, 1H), 3.71 (m, 1H), 3.70 (s, 3H), 2.09 (m, 2H), 1.74 (m, 2H), 1.55 (m, 3H), 1.10-1.30 (m, 3H) | 441.2 |
| 173 | 3-cyclohexyl-5,5-bis(3,4-dimethoxyphenyl)-2-imino-imidazolidin-4-one | 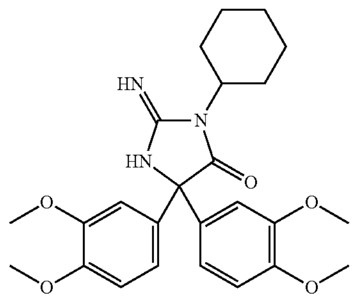 | 40 | (400 MHz, d⁶-DMSO) δ 6.84-6.93 (m, 6H), 6.51 (s, 1H), 3.63-3.71 (m, 13H), 2.11 (m, 2H), 1.74 (m, 2H), 1.52-1.60 (m, 3H), 1.05-1.30 (m, 3H) | 454.2 |
| 176 | 2-imino-5,5-bis(4-methoxyphenyl)-3-(oxan-4-yl)-imidazolidin-4-one | 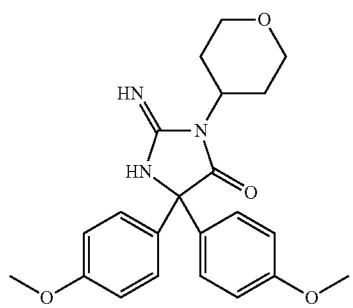 | 50 | (400 MHz, d⁶-DMSO) δ 7.25 (d, J = 8.0 Hz, 1H), 6.83 (d, J = 8.4 Hz, 1H), 6.52 (s, 1H), 3.91 (m, 3H), 3.70 (s, 6H), 3.26 (m, 2H), 2.34 (m, 2H), 1.87 (m, 2H), 147 (m, 2H) | 396.1 |
| 177 | 3-cyclohexyl-2-imino-5-(4-methoxyphenyl)-5-(3-phenylphenyl)-imidazolidin-4-one | 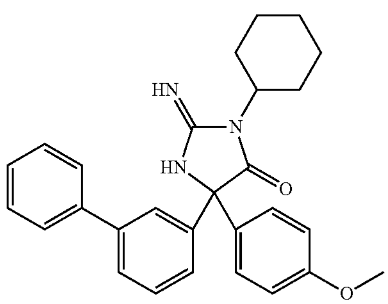 [SMILES: COc1ccc(C2(c3cccc(-c4ccccc4)c3)NC(=N)N(C3CCCCC3)C2=O)cc1] | 45 | (400 MHz, d⁶-DMSO) δ 7.63 (s, 1H), 7.30-7.52 (m, 10H), 6.86 (d, J = 8.4 Hz, 2H), 6.55 (s, 1H), 3.71 (m, 4H), 2.10 (m, 2H), 1.75 (m, 2H), 1.51-1.59 (m, 3H), 1.07-1.35 (m, 3H) | 440.2 |
| 198 | 2-imino-3-(oxan-4-yl)-5,5-diphenyl-imidazolidin-4-one | 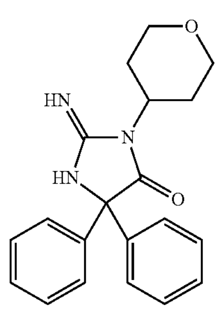 [SMILES: N=C1NC(c2ccccc2)(c2ccccc2)C(=O)N1C1CCOCC1] | 45 | (400 MHz, d⁶-DMSO) δ 7.30 (d, J = 8.0 Hz, 2H), 6.84 (d, J = 8.0 Hz, 2H), 6.48 (s, 1H), 3.71 (s, 6H), 3.30 (s, 2H), 0.82 (s, 9H) | 336.1 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 201 | 3-cyclohexyl-2-imino-5,5-bis[4-(trifluoromethoxy)phenyl]imidazolidin-4-one | 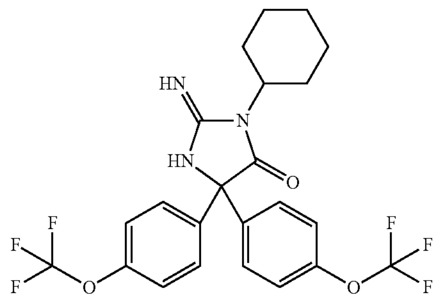 [SMILES: N=C1NC(c2ccc(OC(F)(F)F)cc2)(c2ccc(OC(F)(F)F)cc2)C(=O)N1C1CCCCC1] | 50 | (400 MHz, d⁶-DMSO) δ 7.42-7.46 (m, 4H), 7.26-7.31 (m, 4H), 6.83 (s, 1H), 3.72 (m, 1H), 2.06 (m, 2H), 1.74 (m, 2H), 1.56 (m, 3H), 1.10-1.30 (m, 3H) | 502.1 |
| 202 | 5,5-bis(2-chlorophenyl)-3-cyclohexyl-2-iminoimidazolidin-4-one | 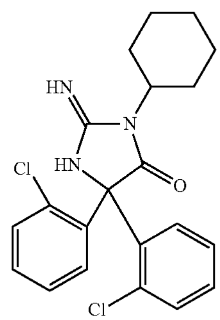 [SMILES: N=C1NC(c2ccccc2Cl)(c2ccccc2Cl)C(=O)N1C1CCCCC1] | 50 | (400 MHz, d⁶-DMSO) δ 7.26-7.56 (m, 8H), 3.56 (m, 1H), 1.83 (m, 2H), 1.71 (m, 2H), 1.55-1.58 (m, 1H), 1.10-1.33 (m, 5H) | 402.1 |
| 203 | 2-imino-5,5-bis(4-methoxyphenyl)-3-(pyridin-4-ylmethyl)-imidazolidin-4-one | 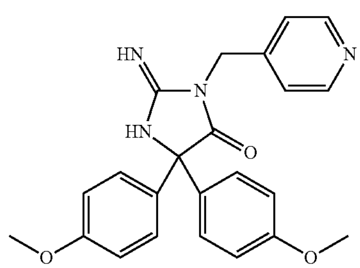 [SMILES: COc1ccc(C2(c3ccc(OC)cc3)NC(=N)N(Cc3ccncc3)C2=O)cc1] | 50 | (400 MHz, d⁶-DMSO) δ 8.49 (dd, J = 1.6, 4.4 Hz, 2H), 7.30 (d, J = 8.4 Hz, 4H), 7.11 (m, 2H), 6.86 (d, J = 8.4 Hz, 4H), 6.68 (s, 1H), 4.75 (s, 2H), 3.72 (s, 6H) | 403.1 |
| 204 | 3-cyclobutyl-2-imino-5,5-bis(4-methoxyphenyl)-imidazolidin-4-one | 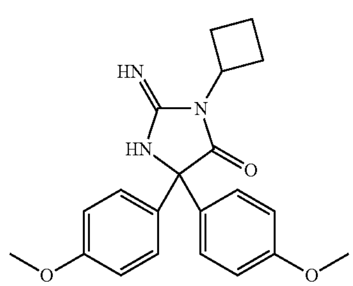 | 55 | (400 MHz, d⁶-DMSO) δ 7.27 (d, J = 8.8 Hz, 4H), 6.85 (d, J = 8.8 Hz, 4H), 6.44 (s, 1H), 4.38 (m, 1H), 3.71 (s, 6H), 2.77 (m, 2H), 2.10 (m, 2H), 1.55-1.77 (m, 2H) | 366.1 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 206 | tert-butyl 4-[2-imino-4,4-bis(4-methoxyphenyl)-5-oxoimidazolidin-1-yl]piperidine-1-carboxylate | 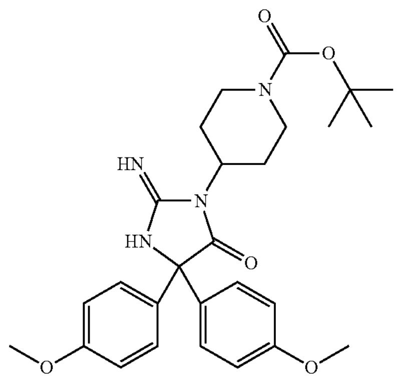 [SMILES: COc1ccc(C2(c3ccc(OC)cc3)NC(=N)N(C3CCN(C(=O)OC(C)(C)C)CC3)C2=O)cc1] | 55 | (400 MHz, d⁶-DMSO) δ 7.23 (d, J = 8.4 Hz, 1H), 6.83 (d, J = 8.4 Hz, 1H), 6.52 (s, 1H), 4.02 (m, 2H), 3.86 (m, 1H), 3.70 (s, 6H), 2.70 (m, 2H), 2.14 (m, 2H), 1.52 (m, 2H), 1.40 (s, 9H) | 495.2 |
| 207 | 2-imino-5,5-bis(4-methoxyphenyl)-3-(piperidin-4-yl)-imidazolidin-4-one | 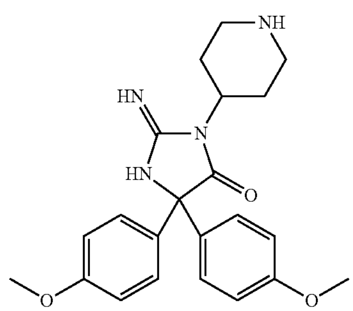 | ~50 | ¹H NMR (d⁶-DMSO, 400 MHz) δ 7.24 (d, J = 8.0 Hz, 4H), 6.84 (d, J = 8.0 Hz, 4H), 6.47 (s, 1H), 3.71 (s, 7H), 2.95 (m, 2H), 2.23 (t, J = 8.0 Hz, 2H), 2.16 (m, 2H), 1.43 (m, 2H) | 395.1 |
| 210 | 3-cyclohexyl-2-imino-5-(4-methoxyphenyl)-5-[3-(pyridin-2-yl)-phenyl]imidazolidin-4-one | 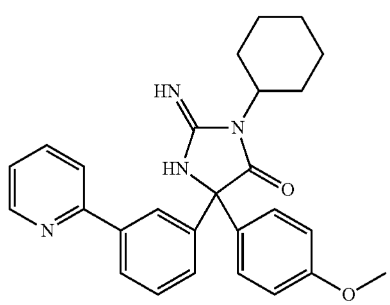 | 48 | (400 MHz, d⁶-DMSO) δ 8.64 (d, J = 4.4 Hz, 1H), 8.17 (s, 1H), 7.82-7.87 (m, 3H), 7.29-7.34 (m, 5H), 6.86 (d, J = 8.0 Hz, 2H), 6.55 (s, 1H), 3.71 (m, 4H), 2.10 (m, 2H), 1.74 (m, 2H), 1.51-1.59 (m, 3H), 1.07-1.35 (m, 3H) | 441.2 |
| 211 | 3-cyclohexyl-2-imino-5-phenyl-5-[3-(pyridin-4-yl)phenyl]-imidazolidin-4-one | 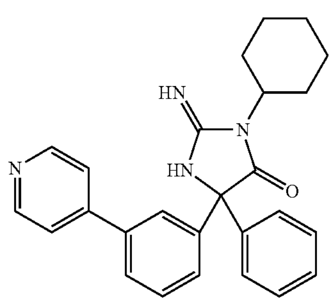 [SMILES: N=C1NC(c2ccccc2)(c2cccc(-c3ccncc3)c2)C(=O)N1C1CCCCC1] | 45 | (400 MHz, d⁶-DMSO) δ 8.63 (dd, J = 1.6, 4.4 Hz, 2H), 7.78 (s, 1H), 7.65 (m, 1H), 7.53 (m, 3H), 7.46 (m, 1H), 7.40 (m, 2H), 7.30 (m, 2H), 7.22 (m, 1H), 6.62 (s, 1H), 3.71 (m, 1H), 2.08 (m, 2H), 1.74 (m, 2H), 1.57 (m, 3H), 1.11-1.31 (m, 3H) | 411.2 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 212 | 3-cyclohexyl-2-imino-5-phenyl-5-(3-phenylphenyl)-imidazolidin-4-one | 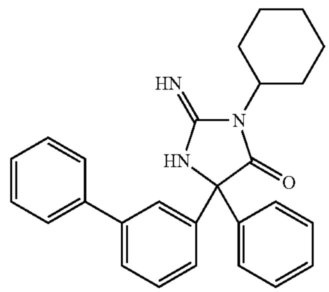 [SMILES: N=C1NC(c2ccccc2)(c2cccc(-c3ccccc3)c2)C(=O)N1C1CCCCC1] | 42 | (400 MHz, d$^6$-DMSO) δ 7.52 (s, 1H), 7.20-7.50 (m, 13H), 6.60 (m, 1H), 3.70 (m, 1H), 2.09 (m, 2H), 1.74 (m, 2H), 1.55 (m, 3H), 1.10-1.30 (m, 3H) | 410.2 |
| 214 | 3-cyclohexyl-2-imino-5-(3-methoxyphenyl)-5-[3-(pyridin-3-yl)phenyl]-imidazolidin-4-one | 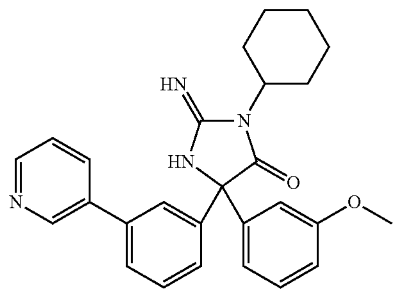 [SMILES: COc1cccc(C2(c3cccc(-c4cccnc4)c3)NC(=N)N(C3CCCCC3)C2=O)c1] | 40 | (400 MHz, d$^6$-DMSO) δ 8.74 (s, 1H), 8.57 (d, J = 3.6 Hz, 1H), 7.92 (d, J = 8.0 Hz, 1H), 7.68 (s, 1H), 7.58 (d, J = 6.8 Hz, 1H), 7.44-7.50 (m, 3H), 7.22 (t, J = 7.6, 8.0 Hz, 1H), 7.02 (d, J = 7.6 Hz, 1H), 6.97 (s, 1H), 6.81 (m, 1H), 6.63 (s, 1H), 3.71 (m, 1H), 3.68 (s, 3H), 2.10 (m, 2H), 1.74 (m, 2H), 1.55 (m, 3H), 1.10-1.30 (m, 3H) | 441.2 |
| 219 | 2-imino-5,5-bis(4-methoxyphenyl)-3-(pyridin-3-ylmethyl)-imidazolidin-4-one | 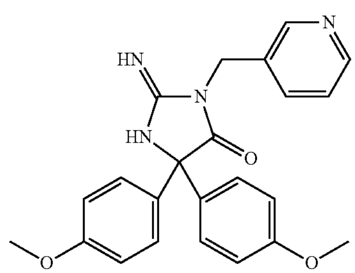 [SMILES: COc1ccc(C2(c3ccc(OC)cc3)NC(=N)N(Cc3cccnc3)C2=O)cc1] | 45 | (400 MHz, d$^6$-DMSO) δ 8.42-8.46 (m, 2H), 7.56 (m, 1H), 7.27-7.35 (m, 5H), 6.85 (d, J = 8.4 Hz, 4H), 6.70 (s, 1H), 4.75 (s, 2H), 3.71 (s, 6H) | 403.1 |
| 220 | 3-cycloheptyl-2-imino-5,5-bis(4-methoxyphenyl)-imidazolidin-4-one | 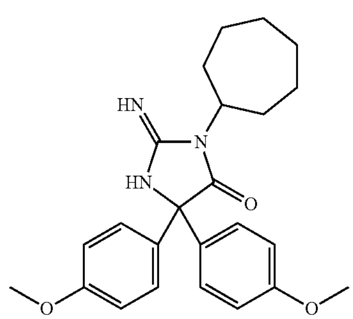 | 52 | (400 MHz, d$^6$-DMSO) δ 7.23 (d, J = 8.8 Hz, 4H), 6.85 (d, J = 8.8 Hz, 4H), 3.89 (m, 1H), 3.71 (s, 6H), 2.11 (m, 2H), 1.39-1.70 (m, 10H) | 408.2 |
| 221 | 3-(cyclohexylmethyl)-2-imino-5,5-bis(4-methoxyphenyl)-imidazolidin-4-one | 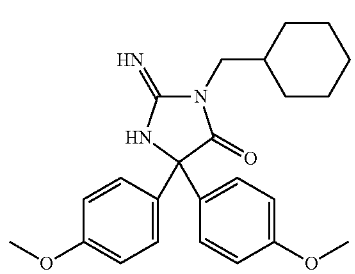 [SMILES: COc1ccc(C2(c3ccc(OC)cc3)NC(=N)N(CC3CCCCC3)C2=O)cc1] | 50 | (400 MHz, d$^6$-DMSO) δ 7.28 (d, J = 8.4 Hz, 4H), 6.83 (d, J = 8.4 Hz, 4H), 6.53 (s, 1H), 3.70 (s, 6H), 3.28-3.36 (m, 2H), 1.60 (m, 4H), 1.49 (m, 2H), 1.09 (m, 2H), 0.88 (m, 2H). | 408.2 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 223 | 2-imino-5,5-bis(4-methoxyphenyl)-3-(naphthalen-1-ylmethyl)-imidazolidin-4-one | 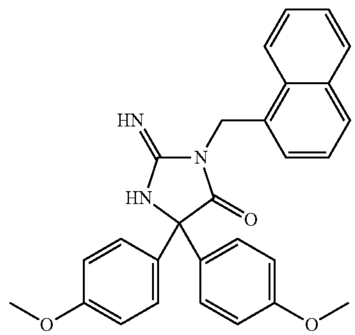 [SMILES: COc1ccc(C2(c3ccc(OC)cc3)NC(=N)N(Cc3cccc4ccccc34)C2=O)cc1] | 52 | (400 MHz, d$^6$-DMSO) δ 8.12 (d, J = 8.4 Hz, 1H), 7.96 (m, 1H), 7.83 (d, J = 8.4 Hz, 1H), 7.55-7.60 (m, 2H), 7.37 (m, 5H), 6.88 (m, 5H), 6.61 (s, 1H), 5.21 (s, 2H), 3.73 (s, 6H). | 452.1 |
| 225 | 3-cyclohexyl-2-imino-5-(3-methoxyphenyl)-5-[3-(pyridin-4-yl)phenyl]imidazolidin-4-one | 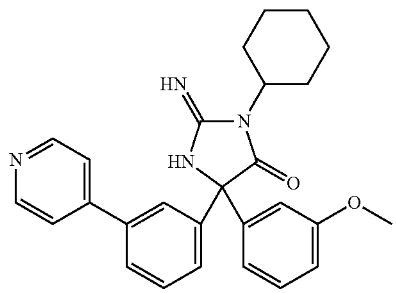 [SMILES: COc1cccc(C2(c3cccc(-c4ccncc4)c3)NC(=N)N(C3CCCCC3)C2=O)c1] | 45 | (400 MHz, d$^6$-DMSO) δ 8.63 (d, J = 6.0 Hz, 2H), 7.78 (s, 1H), 7.65 (d, J = 7.6 Hz, 1H), 7.54 (d, J = 6.0 Hz, 3H), 7.46 (t, J = 7.6 Hz, 1H), 7.22 (t, J = 8.0 Hz, 1H), 7.01 (d, J = 8.0 Hz, 1H), 6.96 (d, J = 2.0 Hz, 1H), 6.81 (dd, J = 2.4, 8.0 Hz, 1H), 6.65 (s, 1H), 3.71 (m, 1H), 3.68 (s, 3H), 2.08-2.11 (m, 2H), 1.75 (m, 2H), 1.51-1.59 (m, 3H), 1.07-1.35 (m, 3H) | 441.2 |
| 227 | 3-cyclohexyl-2-imino-5-(3-methoxyphenyl)-5-[3-(pyridin-2-yl)phenyl]-imidazolidin-4-one | 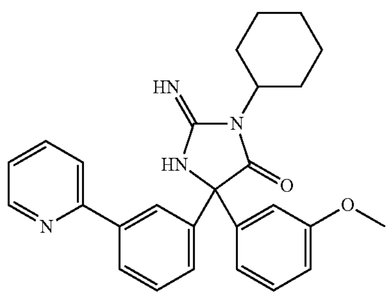 [SMILES: COc1cccc(C2(c3cccc(-c4ccccn4)c3)NC(=N)N(C3CCCCC3)C2=O)c1] | 40 | (400 MHz, d$^6$-DMSO) δ 8.64 (m, 1H), 8.21 (s, 1H), 7.83-7.89 (m, 3H), 7.50 (d, J = 8.0 Hz, 1H), 7.41 (m, 1H), 7.34 (m, 1H), 7.21 (m, 1H), 7.00 (d, J = 8.0 Hz, 1H), 6.96 (m, 1H), 6.81 (m, 1H), 6.63 (s, 1H), 3.71 (m, 1H), 3.68 (s, 3H), 2.11 (m, 2H), 1.73 (m, 2H), 1.55 (m, 3H), 1.07-1.30 (m, 3H) | 441.2 |
| 228 | 5-[3-(benzyloxy)-phenyl]-3-cyclohexyl-2-imino-5-phenylimidazolidin-4-one | 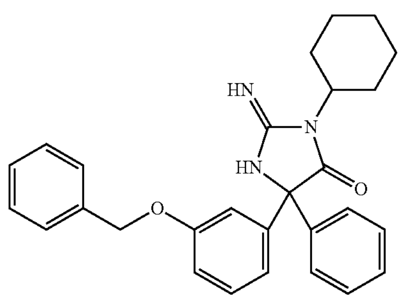 [SMILES: N=C1NC(c2ccccc2)(c2cccc(OCc3ccccc3)c2)C(=O)N1C1CCCCC1] | 42 | (400 MHz, d$^6$-DMSO) δ 7.20-7.39 (m, 12H), 6.93 (d, J = 8.0 Hz, 2H), 6.52 (s, 1H), 5.05 (s, 2H), 3.69 (m, 1H), 2.07-2.10 (m, 2H), 1.73-1.76 (m, 2H), 1.51-1.59 (m, 3H), 1.07-1.35 (m, 3H) | 440.2 |
| 229 | 2-imino-5,5-bis(4-methoxyphenyl)-3-(pyridin-2-ylmethyl)-imidazolidin-4-one | 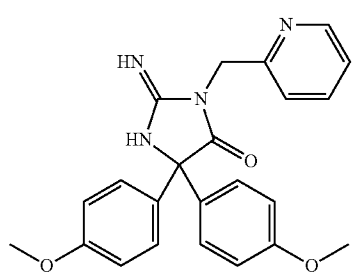 [SMILES: COc1ccc(C2(c3ccc(OC)cc3)NC(=N)N(Cc3ccccn3)C2=O)cc1] | 50 | (400 MHz, d$^6$-DMSO) δ 8.50 (m, 1H), 7.75 (m, 1H), 7.26-7.33 (m, 5H), 7.13 (m, 1H), 6.85 (d, J = 8.0 Hz, 4H), 6.55 (s, 1H), 4.80 (s, 2H), 3.72 (s, 6H) | 403.1 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 230 | 5-[3-(benzyloxy)-phenyl]-3-cyclohexyl]-2-imino-5-(3-methoxyphenyl)-imidazolidin-4-one | 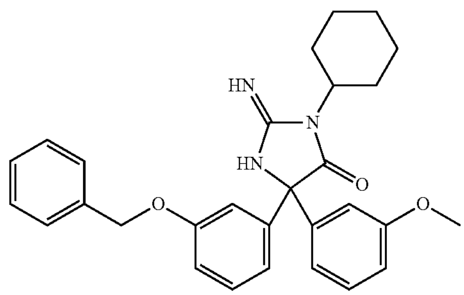 [SMILES: COc1cccc(C2(c3cccc(OCc4ccccc4)c3)NC(=N)N(C3CCCCC3)C2=O)c1] | 48 | (400 MHz, d$^6$-DMSO) δ 7.19-7.38 (m, 9H), 6.90-6.95 (m, 4H), 6.79-6.81 (m, 1H), 5.05 (s, 2H), 3.72 (m, 1H), 3.68 (s, 3H), 2.07-2.10 (m, 2H), 1.74 (m, 2H), 1.55 (m, 3H), 1.11-1.31 (m, 3H) | 470.2 |
| 231 | 2-imino-5,5-bis(4-methoxyphenyl)-3-[(4-methylphenyl)-methyl]imidazolidin-4-one | 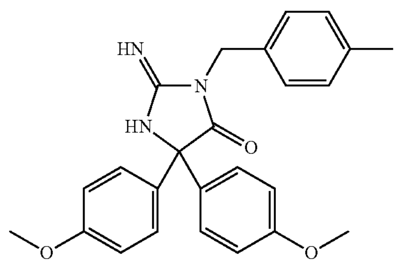 | 55 | (400 MHz, d$^6$-DMSO) δ 7.29 (d, J = 8.0 Hz, 4H), 7.09 (s, 4H), 6.84 (d, J = 8.4 Hz, 4H), 6.59 (s, 1H), 4.65 (s, 2H), 3.71 (s, 6H), 2.24 (s, 3H) | 416.1 |
| 232 | 3-[(4-chlorophenyl)-methyl]-2-imino-5,5-bis(4-methoxyphenyl)-imidazolidin-4-one | 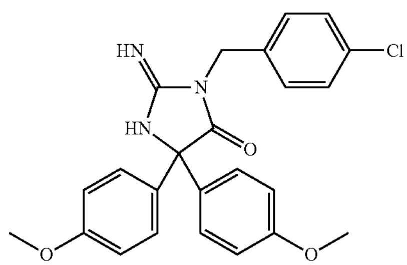 [SMILES: COc1ccc(C2(c3ccc(OC)cc3)NC(=N)N(Cc3ccc(Cl)cc3)C2=O)cc1] | 55 | (400 MHz, d$^6$-DMSO) δ 7.37 (m, 2H), 7.20-7.28 (m, 6H), 6.84 (m, 4H), 6.65 (s, 1H), 4.69 (s, 2H), 3.71 (s, 6H). | 436.1 |
| 233 | 2-imino-5,5-bis(4-methoxyphenyl)-3-[(4-methoxyphenyl)-methyl]imidazolidin-4-one | 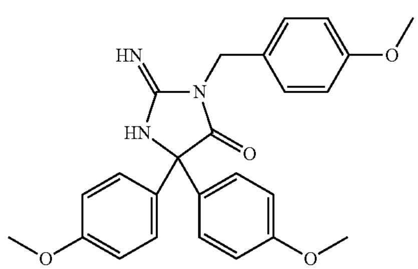 | 53 | (400 MHz, d$^6$-DMSO) δ 7.27 (m, 4H), 7.15 (m, 2H), 6.82-6.86 (m, 6H), 6.60 (s, 1H), 4.62 (s, 2H), 3.70 (s, 9H). | 432.1 |
| 234 | 3-[(2-chlorophenyl)-methyl]-2-imino-5,5-bis(4-methoxyphenyl)-imidazolidin-4-one | 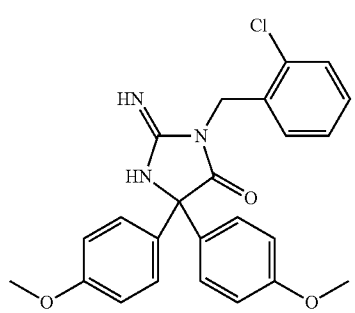 [SMILES: COc1ccc(C2(c3ccc(OC)cc3)NC(=N)N(Cc3ccccc3Cl)C2=O)cc1] | 45 | (400 MHz, d$^6$-DMSO) δ 7.48 (m, 1H), 7.22-7.34 (m, 6H), 6.86 (d, J = 8.8 Hz, 4H), 6.77 (m, 1H), 6.67 (s, 1H), 4.78 (s, 2H), 3.72 (s, 6H) | 436.1 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 235 | 3-[(3-chlorophenyl)-methyl]-2-imino-5,5-bis(4-methoxyphenyl)-imidazolidin-4-one | 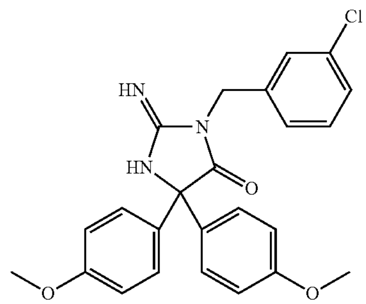 [SMILES: COc1ccc(C2(c3ccc(OC)cc3)NC(=N)N(Cc3cccc(Cl)c3)C2=O)cc1] | 45 | (400 MHz, d$^6$-DMSO) δ 7.27-7.36 (m, 6H), 7.20 (s, 1H), 7.13 (m, 1H), 6.85 (d, J = 8.8 Hz, 4H), 6.67 (s, 1H), 4.71 (s, 2H), 3.71 (s, 6H) | 436.1 |
| 236 | 2-imino-5,5-bis(4-methoxyphenyl)-3-[(3-methoxyphenyl)-methyl]imidazolidin-4-one | 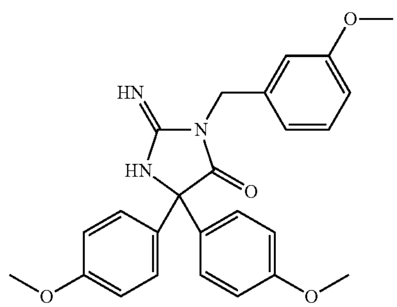 | 48 | (400 MHz, d$^6$-DMSO), δ 7.31 (d, J = 8.8 Hz, 4H), 7.19 (m, 1H), 6.84 (d, J = 8.8 Hz, 4H), 6.74-6.80 (m, 2H), 6.68 (s, 1H), 6.59 (s, 1H), 4.68 (s, 2H), 3.71 (s, 6H), 3.59 (s, 3H) | 432.1 |
| 237 | 3-cyclohexyl-2-imino-5,5-bis(3-methylphenyl)-imidazolidin-4-one | 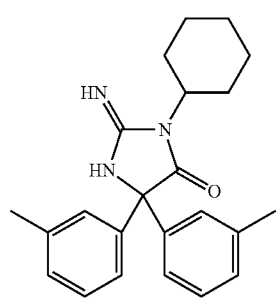 | 48 | (400 MHz, d$^6$-DMSO) δ 7.02-7.17 (m, 8H), 6.51 (s, 1H), 3.71 (m, 1H), 2.24 (s, 6H), 2.09 (m, 2H), 1.74 (m, 2H), 1.53 (m, 3H), 1.10-1.30 (m, 3H) | 362.2 |
| 238 | 3-cyclohexyl-2-imino-5-(3-phenoxyphenyl)-5-phenylimidazolidin-4-one | 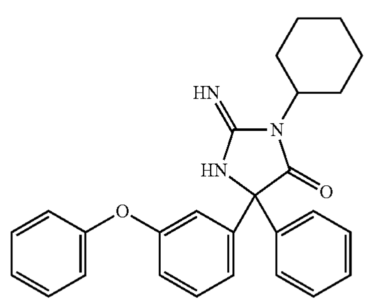 [SMILES: N=C1NC(c2ccccc2)(c2cccc(Oc3ccccc3)c2)C(=O)N1C1CCCCC1] | 43 | (400 MHz, d$^6$-DMSO) δ 7.35-7.38 (m, 6H), 7.29 (m, 2H), 7.12-7.27 (m, 2H), 6.99 (d, J = 7.6 Hz, 2H), 6.93 (d, J = 8.4 Hz, 2H), 6.56 (s, 1H), 3.68 (m, 1H), 2.07 (m, 2H), 1.73 (m, 2H), 1.56 (m, 3H), 1.07-1.31 (m, 3H) | 462.2 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 248 | 2-imino-5,5-bis(4-methoxyphenyl)-3-[(2-methoxyphenyl)-methyl]imidazolidin-4-one | 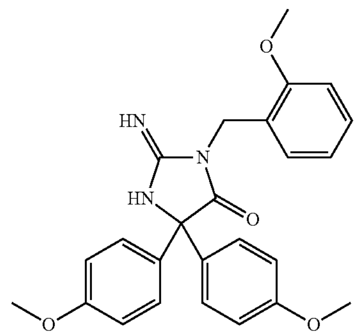 [SMILES: COc1ccc(C2(c3ccc(OC)cc3)NC(=N)N(Cc3ccccc3OC)C2=O)cc1] | 38 | (400 MHz, d⁶-DMSO) δ 7.31 (d, J = 8.8 Hz, 4H), 7.22 (m, 1H), 6.99 (m, 1H), 6.75-6.86 (m, 6H), 6.50 (s, 1H), 4.65 (s, 2H), 3.78 (s, 3H), 3.71 (s, 6H) | 432.1 |
| 249 | 2-imino-5,5-bis(4-methoxyphenyl)-3-{[3-(trifluoromethyl)-phenyl]methyl}imidazolidin-4-one | 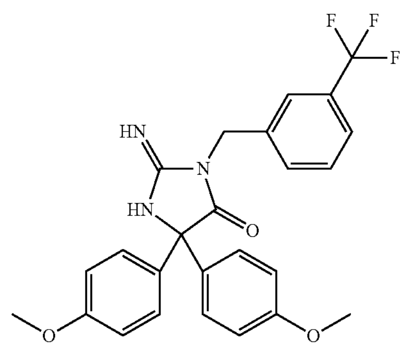 [SMILES: COc1ccc(C2(c3ccc(OC)cc3)NC(=N)N(Cc3cccc(C(F)(F)F)c3)C2=O)cc1] | 46 | (400 MHz, d⁶-DMSO) δ 7.62 (m, 1H), 7.55 (m, 1H), 7.49 (m, 2H), 7.28 (d, J = 8.4 Hz, 4H), 6.84 (d, J = 8.4 Hz, 4H), 6.69 (s, 1H), 4.81 (s, 2H), 3.71 (s, 6H) | 487.1 |
| 250 | 3-(1-benzylpiperidin-4-yl)-2-imino-5,5-bis(4-methoxyphenyl)-imidazolidin-4-one | 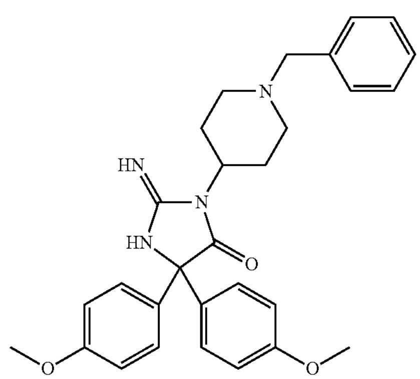 [SMILES: COc1ccc(C2(c3ccc(OC)cc3)NC(=N)N(C3CCN(Cc4ccccc4)CC3)C2=O)cc1] | 50 | (400 MHz, d⁶-DMSO) δ 7.22-7.37 (m, 10H), 6.85-6.88 (m, 4H), 4.20 (m, 2H), 3.72 (s, 6H), 3.69 (m, 1H), 3.38 (m, 2H), 2.15 (m, 1H), 2.03 (m, 1H), 1.79 (m, 2H), 1.58 (m, 1H) | 485.2 |
| 252 | 3-(2,2-dimethylpropyl)-2-imino-5,5-bis(4-methoxyphenyl)-imidazolidin-4-one | 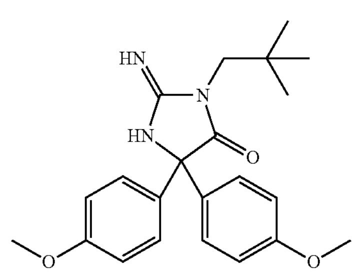 | 50 | (400 MHz, d⁶-DMSO) δ 7.30 (d, J = 8.0 Hz, 4H), 6.84 (d, J = 8.0 Hz, 4H), 6.48 (s, 1H), 3.71 (s, 6H), 3.30 (s, 2H), 0.82 (s, 9H) | 382.2 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 253 | 2-imino-5,5-bis(4-methoxyphenyl)-3-[(3-methylphenyl)methyl]imidazolidin-4-one | 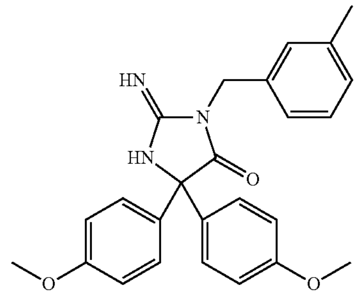 | 52 | (400 MHz, d$^6$-DMSO) δ 7.30 (d, J = 8.8 Hz, 4H), 7.17 (m, 1H), 7.04 (m, 1H), 6.97 (m, 1H), 6.92 (s, 1H), 6.85 (d, J = 8.8 Hz, 4H), 6.59 (s, 1H), 4.67 (s, 2H), 3.71 (s, 6H), 2.19 (s, 3H) | 416.1 |
| 267 | 5,5-bis(3-chlorophenyl)-3-cyclohexyl-2-iminoimidazolidin-4-one | 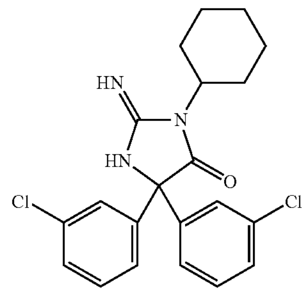 [SMILES: N=C1NC(c2cccc(Cl)c2)(c2cccc(Cl)c2)C(=O)N1C1CCCCC1] | 45 | (400 MHz, d$^6$-DMSO) δ 7.30-7.38 (m, 8H), 6.76 (s, 1H), 3.71 (m, 1H), 2.06 (m, 2H), 1.74 (m, 2H), 1.51-1.59 (m, 3H), 1.07-1.35 (m, 3H) | 402.1 |
| 269 | 3-cyclohexyl-2-imino-5,5-bis[3-(pyridin-3-yl)phenyl]imidazolidin-4-one | 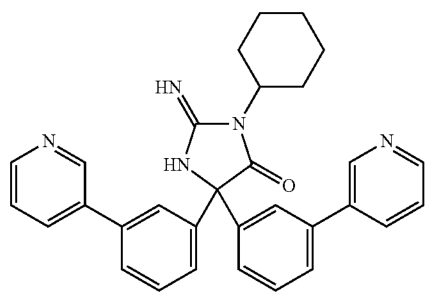 [SMILES: N=C1NC(c2cccc(-c3cccnc3)c2)(c2cccc(-c3cccnc3)c2)C(=O)N1C1CCCCC1] | 40 | (400 MHz, d$^6$-DMSO) δ 8.75 (s, 2H), 8.56 (d, J = 3.6 Hz, 2H), 7.93 (d, J = 8.0 Hz, 2H), 7.74 (s, 2H), 7.44-7.60 (m, 10H), 6.69 (s, 1H), 3.74 (m, 1H), 2.11 (m, 2H), 1.75 (m, 2H), 1.58 (m, 3H), 1.11-1.31 (m, 3H) | 488.2 |
| 272 | 3-[(2,5-dimethylphenyl)methyl]-2-imino-5,5-bis(4-methoxyphenyl)imidazolidin-4-one | 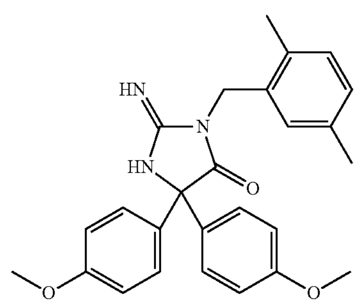 | 45 | (400 MHz, d$^6$-DMSO) δ 7.34 (d, J = 8.8 Hz, 4H), 7.03 (m, 1H), 6.92 (m, 1H), 6.86 (d, J = 8.8 Hz, 4H), 6.59 (brs, 1H), 6.39 (s, 1H), 4.63 (s, 2H), 3.72 (s, 6H), 2.22 (s, 3H), 2.01 (s, 3H). | 430.2 |
| 273 | 3-(1-cyclohexyl-2-imino-5-oxo-4-phenylimidazolidin-4-yl)-N-methylbenzamide | 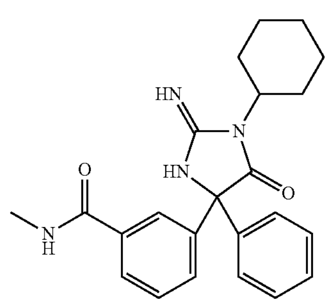 [SMILES: CNC(=O)c1cccc(C2(c3ccccc3)NC(=N)N(C3CCCCC3)C2=O)c1] | 45 | (400 MHz, d$^6$-DMSO) δ 8.37 (m, 1H), 7.90 (s, 1H), 7.66 (d, J = 8.0 Hz, 1H), 7.51 (d, J = 8.0 Hz, 1H), 7.21-7.39 (m, 6H), 6.81 (brs, 1H), 3.74 (m, 1H), 2.74 (d, J = 4.4 Hz,, 3H), 2.04-2.13 (m, 2H), 1.74 (m, 2H), 1.55 (m, 3H), 1.07-1.31 (m, 3H) | 391.2 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 274 | 2-imino-5,5-bis(4-methoxyphenyl)-3-(oxolan-2-ylmethyl)-imidazolidin-4-one | 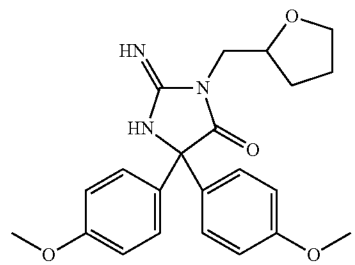 | 50 | (400 MHz, d⁶-DMSO) δ 7.26-7.29 (m, 4H), 6.84 (d, J = 8.0 Hz, 4H), 6.43 (s, 1H), 4.0 (m, 1H), 3.75 (m, 1H), 3.70 (s, 6H), 3.61 (m, 1H), 3.52 (m, 2H), 1.74-1.84 (m, 3H), 1.48 (m, 1H) | 396.1 |
| 275 | 2-imino-5,5-bis(4-methoxyphenyl)-3-(oxan-4-ylmethyl)imidazolidin-4-one | 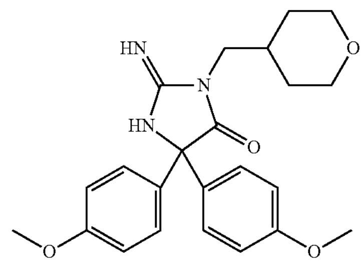 [SMILES: COc1ccc(C2(c3ccc(OC)cc3)NC(=N)N(CC3CCOCC3)C2=O)cc1] | 52 | (400 MHz, d⁶-DMSO) δ 7.29 (d, J = 8.8 Hz, 4H), 6.84 (d, J = 8.4 Hz, 4H), 6.58 (s, 1H), 3.78 (m, 2H), 3.70 (s, 6H), 3.35 (m, 2H), 3.17 (m, 2H), 1.83 (s, 1H), 1.37 (m, 2H), 1.11-1.21 (m, 2H) | 410.2 |
| 276 | 3-(adamantan-1-ylmethyl)-2-imino-5,5-bis(4-methoxyphenyl)-imidazolidin-4-one | 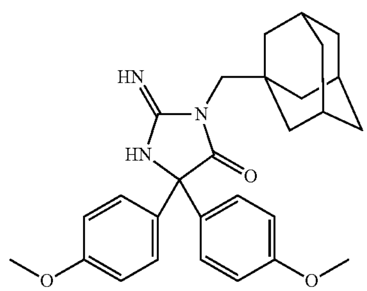 [SMILES: COc1ccc(C2(c3ccc(OC)cc3)NC(=N)N(CC34CC5CC(CC(C5)C3)C4)C2=O)cc1] | 50 | (400 MHz, d⁶-DMSO) δ 7.29 (d, J = 8.8 Hz, 4H), 6.84 (d, J = 8.4 Hz, 4H), 6.43 (s, 1H), 3.73 (s, 6H), 3.17 (s, 2H), 1.86 (s, 3H), 1.60 (m, 3H), 1.40-1.51 (m, 9H) | 460.2 |
| 277 | 3-[(2,3-dimethyl-phenyl)methyl]-2-imino-5,5-bis(4-methoxyphenyl)-imidazolidin-4-one | 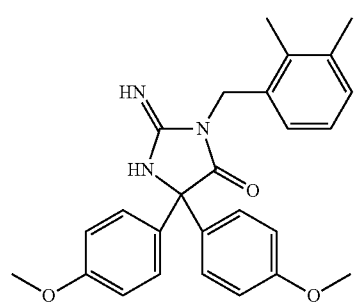 | 50 | (400 MHz, d⁶-DMSO) δ 7.34 (d, J = 8.4 Hz, 4H), 7.03 (m, 1H), 6.86-6.92 (m, 5H), 6.49-6.52 (m, 2H), 4.68 (s, 2H), 3.72 (s, 6H), 2.24 (s, 3H), 2.16 (s, 3H) | 430.2 |
| 278 | 3-[(2,6-dimethyl-phenyl)methyl]-2-imino-5,5-bis(4-methoxyphenyl)-imidazolidin-4-one | 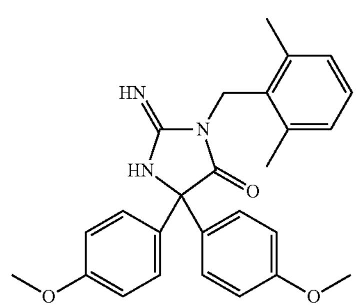 [SMILES: COc1ccc(C2(c3ccc(OC)cc3)NC(=N)N(Cc3c(C)cccc3C)C2=O)cc1] | 50 | (400 MHz, d⁶-DMSO) δ 7.21 (d, J = 8.8 Hz, 4H), 7.04 (m, 1H), 6.95 (m, 2H), 6.82 (m, 4H), 6.48 (s, 1H), 4.68 (s, 2H), 3.70 (s, 6H), 2.23 (s, 6H) | 430.2 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
|---|---|---|---|---|---|
| 302 | 2-imino-5,5-bis(4-methoxyphenyl)-3-[(3-methylpyridin-2-yl)methyl]imidazolidin-4-one | 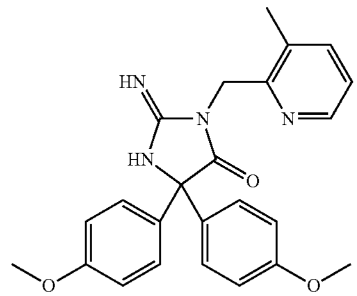 [SMILES: COc1ccc(C2(c3ccc(OC)cc3)NC(=N)N(Cc3ncccc3C)C2=O)cc1] | 55 | (400 MHz, d$^6$-DMSO) δ 8.27 (m, 1H), 7.59 (m, 1H), 7.34-7.37 (m, 4H), 7.19-7.22 (m, 1H), 6.85 (d, J = 8.4 Hz, 4H), 6.42 (s, 1H), 4.77 (s, 2H), 3.72 (s, 6H), 2.32 (s, 3H) | 417.1 |
| 303 | 2-imino-5,5-bis(4-methoxyphenyl)-3-[(2-methylphenyl)-methyl]imidazolidin-4-one | 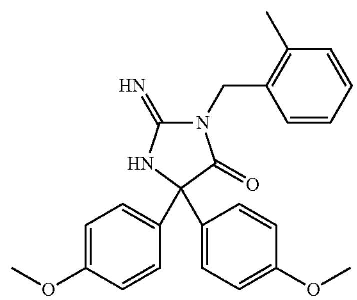 [SMILES: COc1ccc(C2(c3ccc(OC)cc3)NC(=N)N(Cc3ccccc3C)C2=O)cc1] | 55 | (400 MHz, d$^6$-DMSO) δ 7.34 (d, J = 8.8 Hz, 4H), 7.11-7.24 (m, 2H), 7.00-7.04 (m, 1H), 6.87 (d, J = 8.8 Hz, 4H), 6.66 (m, 1H), 6.57 (s, 1H), 4.67 (s, 2H), 3.75 (s, 6H), 2.28 (s, 2H) | 416.1 |
| 304 | 2-imino-5,5-bis(4-methoxyphenyl)-3-{[2-(trifluoromethyl)-phenyl]methyl}-imidazolidin-4-one | 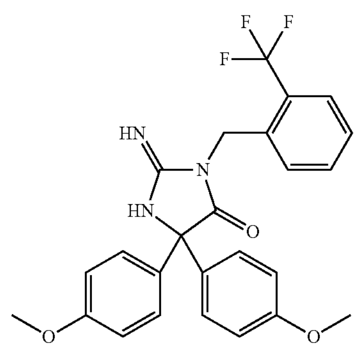 [SMILES: COc1ccc(C2(c3ccc(OC)cc3)NC(=N)N(Cc3ccccc3C(F)(F)F)C2=O)cc1] | 52 | (400 MHz, d$^6$-DMSO) δ 7.74 (m, 1H), 7.55 (m, 1H), 7.46 (m, 1H), 7.31 (d, J = 8.8 Hz, 4H), 6.92 (m, 1H), 6.86 (d, J = 8.4 Hz, 4H), 6.73 (s, 1H), 4.91 (s, 2H), 3.71 (s, 6H). | 470.1 |
| 306 | 3-[(2-fluorophenyl)-methyl]-2-imino-5,5-bis(4-methoxyphenyl)-imidazolidin-4-one | 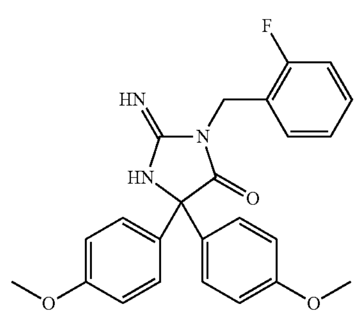 [SMILES: COc1ccc(C2(c3ccc(OC)cc3)NC(=N)N(Cc3ccccc3F)C2=O)cc1] | 50 | (400 MHz, d$^6$-DMSO) δ 7.30 (m, 5H), 7.19 (m, 1H), 7.09 (m, 1H), 6.95 (m, 1H), 6.85 (d, J = 8.8 Hz, 4H), 6.63 (s, 1H), 4.78 (s, 2H), 3.71 (s, 6H) | 420.1 |

| Ex. | IUPAC Name | Structure | Yield (%) | ¹H NMR | LC-MS m/z (M + H) |
|---|---|---|---|---|---|
| 307 | 3-[(2-bromophenyl)-methyl]-2-imino-5,5-bis(4-methoxy-phenyl)imidazolidin-4-one | 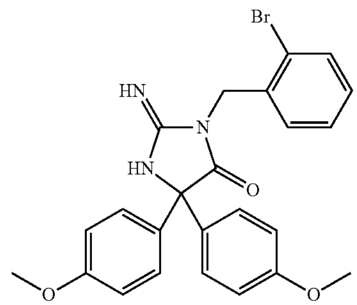 [SMILES: COc1ccc(C2(c3ccc(OC)cc3)NC(=N)N(Cc3ccccc3Br)C2=O)cc1] | 50 | (400 MHz, d⁶-DMSO) δ 7.65 (d, J = 8.8 Hz, 1H), 7.33 (d, J = 8.8 Hz, 4H), 7.20-7.28 (m, 2H), 6.87 (d, J = 8.8 Hz, 4H), 6.68-6.73 (m, 2H), 4.72 (s, 2H), 3.72 (s, 6H), | 480.1 |
| 308 | 2-imino-5,5-bis(4-methoxyphenyl)-3-[(1-methylpiperidin-4-yl)methyl]imidazolidin-4-one | 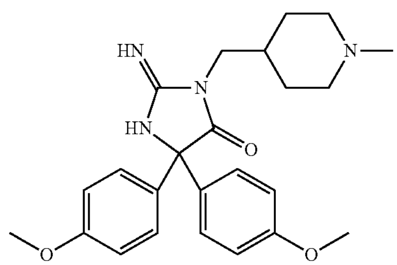 | 50 | (400 MHz, d⁶-DMSO) δ 7.28 (d, J = 8.4 Hz, 4H), 6.83 (d, J = 8.4 Hz, 4H), 6.54 (s, 1H), 3.70 (s, 6H), 2.67 (m, 2H), 2.08 (s, 3H), 1.69 (m, 2H), 1.53 (m, 1H), 1.41 (m, 2H), 1.07-1.17 (m, 2H) | 423.2 |
| 313 | tert-butyl 4-{[2-imino-4,4-bis(4-methoxyphenyl)-5-oxoimidazolidin-1-yl]methyl}piperidine-1-carboxylate | 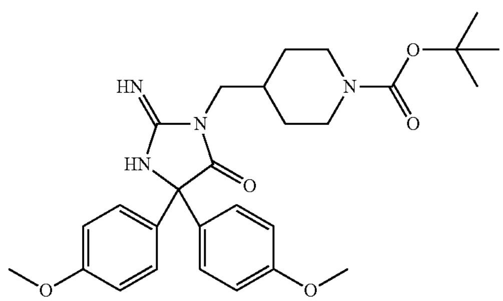 [SMILES: COc1ccc(C2(c3ccc(OC)cc3)NC(=N)N(CC3CCN(C(=O)OC(C)(C)C)CC3)C2=O)cc1] | 45 | (400 MHz, d⁶-DMSO) δ 7.28 (d, J = 8.8 Hz, 4H), 6.83 (d, J = 8.4 Hz, 4H), 6.57 (s, 1H), 3.86 (m, 2H), 3.70 (s, 6H), 2.54 (m, 2H), 1.78 (m, 1H), 1.43 (m, 2H), 1.37 (s, 9H), 0.97-1.00 (m, 2H). | 509.2 |
| 323 | 2-imino-5-(4-methoxyphenyl)-3-(oxan-4-yl)-5-(pyridin-3-yl)imidazolidin-4-one | 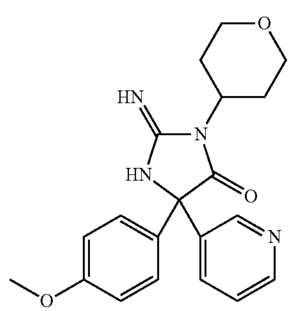 [SMILES: COc1ccc(C2(c3cccnc3)NC(=N)N(C3CCOCC3)C2=O)cc1] | 45 | (400 MHz, d⁶-DMSO) δ 8.54 (s, 1H), 8.43 (m, 1H), 7.71 (m, 1H), 7.33 (m, 1H), 7.28 (d, J = 8.4 Hz, 1H), 6.88 (d, J = 8.8 Hz, 2H), 6.70 (s, 1H), 3.91 (m, 3H), 3.72 (s, 3H), 3.29 (m, 2H), 2.35 (m, 2H), 1.50 (m, 2H) | 367.1 |
| 324 | 2-imino-5-[3-(3-methoxyphenyl)-phenyl]-3-(oxan-4-yl)-5-phenylimidazolidin-4-one | 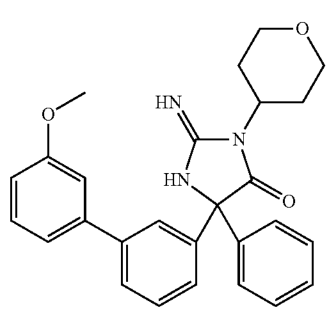 [SMILES: COc1cccc(-c2cccc(C3(c4ccccc4)NC(=N)N(C4CCOCC4)C3=O)c2)c1] | 48 | (400 MHz, d⁶-DMSO) δ 7.65 (s, 1H), 7.52 (m, 1H), 7.23-7.43 (m, 8H), 7.04-7.09 (m, 2H), 6.95 (m, 1H), 6.67 (s, 1H), 3.89-4.04 (m, 3H), 3.80 (s, 3H), 2.35 (m, 2H), 1.51 (m, 2H) | 442.2 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 325 | 5-cyclopropyl-2-imino-5-(4-methoxyphenyl)-3-(oxan-4-yl)imidazolidin-4-one | 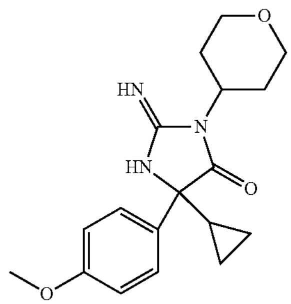 [SMILES: COc1ccc(C2(C3CC3)NC(=N)N(C3CCOCC3)C2=O)cc1] | 40 | (400 MHz, d⁶-DMSO) δ 7.43 (d, J = 8.0 Hz, 2H), 6.88 (m, 2H), 6.43 (s, 1H), 3.89 (m, 3H), 3.73 (s, 3H), 3.25 (m, 2H), 2.32 (m, 2H), 1.44 (m, 3H), 0.33 (m, 3H), 0.09 (m, 1H) | 330.1 |
| 326 | 3-cyclohexyl-2-imino-5-[3-(3-methoxyphenyl)phenyl]-5-phenylimidazolidin-4-one | 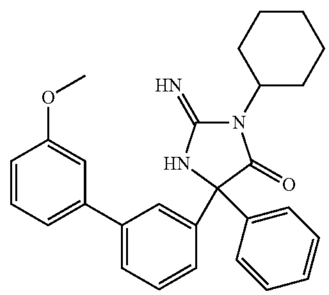 [SMILES: COc1cccc(-c2cccc(C3(c4ccccc4)NC(=N)N(C4CCCCC4)C3=O)c2)c1] | 56 | (400 MHz, d⁶-DMSO) δ 7.63 (s, 1H), 7.52 (m, 1H), 7.21-7.44 (m, 8H), 7.07 (d, J = 8.0 Hz, 1H), 7.04 (m, 1H), 6.93 (m, 1H), 6.62 (s, 1H), 3.80 (s, 3H), 3.75 (m, 1H), 2.11 (m, 2H), 1.74 (m, 2H), 1.55 (m, 3H), 1.08-1.28 (m, 3H) | 440.2 |
| 327 | 2-imino-5-[3-(3-methoxyphenyl)phenyl]-3-methyl-5-phenyl-imidazolidin-4-one | 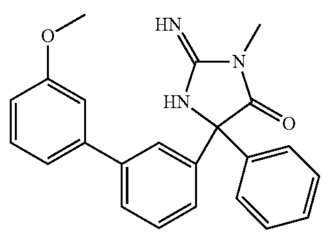 [SMILES: COc1cccc(-c2cccc(C3(c4ccccc4)NC(=N)N(C)C3=O)c2)c1] | 50 | (400 MHz, d⁶-DMSO) δ 7.72 (s, 1H), 7.32-7.52 (m, 6H), 7.31 (m, 2H), 7.21 (m, 1H), 7.04-7.10 (m, 2H), 6.95 (m, 1H), 6.69 (s, 1H), 3.80 (s, 3H), 3.00 (s, 3H) | 372.1 |
| 328 | 3-cyclohexyl-5-cyclopropyl-2-imino-5-[3-(3-methoxyphenyl)-phenyl]imidazolidin-4-one | 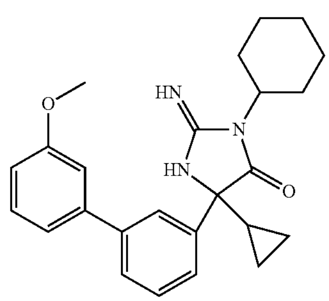 [SMILES: COc1cccc(-c2cccc(C3(C4CC4)NC(=N)N(C4CCCCC4)C3=O)c2)c1] | 46 | (400 MHz, d⁶-DMSO) δ 7.79 (s, 1H), 7.56 (m, 2H), 7.39 (m, 2H), 7.15 (d, J = 8.8 Hz, 1H), 7.10 (s, 1H), 6.95 (m, 1H), 6.47 (s, 1H), 3.81 (s, 3H), 3.64 (m, 1H), 2.07 (m, 2H), 1.74 (m, 2H), 1.53 (m, 4H), 1.09-1.28 (m, 3H), 0.41 (m, 3H), 0.14 (m, 1H) | 404.2 |
| 329 | 5-cyclopropyl-2-imino-5-[3-(3-methoxyphenyl)-phenyl]-3-(oxan-4-yl)imidazolidin-4-one | 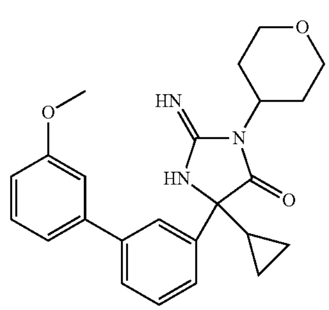 [SMILES: COc1cccc(-c2cccc(C3(C4CC4)NC(=N)N(C4CCOCC4)C3=O)c2)c1] | 43 | (400 MHz, d⁶-DMSO) δ 7.81 (s, 1H), 7.38-7.59 (m, 4H), 7.14 (m, 2H), 6.95 (m, 1H), 6.53 (s, 1H), 3.91 (m, 3H), 3.82 (s, 3H), 3.25 (m, 2H), 2.36 (m, 2H), 1.46 (m, 3H), 0.32-0.42 (m, 3H), 0.15 (s, 1H) | 406.2 |

TABLE 3-continued

Examples 100 to 336.
This table includes both compounds of the present invention as well as comparison compounds.

| Ex. | IUPAC Name | Structure | Yield (%) | ¹H NMR | LC-MS m/z (M + H) |
|---|---|---|---|---|---|
| 330 | 5-cyclopropyl-2-imino-5-[3-(3-methoxyphenyl)-phenyl]-3-methyl-imidazolidin-4-one | 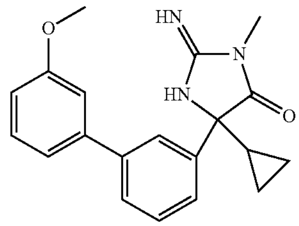 [SMILES: COc1cccc(-c2cccc(C3(C4CC4)NC(=N)N(C)C3=O)c2)c1] | 30 | (400 MHz, d⁶-DMSO) δ 7.83 (s, 1H), 7.60 (d, J = 8.0 Hz, 2H), 7.53 (d, J = 8.0 Hz, 2H), 7.37-7.42 (m, 2H), 7.15 (d, J = 7.6 Hz, 1H), 6.96 (dd, J = 2.0, 8.0 Hz, 1H), 6.59 (s, 1H), 3.82 (s, 3H), 2.93 (s, 3H), 1.54 (m, 1H), 0.42 (m, 1H), 0.32 (m, 2H), 0.17 (m, 1H) | 336.1 |
| 331 | 5-cyclohexyl-2-imino-5-(4-methoxy-phenyl)-3-(oxan-4-yl)imidazolidin-4-one | 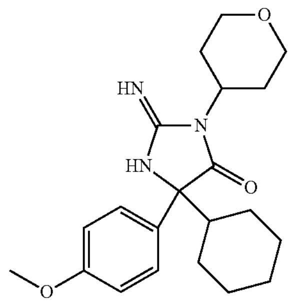 [SMILES: COc1ccc(C2(C3CCCCC3)NC(=N)N(C3CCOCC3)C2=O)cc1] | 48 | (400 MHz, d⁶-DMSO) δ 7.43 (d, J = 8.8 Hz, 2H), 6.87 (d, J = 8.4 Hz, 2H), 3.83-3.90 (m, 3H), 3.22-3.27 (m, 2H), 2.32 (m, 2H), 0.97-1.67 (m, 13H) | 372.2 |
| 332 | 2-imino-5-(4-methoxyphenyl)-3-(oxan-4-yl)-5-(pyridin-2-yl)-imidazolidin-4-one | 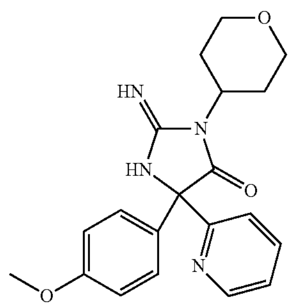 [SMILES: COc1ccc(C2(c3ccccn3)NC(=N)N(C3CCOCC3)C2=O)cc1] | 55 | (400 MHz, d⁶-DMSO) δ 8.48 (s, 1H), 7.69 (m, 1H), 7.45 (d, J = 7.6 Hz, 2H), 7.24 (m, 1H), 6.92 (m, 1H), 6.91 (d, J = 8.8 Hz, 2H), 6.52 (s, 1H), 3.87-4.01 (m, 3H), 3.74 (s, 3H), 2.38-2.47 (m, 2H), 1.43-1.55 (m, 2H) | 367.1 |
| 333 | 2-imino-5-(4-methoxyphenyl)-3-(oxan-4-yl)-5-(pyrimidin-5-yl)imidazolidin-4-one | 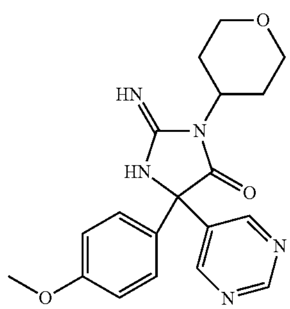 [SMILES: COc1ccc(C2(c3cncnc3)NC(=N)N(C3CCOCC3)C2=O)cc1] | 47 | (400 MHz, d⁶-DMSO) δ 9.08 (s, 1H), 8.73 (s, 2H), 7.29 (d, J = 8.8 Hz, 2H), 6.90 (d, J = 8.8 Hz, 2H), 6.83 (s, 1H), 3.88-3.97 (m, 3H), 3.73 (s,, 3H), 3.26 (m, 2H), 2.33 (m, 2H), 1.52 (m, 2H) | 368.1 |
| 334 | 2-imino-5-(4-methoxyphenyl)-3-(oxan-4-yl)-5-(pyridin-4-yl)-imidazolidin-4-one | 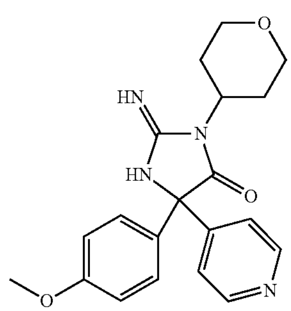 [SMILES: COc1ccc(C2(c3ccncc3)NC(=N)N(C3CCOCC3)C2=O)cc1] | 48 | (400 MHz, d⁶-DMSO) δ 8.49 (d, J = 7.2 Hz, 1H), 7.29-7.35 (m, 4H), 6.88 (d, J = 8.8 Hz, 2H), 6.73 (s, 1H), 3.91 (m, 3H), 3.71 (s,, 3H), 3.71 (m, 2H), 2.34 (m, 2H), 1.49 (m, 2H) | 367.1 |

TABLE 3-continued

Examples 100 to 336.
This table includes both compounds of the present invention as well as comparison compounds.

| Ex. | IUPAC Name | Structure | Yield (%) | $^1$H NMR | LC-MS m/z (M + H) |
| --- | --- | --- | --- | --- | --- |
| 335 | 5-cyclopentyl-2-imino-5-(4-methoxy-phenyl)-3-(oxan-4-yl)imidazolidin-4-one | 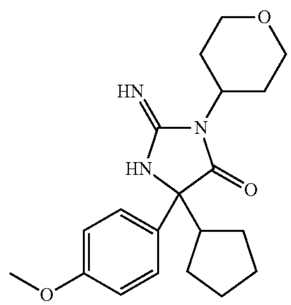 [SMILES: COc1ccc(C2(C3CCCC3)NC(=N)N(C3CCOCC3)C2=O)cc1] | 46 | (400 MHz, d$^6$-DMSO) δ 7.46 (m, 2H), 6.85 (m, 2H), 6.45 (s, 1H), 3.86 (m, 3H), 3.72 (s, 3H), 3.22-3.28 (m, 2H), 2.32 (m, 2H), 0.99-1.43 (m, 11H) | 358.2 |
| 336 | 2-imino-5-(4-methoxyphenyl)-5-(1-methyl-1H-pyrazol-4-yl)-3-(oxan-4-yl)-imidazolidin-4-one | 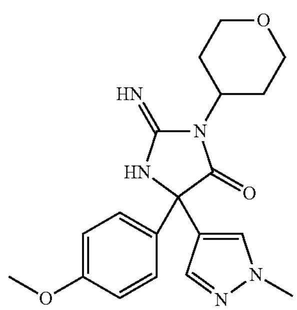 | 42 | (400 MHz, d$^6$-DMSO) δ 7.49 (s, 1H), 7.27 (m, 2H), 7.23 (s, 1H), 6.85 (d, J = 8.8 Hz, 2H), 6.52 (brs, 1H), 3.88-3.95 (m, 3H), 3.78 (s,, 3H), 3.72 (s, 3H), 3.29 (m, 2H), 2.33 (m, 2H), 1.47 (m, 2H) | 370.1 |

Examples 310, 311 and 322

Preparation of N-Acylated Examples

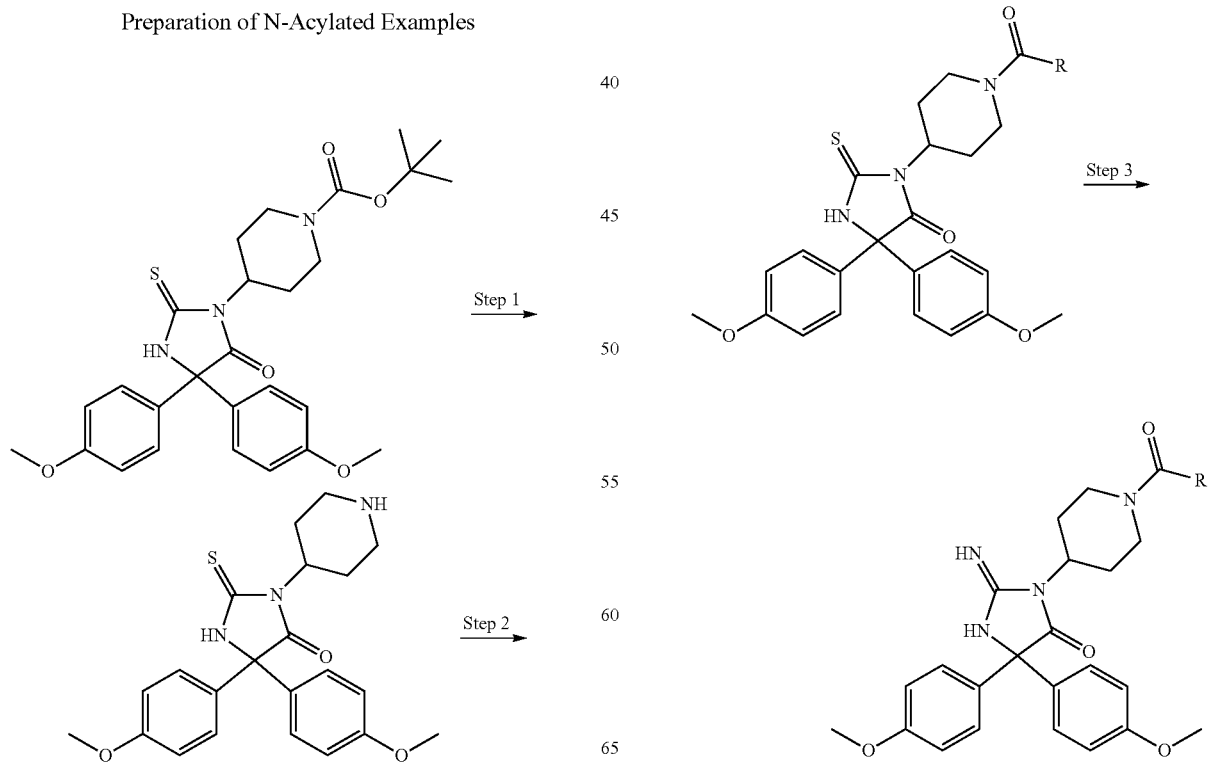

Step 1. Preparation of 5,5-bis(4-methoxyphenyl)-3-(piperidin-4-yl)-2-thioxoimidazolidin-4-one

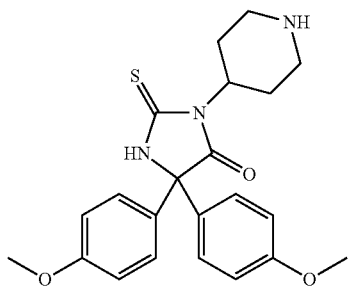

tert-Butyl 4-(4,4-b is (4-methoxyphenyl)-5-oxo-2-thioxo imidazolidin-1-yl)piperidine-1-carboxylate (prepared as an intermediate in the synthesis of 206; 5 g, 9.77 mmol) was dissolved in 30 mL DCM. 30 mL TFA was added and the reaction was stirred for 2 h at room temperature. Then, the solvent was evaporated to provide the TFA salt of the title compound as a residue that was used without further purification.

Step 2. Preparation of N-Acylated Thioxoimidazolidine Intermediates

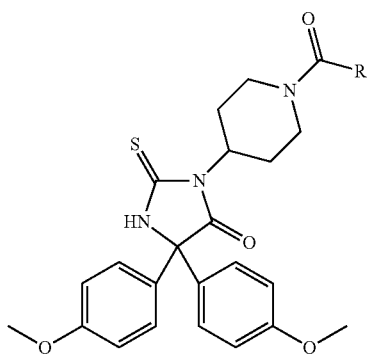

5,5-bis(4-methoxyphenyl)-3-(piperidin-4-yl)-2-thioxoimidazolidin-4-one trifluoroacetate (1.0 equiv) and triethylamine (2.0 equiv.) were dissolved in DCM at 0° C., and corresponding acyl chloride (1.5 equiv.) was added drop wise. Then the reaction was raised to room temperature and stirred overnight. The mixture was extracted with DCM and the combined organic phases were washed with water, dried over sodium sulfate and concentrated in vacuo to give the acylated intermediates which were used without further purification.

Step 3. Preparation of N-Acylated Examples

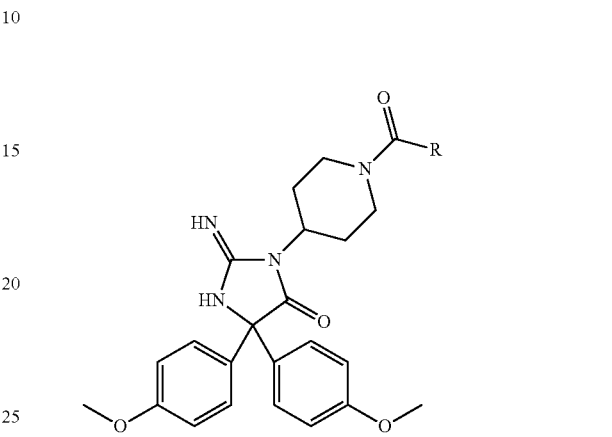

To a solution of the N-acylated intermediate from Step 2 in methanol was added aqueous ammonium (25%, 20 equiv) and tert-butyl hydroperoxide (70%, 16 equiv) separately, and the resulting solution was stirred at room temperature overnight. The mixture was extracted with dichloromethane and the organic layer was concentrated in vacuo. The residue was purified over a silica column to give the final purified N-acylated compounds as shown in Table 4.

TABLE 4

Examples 310, 311 and 322.

| Ex. | IUPAC Name | Structure | Yield (%) | $^1$H NMR | LC-MS m/z (M + H) |
|---|---|---|---|---|---|
| 310 | 3-(1-acetylpiperidin-4-yl)-2-imino-5,5-bis(4-methoxyphenyl)imidazolidin-4-one | | 50 | (400 MHz, d$^6$-DMSO) δ 7.25 (d, J = 8.8 Hz, 4H), 6.83 (d, J = 8.8 Hz, 4H), 6.54 (s, 1H), 4.48 (m, 1H), 3.86-3.99 (m, 2H), 3.70 (s, 6H), 2.99 (m, 1H), 2.42 (m, 1H), 2.07-2.23 (m, 2H), 2.00 (s, 3H), 1.55 (m, 2H) | 437.2 |
| 311 | 3-(1-benzoylpiperidin-4-yl)-2-imino-5,5-bis(4-methoxyphenyl)imidazolidin-4-one | | 50 | (400 MHz, d$^6$-DMSO) δ 7.39-7.49 (m, 5H), 7.20-7.29 (m, 4H), 6.82-6.93 (m, 4H), 6.56 (s, 1H), 4.59 (s, 1H), 4.02 (m, 1H), 3.73 (s, 6H), 3.70 (m, 1H), 3.03 (m, 1H), 2.74 (m, 1H), 2.24(m, 2H), 1.55-1.64 (m, 2H). | 499.2 |
| 322 | 3-{1-[3-(dimethylamino)propanoyl]piperidin-4-yl}-2-imino-5,5-bis(4-methoxyphenyl)imidazolidin-4-one | | 15 | (400 MHz, d$^6$-DMSO) δ 7.24 (d, J = 8.0 Hz, 4H), 6.84 (m, 4H), 6.53 (s, 1H), 4.49 (m, 1H), 3.96 (m, 2H), 3.71 (s, 6H), 2.97 (m, 1H), 2.45 (s, 4H), 2.13 (s, 6H), 1.56 (m, 2H) | 494.2 |

Example 305

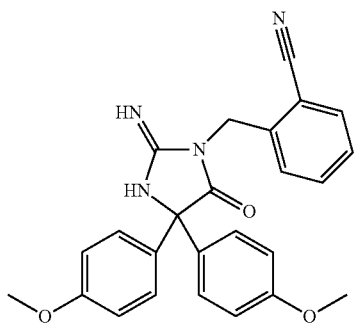 [SMILES: COc1ccc(C2(c3ccc(OC)cc3)NC(=N)N(Cc3ccccc3C#N)C2=O)cc1]

Preparation of 2-{[2-imino-4,4-bis(4-methoxyphenyl)-5-oxoimidazolidin-1-yl]methyl}benzonitrile 3-[(2-bromophenyl)methyl]-2-imino-5,5-bis(4-methoxyphenyl)imidazolidin-4-one (Example 307; 0.1 g, 0.21 mmol) was dissolved in dioxane, then zinc cyanide (48 mg, 0.41 mmol), bis(dibenzylideneacetone)palladium (12.0 mg, 0.02 mmol) and X-PHOS (4.9 mg, 0.01 mmol) were added. The reaction was heated at 150° C. for 2 h in a microwave reactor. The mixture was extracted with DCM and the organic layer was dried in vacuo. The residue was purified by HPLC to give the title compound as a white solid (20 mg, 22% yield). $^1$H NMR (400 MHz, CDCl$_3$) δ 7.67 (m, 1H), 7.53 (m, 1H), 7.32-7.42 (m, 6H), 6.85 (d, J=8.8 Hz, 4H), 4.98 (s, 2H), 3.79 (s, 6H). LC-MS m/z 427.1 (M+H).

Examples 389 and 390

Preparation of O-Alkylated Examples

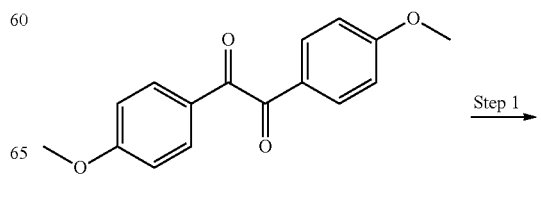

Step 1

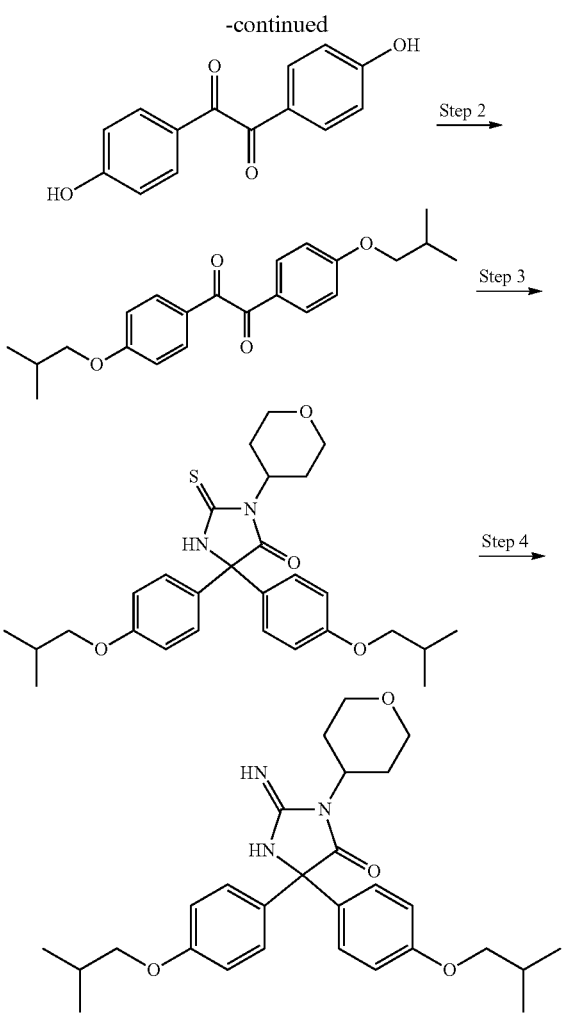

Step 1. Preparation of
1,2-bis(4-hydroxyphenyl)ethane-1,2-dione

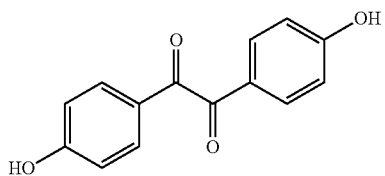 [SMILES: O=C(C(=O)c1ccc(O)cc1)c1ccc(O)cc1]

4,4'-dimethoxybenzil (2.0 g, 7.41 mmol) was dissolved in 30 mL of hydrogen bromide and 10 mL of acetic acid glacial. The reaction was stirred at reflux temperature overnight. The mixture was extracted with ethyl acetate and the organic phase was washed with water, dried over sodium sulphate. Concentration under vaccum gave the title compound as a yellow solid (1.9 g, quantitative).

Step 2. Preparation of
1,2-bis(4-isobutoxyphenyl)ethane-1,2-dione

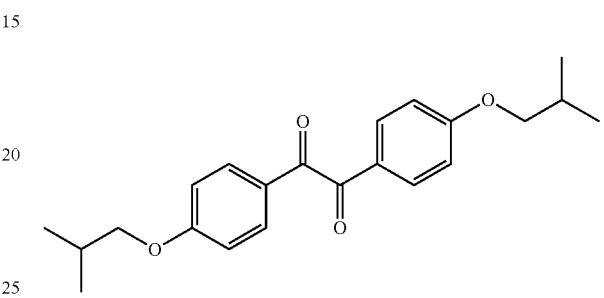

1,2-Bis(4-hydroxyphenyl)ethane-1,2-dione (0.77 g, 3.18 mmol) was dissolved in 20 mL of DMF. Potassium carbonate (1.3 g, 9.4 mmol), tetrabutylammonium bromide (0.5 g, 1.55 mmol) and 1-bromo-2-methylpropane (0.86 mL, 7.91 mmol) were added, then the reaction was stirred at 130° C. overnight. The mixture was extracted with ethyl acetate and the organic phase was washed with water, dried over sodium sulfate. Concentration under vacuum gave the title compound as oil (1.2 g, quantitative).

Step 3. Preparation of O-Alkylated Examples

Aminohydantoins 389 and 390 (Table 5) were prepared according to the procedure for 117 from the corresponding thiourea Intermediate A2 and corresponding dione (1,2-bis(4-isobutoxyphenyl)ethane-1,2-dione from Step 2 or 1,2-bis(3-isobutoxyphenyl)ethane-1,2-dione prepared in a similar manner).

TABLE 5

Examples 389 and 390.

| Ex. | IUPAC Name | Structure | Yield (%) | $^1$H NMR | LC-MS m/z (M + H) |
|---|---|---|---|---|---|
| 389 | 2-imino-5,5-bis[3-(2-methylpropoxy)phenyl]-3-(oxan-4-yl)imidazolidin-4-one | 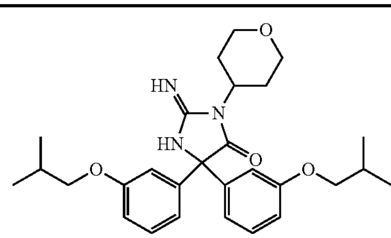 | 40% (four steps) | $^1$H NMR (d$^6$-DMSO, 400 MHz) δ 7.19 (t, J = 7.6, 8.0 Hz, 2H), 6.97 (d, J = 8.0 Hz, 2H), 6.92 (s, 2H), 6.79 (d, J = 8.0 Hz, 2H), 6.63 (s, 1H), 3.90 (m, 3H), 3.65 (d, J = 6.4 Hz, 4H), 3.29 (m, 2H), 2.35 (m, 2H), 1.97 (m, 2H), 1.47 (m, 2H), 0.95 (m, 12H) | 480.2 |

TABLE 5-continued

Examples 389 and 390.

| Ex. | IUPAC Name | Structure | Yield (%) | ¹H NMR | LC-MS m/z (M + H) |
|---|---|---|---|---|---|
| 390 | 2-imino-5,5-bis[4-(2-methylpropoxy)phenyl]-3-(oxan-4-yl)imidazolidin-4-one | 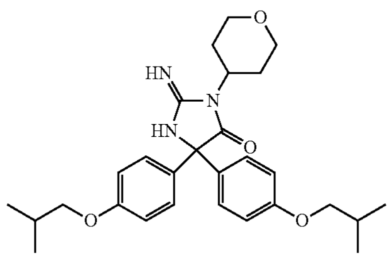 [SMILES: CC(C)COc1ccc(C2(c3ccc(OCC(C)C)cc3)NC(=N)N(C3CCOCC3)C2=O)cc1] | 40% (four steps) | ¹H NMR (d⁶-DMSO, 500 MHz) δ 7.23 (d, J = 8.0 Hz, 4H), 6.83 (d, J = 8.0 Hz, 4H), 6.53 (s, 1H), 3.91 (m, 3H), 3.65 (d, J = 6.5 Hz, 4H), 3.29 (m, 2H), 2.35 (m, 2H), 1.98 (m, 2H), 1.46 (m, 2H), 0.95 (m, 12H) | 480.2 |

Examples 270 and 404 to 577

Preparation of Aminohydantoins 270 and 404 to 577

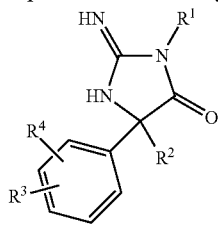

Aminohydantoins 270 and 404 to 577 (Table 6) were prepared according to the procedure for 117 from the corresponding thiourea Intermediates A1-A39 and corresponding dione (Intermediates B1-B45 or commercially available diones). For 404, 412, 564, 567 and 568, the corresponding dione was prepared by demethylation and alkylation of the dione precursor by a manner similar to that described for Example 389.

TABLE 6

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 270 | 2-imino-5,5-bis(4-methoxyphenyl)-3-(4-methylcyclohexyl)imidazolidin-4-one | 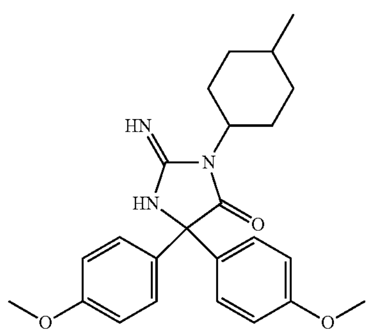 | ¹H NMR (400 MHz, d⁶-DMSO) δ 7.24 (d, J = 6.0 Hz, 4H), 6.83 (d, J = 7.6 Hz, 4H), 6.44 (s, 1H), 3.71 (s, 6H), 3.65 (m, 1H), 3.38 (m, 2H), 2.14 (m, 1H), 1.70 (m, 1H), 0.85-2.33 (m, 12H) | 408.2 |
| 404 | 2-imino-5-(3-isobutoxyphenyl)-5-(3-(pyridin-3-yl)phenyl)-3-(tetrahydro-2H-pyran-4-yl)imidazolidin-4-one | 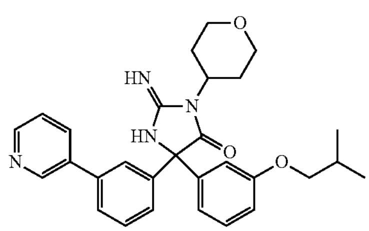 [SMILES: CC(C)COc1cccc(C2(c3cccc(-c4cccnc4)c3)NC(=N)N(C3CCOCC3)C2=O)c1] | ¹H NMR (400 MHz, d⁶-DMSO) 8.75 (s, 1H), 8.57 (dd, J = 1.2, 4.8 Hz, 1H), 7.92 (d, J = 8.0 Hz, 1H), 7.68 (s, 1H), 7.59 (d, J = 6.8 Hz, 1H), 7.44-7.51 (m, 3H), 7.21 (t, J = 8.0 Hz, 1H), 7.03 (d, J = 7.6 Hz, 1H), 6.98 (s, 1H), 6.80 (d, J = 7.6 Hz, 1H), 6.70 (s, 1H), 3.91 (m, 3H), 2.37 (m, 2H), 1.96 (m, 1H), 1.50 (m, 2H), 0.94 (d, J = 9.2 Hz, 6H) | 485.2 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 412 | 2-imino-5-(4-isobutoxyphenyl)-5-(3-(pyridin-3-yl)phenyl)-3-(tetrahydro-2H-pyran-4-yl)imidazolidin-4-one | 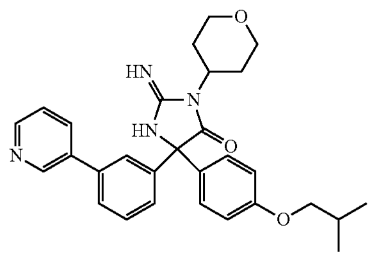 [SMILES: CC(C)COc1ccc(C2(c3cccc(-c4cccnc4)c3)NC(=N)N(C3CCOCC3)C2=O)cc1] | ¹H NMR (400 MHz, d⁶-DMSO) δ 8.74 (s, 1H), 8.57 (d, J = 3.6 Hz, 1H), 7.92 (d, J = 7.6 Hz, 1H), 7.67 (s, 1H), 7.57 (d, J = 6.0 Hz, 1H), 7.43-7.50 (m, 3H), 7.31 (d, J = 8.0 Hz, 2H), 6.85 (d, J = 8.0 Hz, 1H), 6.64 (s, 1H), 3.89-3.96 (m, 3H), 3.68 (d, J = 6.4 Hz, 2H), 2.37 (m, 2H), 2.98 (m, 1H), 1.49 (m, 2H), 0.92 (dd, J = 6.4, 18.4 Hz, 6H) | 485.2 |
| 413 | 3'-(2-imino-5-oxo-4-phenyl-1-(tetrahydro-2H-pyran-4-yl)imidazolidin-4-yl)-[1,1'-biphenyl]-3-carbonitrile | 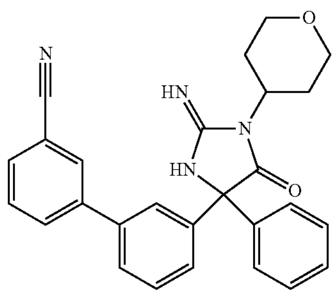 [SMILES: N#Cc1cccc(-c2cccc(C3(c4ccccc4)NC(=N)N(C4CCOCC4)C3=O)c2)c1] | ¹H NMR (400 MHz, d⁶-DMSO) δ 7.99 (s, 1H), 7.82-7.86 (m, 2H), 7.61-7.71 (m, 3H), 7.24-7.49 (m, 7H), 6.70 (m, 1H), 3.89-3.98 (m, 3H), 3.29-3.30 (m, 2H), 2.37-2.38 (m, 2H), 1.50 (d, J = 12.4 Hz, 2H) | 437.1 |
| 414 | 3'-(4-cyclopropyl-2-imino-5-oxo-1-(tetrahydro-2H-pyran-4-yl)imidazolidin-4-yl)-[1,1'-biphenyl]-3-carbonitrile | 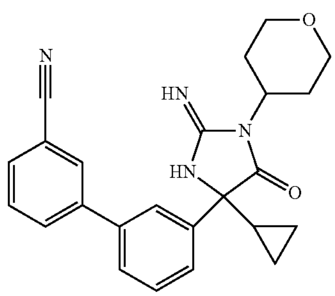 [SMILES: N#Cc1cccc(-c2cccc(C3(C4CC4)NC(=N)N(C4CCOCC4)C3=O)c2)c1] | ¹H NMR (400 MHz, d⁶-DMSO) δ 8.08 (m, 1H), 7.95 (d, J = 8.0 Hz, 1H), 7.84-7.88 (m, 2H), 7.62-7.72 (m, 3H), 7.45-7.49 (m, 1H), 6.59-6.61 (m, 1H), 3.90 (t, J = 11.2 Hz, 3H), 3.25-3.28 (m, 2H), 2.32-2.37 (m, 2H), 1.43-1.59 (m, 3H), 0.34-0.42 (m, 3H), 0.17 (m, 1H) | 401.1 |
| 447 | 3,5-dicyclohexyl-2-imino-5-(4-methoxyphenyl)imidazolidin-4-one | 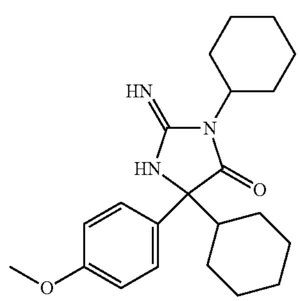 [SMILES: COc1ccc(C2(C3CCCCC3)NC(=N)N(C3CCCCC3)C2=O)cc1] | ¹H NMR (400 MHz, d⁶-DMSO) δ 7.50 (d, J = 8.8 Hz, 1H), 7.40 (d, J = 8.8 Hz, 1H), 6.90 (d, J = 8.8 Hz, 1H), 6.85 (d, J = 8.8 Hz, 1H), 3.73 ((d, J = 4.8 Hz, 3H), 1.98-2.07 (m, 2H), 0.87-1.73 (m, 15H) | 370.1 |
| 486 | 3'-(1-cyclohexyl-4-cyclopropyl-2-imino-5-oxoimidazolidin-4-yl)-[1,1'-biphenyl]-3-carbonitrile | 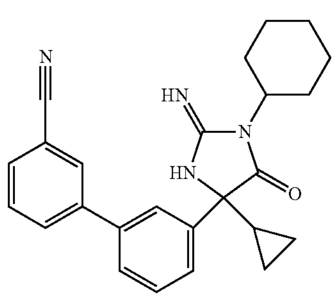 [SMILES: N#Cc1cccc(-c2cccc(C3(C4CC4)NC(=N)N(C4CCCCC4)C3=O)c2)c1] | ¹H NMR (400 MHz, d⁶-DMSO) δ 8.07 (s, 1H), 7.95 (d, J = 8.0 Hz, 1H), 7.84-7.87 (m, 2H), 7.61-7.71 (m, 3H), 7.44-7.48 (m, 1H), 6.47-6.50 (m, 1H), 3.70 (m, 1H), 2.02-2.14 (m, 2H), 1.74 (t, J = 12.8 Hz, 2H), 1.49-1.57 (m, 4H), 1.09-1.28 (m, 3H), 0.33-0.42 (m, 3H), 0.17 (s, 1H) | 399.1 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 487 | 5-cyclopropyl-2-imino-5-(3-(pyridin-3-yl)phenyl)-3-(tetrahydro-2H-pyran-4-yl)imidazolidin-4-one | 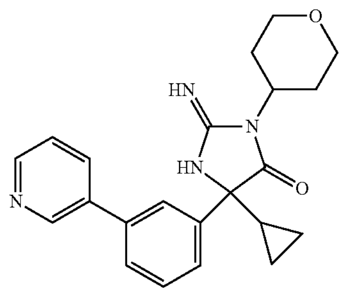 [SMILES: N=C1NC(c2cccc(-c3cccnc3)c2)(C2CC2)C(=O)N1C1CCOCC1] | ¹H NMR (400 MHz, d⁶-DMSO)) δ 8.82 (m, 1H), 8.57-8.59 (m, 1H), 8.01 (d, J = 7.6 Hz, 1H), 7.84 (s, 1H), 7.61-7.63 (m, 2H), 7.46-7.52 (m, 2H), 6.56 (s, 1H), 3.86-3.99 (m, 3H), 3.25-3.34 (m, 2H), 2.32-2.37 (m, 2H), 1.43-1.57 (m, 3H), 0.35-0.43 (m, 3H), 0.18 (s, 1H) | 377.1 |
| 488 | 5-(3-(4-cyclopropyl-2-imino-5-oxo-1-(tetrahydro-2H-pyran-4-yl)imidazolidin-4-yl)phenyl)nicotinonitrile | 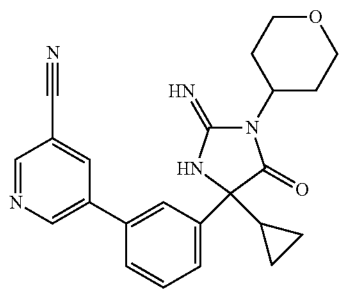 [SMILES: N#Cc1cncc(-c2cccc(C3(C4CC4)NC(=N)N(C4CCOCC4)C3=O)c2)c1] | ¹H NMR (400 MHz, d⁶-DMSO) δ 9.11 (m, 1H), 9.02 (m, 1H), 8.59 (s, 1H), 7.94 (s, 1H), 7.65-7.71 (m, 2H), 7.48-7.52 (m, 1H), 6.58 (m, 1H), 3.86-3.93 (m, 3H), 3.25-3.30 (m, 3H), 2.28-2.37 (m, 2H), 1.62 (m, 1H), 1.43-1.51 (m, 2H), 0.34-0.42 (m, 3H), 0.17 (m, 1H) | 402.1 |
| 489 | 5-(3-(5-chloropyridin-3-yl)phenyl)-5-cyclopropyl-2-imino-3-(tetrahydro-2H-pyran-4-yl)imidazolidin-4-one | 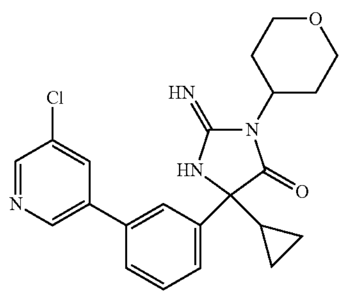 [SMILES: N=C1NC(c2cccc(-c3cncc(Cl)c3)c2)(C2CC2)C(=O)N1C1CCOCC1] | ¹H NMR (400 MHz, d⁶-DMSO) δ 8.79 (s, 1H), 8.64 (m, 1H), 8.16 (s, 1H), 7.88 (s, 1H), 7.65 (d, J = 7.2 Hz, 2H), 7.46-7.50 (m, 1H), 6.58 (m, 1H), 3.86-3.93 (m, 3H), 3.17 (m, 2H), 2.34-2.36 (m, 2H), 1.43-1.63 (m, 3H), 0.34-0.41 (m, 3H), 0.16 (s, 1H) | 411.1 |
| 490 | 5-cyclopropyl-2-imino-5-(4-methoxy-3-(pyridin-3-yl)phenyl)-3-(tetrahydro-2H-pyran-4-yl)imidazolidin-4-one | 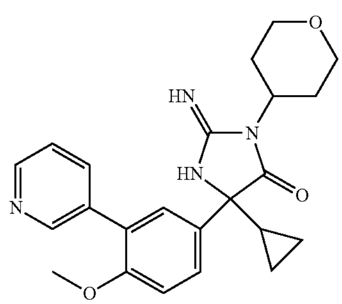 [SMILES: COc1ccc(C2(C3CC3)NC(=N)N(C3CCOCC3)C2=O)cc1-c1cccnc1] | ¹H NMR (400 MHz, d⁶-DMSO) δ 8.63 (s, 1H), 8.53 (d, J = 3.6 Hz, 1H), 7.85 (m, 1H), 7.57 (dd, J = 2.4, 8.8 Hz, 1H), 7.14-7.48 (m, 2H), 7.13 (d, J = 8.8 Hz, 1H), 6.56 (s, 1H), 3.90 (m, 3H), 3.86 (s, 3H), 3.24-3.30 (m, 3H), 2.34 (m, 2H), 1.43-1.51 (m, 3H), 0.38 (m, 3H), 0.16 (s, 1H) | 407.1 |
| 491 | 5'-(4-cyclopropyl-2-imino-5-oxo-1-(tetrahydro-2H-pyran-4-yl)imidazolidin-4-yl)-2'-methoxy-[1,1'-biphenyl]-3-carbonitrile | 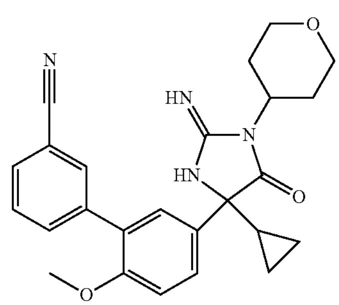 [SMILES: COc1ccc(C2(C3CC3)NC(=N)N(C3CCOCC3)C2=O)cc1-c1cccc(C#N)c1] | ¹H NMR (400 MHz, d⁶-DMSO) δ 7.79 (s, 1H), 7.76 (m, 2H), 7.64 (t, J = 7.6, 8.0 Hz, 1H), 7.57 (d, J = 8.4 Hz, 1H), 7.49 (s, 1H), 7.12 (d, J = 8.8 Hz, 1H), 6.52 (s, 1H), 3.90 (m, 3H), 3.78 (s, 3H), 3.24-3.27 (m, 2H), 2.34 (m, 2H), 1.41-1.50 (m, 3H), 2.74 (m, 3H), 0.15 (s, 1H) | 431.1 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 492 | 3'-(4-cyclohexyl-2-imino-5-oxo-1-(tetrahydro-2H-pyran-4-yl)imidazolidin-4-yl)-[1,1'-biphenyl]-3-carbonitrile | 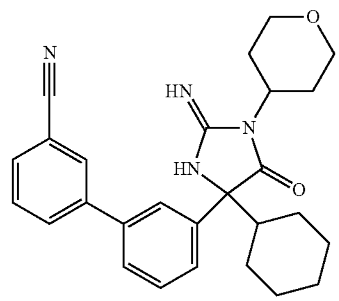 [SMILES: N#Cc1cccc(-c2cccc(C3(C4CCCCC4)NC(=N)N(C4CCOCC4)C3=O)c2)c1] | ¹H NMR (400 MHz, d⁶-DMSO) δ 8.08 (s, 1H), 7.95 (d, J = 8.0 Hz, 1H), 7.83-7.87 (m, 2H), 7.69 (t, J = 7.6, 8.0 Hz, 1H), 7.63 (t, J = 6.8, 7.6 Hz, 2H), 7.45 (t, J = 7.6, 8.0 Hz, 1H), 7.60 (s, 1H), 3.83-3.92 (m, 2H), 3.22-3.28 (m, 2H), 3.33 (m, 2H), 2.06 (s, 1H), 1.01-1.69 (m, 12H) | 443.2 |
| 493 | 3-cyclohexyl-5-cyclopentyl-2-imino-5-(4-methoxyphenyl)imidazolidin-4-one | 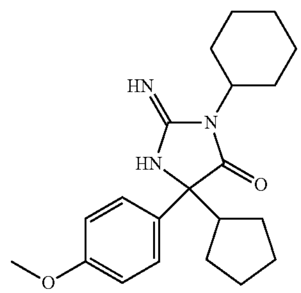 [SMILES: COc1ccc(C2(C3CCCC3)NC(=N)N(C3CCCCC3)C2=O)cc1] | ¹H NMR (400 MHz, d⁶-DMSO) δ 7.46 (d, J = 8.8 Hz, 2H), 6.85 (d, J = 8.8 Hz, 2H), 6.36 (s, 1H), 3.72 (s, 3H), 2.05 (m, 2H), 1.72 (m, 2H), 1.17-1.58 (m, 15H) | 356.2 |
| 494 | 5-cyclopropyl-2-imino-3-(tetrahydro-2H-pyran-4-yl)-5-(4-(trifluoromethoxy)phenyl)imidazolidin-4-one | 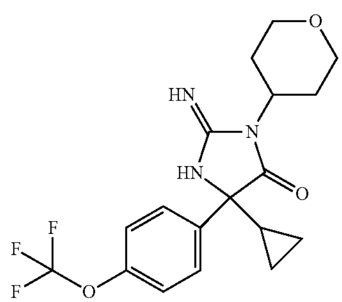 [SMILES: N=C1NC(c2ccc(OC(F)(F)F)cc2)(C2CC2)C(=O)N1C1CCOCC1] | ¹H NMR (400 MHz, d⁶-DMSO) δ 7.67 (d, J = 8.4 Hz, 2H), 7.33 (d, J = 7.6 Hz, 2H), 6.58 (s, 1H), 3.90 (m, 3H), 3.24-3.27 (m, 2H), 2.33 (m, 2H), 1.43-1.51 (m, 3H), 0.35 (m, 3H), 0.14 (s, 1H) | 384.1 |
| 495 | 5-(3-chlorophenyl)-5-cyclopropyl-2-imino-3-(tetrahydro-2H-pyran-4-yl)imidazolidin-4-one | 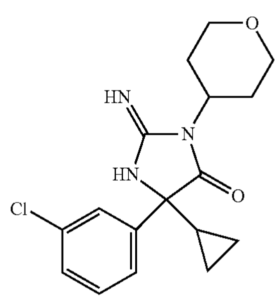 [SMILES: N=C1NC(c2cccc(Cl)c2)(C2CC2)C(=O)N1C1CCOCC1] | ¹H NMR (400 MHz, d⁶-DMSO) δ 7.53-7.55 (m, 2H), 7.31-7.39 (m, 2H), 6.62 (s, 1H), 3.90 (m, 3H), 3.24-3.27 (m, 2H), 2.32 (m, 2H), 1.43-1.51 (m, 3H), 0.34 (m, 3H), 0.15 (s, 1H) | 334.1 |
| 496 | 5-(4-chlorophenyl)-5-cyclopropyl-2-imino-3-(tetrahydro-2H-pyran-4-yl)imidazolidin-4-one | 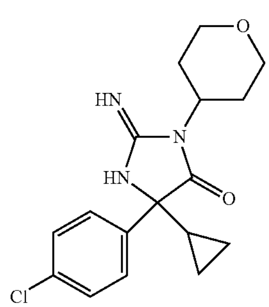 [SMILES: N=C1NC(c2ccc(Cl)cc2)(C2CC2)C(=O)N1C1CCOCC1] | ¹H NMR (400 MHz, d⁶-DMSO) δ 7.56 (d, J = 8.4 Hz, 2H), 7.39 (d, J = 8.4 Hz, 2H), 6.57 (s, 1H), 3.90 (m, 3H), 3.24-3.27 (m, 2H), 2.32 (m, 2H), 1.42-1.50 (m, 3H), 0.34 (m, 3H), 0.14 (s, 1H) | 334.1 |

TABLE 6-continued

Examples 270 and 404 to 577. This table includes both compounds of the present invention as well as comparison compounds.

| Ex. | IUPAC Name | Structure | $^1$H NMR | LC-MS m/z (M + H) |
|---|---|---|---|---|
| 497 | 5-cyclopropyl-5-(3'-ethynyl-[1,1'-biphenyl]-3-yl)-2-imino-3-(tetrahydro-2H-pyran-4-yl)imidazolidin-4-one | 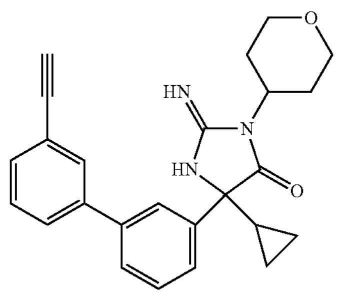 [SMILES: C#Cc1cccc(-c2cccc(C3(C4CC4)NC(=N)N(C4CCOCC4)C3=O)c2)c1] | $^1$H NMR (400 MHz, d$^6$-DMSO) δ 7.82 (s, 1H), 7.45-7.68 (m, 7H), 6.60 (s, 1H), 4.26 (s, 1H), 3.87-3.93 (m, 3H), 3.20-3.32 (m, 2H), 2.32-2.37 (m, 2H), 1.44-1.57 (m, 3H), 0.37-0.42 (m, 3H), 0.18 (s, 1H) | 400.1 |
| 498 | 5-cyclopropyl-5-(3,4-difluorophenyl)-2-imino-3-(tetrahydro-2H-pyran-4-yl)imidazolidin-4-one | 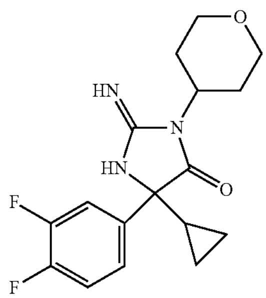 [SMILES: N=C1NC(c2ccc(F)c(F)c2)(C2CC2)C(=O)N1C1CCOCC1] | $^1$H NMR (400 MHz, d$^6$-DMSO) δ 7.48-7.53 (m, 1H), 7.37-7.40 (m, 2H), 6.62 (s, 1H), 3.87-3.92 (m, 3H), 3.24-3.32 (m, 2H), 2.26-2.37 (m, 2H), 1.43-1.50 (m, 3H), 0.31-0.37 (m, 3H), 0.14 (s, 1H) | 336.1 |
| 499 | 5-cyclopropyl-2-imino-5-(3-methoxyphenyl)-3-(tetrahydro-2H-pyran-4-yl)imidazolidin-4-one | 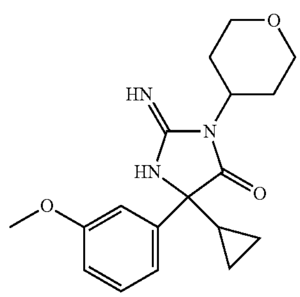 [SMILES: COc1cccc(C2(C3CC3)NC(=N)N(C3CCOCC3)C2=O)c1] | $^1$H NMR (400 MHz, d$^6$-DMSO) δ 7.22-7.26 (m, 1H), 7.09-7.14 (m, 2H), 6.83 (d, J = 8.0 Hz, 1H), 6.53 (s, 1H), 3.87-3.93 (m, 3H), 3.73 (s, 3H), 3.25-3.32 (m, 2H), 2.32-2.37 (m, 2H), 1.46 (t, J = 15.2 Hz, 3H), 0.31-0.37 (m, 3H), 0.14 (s, 1H) | 330.1 |
| 500 | 5-(2-chlorphenyl)-5-cyclopropyl-2-imino-3-(tetrahydro-2H-pyran-4-yl)imidazolidin-4-one | 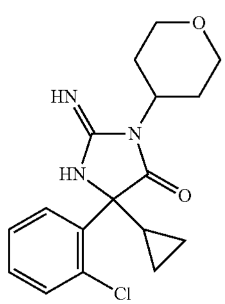 [SMILES: N=C1NC(c2ccccc2Cl)(C2CC2)C(=O)N1C1CCOCC1] | $^1$H NMR (400 MHz, d$^6$-DMSO) δ 8.02 (d, J = 7.6 Hz, 1H), 7.31-7.38 (m, 3H), 3.91-4.02 (m, 3H), 3.19-3.29 (m, 2H), 2.30-2.47 (m, 2H), 1.41-1.58 (m, 3H), 0.74 (s, 1H), 0.36-0.51 (m, 2H), 0.05 (s, 1H) | 334.1 |
| 501 | 5-(4-chloro-3-methoxyphenyl)-5-cyclohexyl-2-imino-3-(tetrahydro-2H-pyran-4-yl)imidazolidin-4-one | 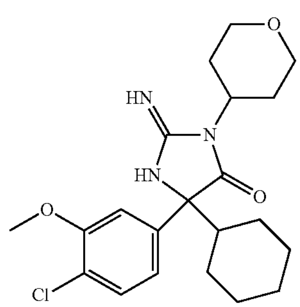 [SMILES: COc1cc(C2(C3CCCCC3)NC(=N)N(C3CCOCC3)C2=O)ccc1Cl] | $^1$H NMR (400 MHz, d$^6$-DMSO) δ 7.36 (d, J = 8.8 Hz, 1H), 7.28 (s, 1H), 7.15 (d, J = 8.8 Hz, 1H), 6.70 (brs, 1H), 3.88 (m, 3H), 3.82 (s, 3H), 3.25 (m, 3H), 2.31 (m, 2H), 1.97 (s, 1H), 1.36-1.67 (m, 6H), 1.0-1.23 (m, 6H) | 406.1 |

TABLE 6-continued

Examples 270 and 404 to 577. This table includes both compounds of the present invention as well as comparison compounds.

| Ex. | IUPAC Name | Structure | $^1$H NMR | LC-MS m/z (M + H) |
|---|---|---|---|---|
| 512 | 3-cyclohexyl-5-cyclopropyl-2-imino-5-(3-(pyridin-3-yl)phenyl)imidazolidin-4-one | 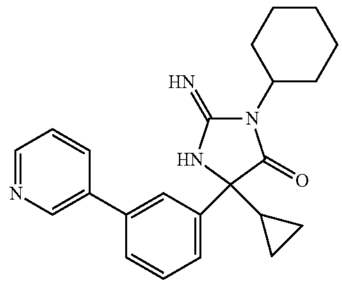 [SMILES: N=C1NC(c2cccc(-c3cccnc3)c2)(C2CC2)C(=O)N1C1CCCCC1] | $^1$H NMR (400 MHz, d$^6$-DMSO) δ 8.80-8.86 (m, 1H), 8.57-8.58 (m, 1H), 7.97-7.99 (m, 1H), 7.80-7.85 (m, 1H), 7.43-7.64 (m, 4H), 6.48 (s, 1H), 3.64 (t, J = 11.6 Hz, 1H), 2.00-2.12 (m, 2H), 1.70-1.77 (m, 2H), 1.50-1.57 (m, 4H), 1.06-1.28 (m, 3H), 0.30-0.44 (m, 3H), 0.10-0.18 (m, 1H) | 385.2 |
| 513 | 5-(3-(1-cyclohexyl-4-cyclopropyl-2-imino-5-oxoimidazolidin-4-yl)phenyl)nicotinonitrile | 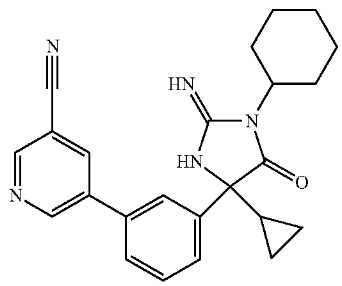 [SMILES: N#Cc1cncc(-c2cccc(C3(C4CC4)NC(=N)N(C4CCCCC4)C3=O)c2)c1] | $^1$H NMR (400 MHz, d$^6$-DMSO) δ 9.13 (s, 1H), 9.04 (s, 1H), 8.60 (s, 1H), 7.95 (m, 1H), 7.66-7.72 (m, 2H), 7.50-7.53 (m, 1H), 6.52 (s, 1H), 3.72 (m, 1H), 2.00-2.14 (m, 2H), 1.76 (t, J = 11.2 Hz, 2H), 1.52-1.60 (m, 3H), 1.10-1.29 (m, 4H), 0.30-0.42 (m, 3H), 0.15 (s, 1H) | 400.1 |
| 514 | 5-(3-(5-chloropyridin-3-yl)phenyl)-3-cyclohexyl-5-cyclopropyl-2-iminoimidazolidin-4-one | 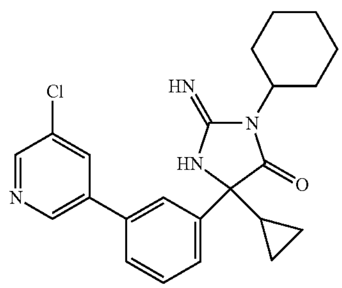 [SMILES: N=C1NC(c2cccc(-c3cncc(Cl)c3)c2)(C2CC2)C(=O)N1C1CCCCC1] | $^1$H NMR (400 MHz, d$^6$-DMSO) δ 8.79 (s, 1H), 8.64 (d, J = 1.6 Hz, 1H), 8.16 (s, 1H), 7.88 (s, 1H), 7.66 (t, J = 7.2 Hz, 2H), 7.47-7.50 (m, 1H), 6.54 (s, 1H), 3.69 (m, 1H), 1.99-2.13 (m, 2H), 1.74 (t, J = 12.4 Hz, 2H), 1.50-1.59 (m, 3H), 1.12-1.28 (m, 4H), 0.26-0.42 (m, 3H), 0.18 (s, 1H) | 409.1 |
| 515 | 3-cyclohexyl-5-cyclopropyl-2-imino-5-(3-(5-(prop-1-yn-1-yl)pyridin-3-yl)phenyl)imidazolidin-4-one | 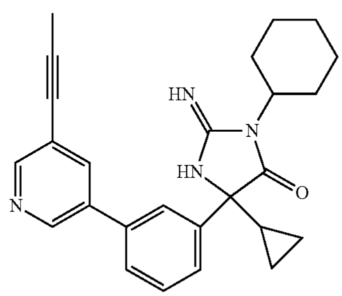 [SMILES: CC#Cc1cncc(-c2cccc(C3(C4CC4)NC(=N)N(C4CCCCC4)C3=O)c2)c1] | $^1$H NMR (400 MHz, d$^6$-DMSO) δ 8.76 (s, 1H), 8.58 (s, 1H), 7.99 (s, 1H), 7.86 (s, 1H), 7.63 (d, J = 7.2 Hz, 2H), 7.46-7.48 (m, 1H), 6.5 (s, 1H), 3.66 (s, 1H), 1.97-2.12 (m, 5H), 1.74 (t, J = 12.4 Hz, 2H), 1.49-1.57 (m, 3H), 1.09-1.27 (m, 4H), 0.32-0.40 (m, 3H), 0.16 (s, 1H) | 413.2 |
| 516 | 5-(3-(5-chloropyridin-3-yl)phenyl)-5-cyclohexyl-2-imino-3-(tetrahydro-2H-pyran-4-yl)imidazolidin-4-one | 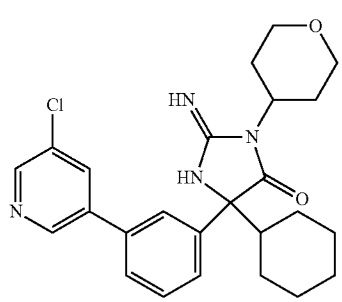 [SMILES: N=C1NC(c2cccc(-c3cncc(Cl)c3)c2)(C2CCCCC2)C(=O)N1C1CCOCC1] | $^1$H NMR (400 MHz, d$^6$-DMSO) δ 8.79 (s, 1H), 8.64 (s, 1H), 8.15 (s, 1H), 7.87 (s, 1H), 7.66 (d, J = 7.6 Hz, 2H), 7.47 (m, 1H), 3.86 (m, 3H), 3.21-3.28 (m, 2H), 2.33 (m, 2H), 2.06 (s, 1H), 1.04-1.68 (m, 13H) | 453.2 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 517 | 5-cyclohexyl-2-imino-5-(3-(pyridin-3-yl)phenyl)-3-(tetrahydro-2H-pyran-4-yl)imidazolidin-4-one | 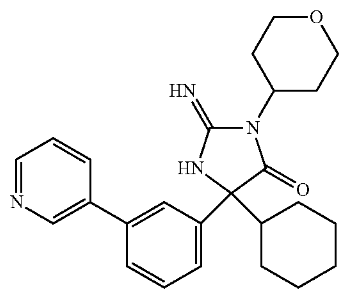 [SMILES: N=C1NC(c2cccc(-c3cccnc3)c2)(C2CCCCC2)C(=O)N1C1CCOCC1] | ¹H NMR (400 MHz, d⁶-DMSO) δ 8.83 (s, 1H), 8.58 (d, J = 4.4 Hz, 1H), 8.01 (d, J = 8.4 Hz, 1H), 7.85 (s, 1H), 7.62 (t, J = 7.6, 8.4 Hz, 2H), 7.44-7.52 (m, 2H), 6.60 (s, 1H), 3.84-4.01 (m, 3H), 3.21-3.25 (m, 2H), 2.33 (m, 2H), 2.06 (s, 1H), 1.06-1.69 (m, 13H) | 419.2 |
| 518 | 5-cyclopropyl-2-imino-5-(2-methoxyphenyl)-3-(tetrahydro-2H-pyran-4-yl)imidazolidin-4-one | 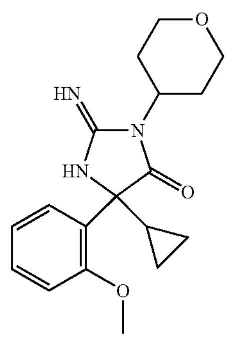 [SMILES: COc1ccccc1C1(C2CC2)NC(=N)N(C2CCOCC2)C1=O] | ¹H NMR (400 MHz, d⁶-DMSO) δ 7.77 (d, J = 7.6 Hz, 1H), 7.29 (m, 1H), 6.97 (m, 2H), 6.36 (brs, 1H), 4.05 (m, 1H), 3.94 (m, 2H), 3.64 (s, 3H), 2.41 (m, 1H), 1.58 (m, 1H), 1.48 (m, 1H), 1.34 (m, 1H), 0.72 (m, 1H), 0.46 (m, 1H), 0.31 (m, 1H), 0.042 (m, 1H) | 330.1 |
| 519 | 5-cyclopropyl-5-(3-hydroxyphenyl)-2-imino-3-(tetrahydro-2H-pyran-4-yl)imidazolidin-4-one | 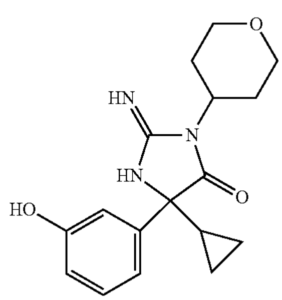 [SMILES: N=C1NC(c2cccc(O)c2)(C2CC2)C(=O)N1C1CCOCC1] | ¹H NMR (400 MHz, d⁶-DMSO) δ 7.05-7.09 (m, 1H), 6.91-6.98 (m, 2H), 6.59-6.61 (m, 1H), 6.49 (s, 1H), 3.89 (m, 3H), 2.33 (m, 2H), 1.42-1.49 (m, 3H), 1.19-1.23 (m, 2H), 0.27-0.43 (m, 3H), 0.09 (s, 1H) | 316.1 |
| 547 | 3-cyclohexyl-5,5-bis(4-hydroxyphenyl)-2-iminoimidazolidin-4-one | 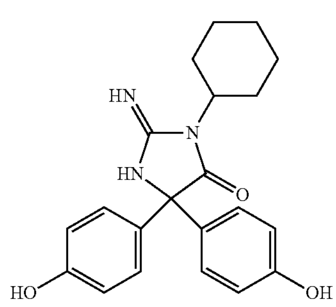 [SMILES: N=C1NC(c2ccc(O)cc2)(c2ccc(O)cc2)C(=O)N1C1CCCCC1] | ¹H NMR (400 MHz, d⁶-DMSO) δ 9.30 (brs, 1H), 7.09 (d, J = 8.8 Hz, 4H), 6.66 (d, J = 8.8 Hz, 4H), 3.75 (m, 1H), 2.09 (m, 2H), 1.74 (m, 2H), 1.56 (m, 3H), 1.27 (m, 3H) | 366.1 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 548 | 5-cyclopropyl-2-imino-5-(4-(pyridin-3-yl)phenyl)-3-(tetrahydro-2H-pyran-4-yl)imidazolidin-4-one | 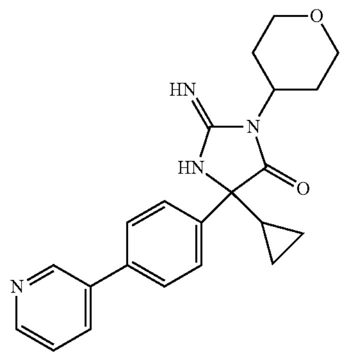 [SMILES: N=C1NC(c2ccc(-c3cccnc3)cc2)(C2CC2)C(=O)N1C1CCOCC1] | ¹H NMR (400 MHz, d⁶-DMSO) δ 8.88 (s, 1H), 8.56 (s, 1H), 8.05 (d, J = 8.0 Hz, 1H), 7.68 (s, 4H), 7.49 (m, 1H), 6.60 (s, 1H), 3.90 (m, 3H), 3.25-3.29 (m, 2H), 2.36 (m, 2H), 1.44-1.52 (m, 3H), 0.40 (m, 3H), 0.18 (s, 1H) | 377.1 |
| 549 | 3-cyclohexyl-5-cyclopropyl-5-(3-hydroxyphenyl)-2-iminoimidazolidin-4-one | 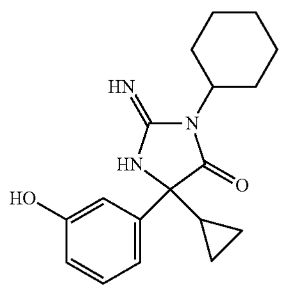 [SMILES: N=C1NC(c2cccc(O)c2)(C2CC2)C(=O)N1C1CCCCC1] | ¹H NMR (400 MHz, d⁶-DMSO) δ 8.20 (s, 1H), 7.10 (t, J = 7.6 Hz, 1H), 6.96 (s, 2H), 6.63 (d, J = 7.6 Hz, 1H), 3.68-3.74 (m, 1H), 2.06-2.09 (m, 2H), 1.74 (m, 2H), 1.39-1.60 (m, 3H), 1.09-1.23 (m, 4H), 0.30-0.38 (m, 3H), 0.12 (s, 1H) | 314.1 |
| 550 | 5,5-bis(4-hydroxyphenyl)-2-imino-3-(tetrahydro-2H-pyran-4-yl)imidazolidin-4-one | 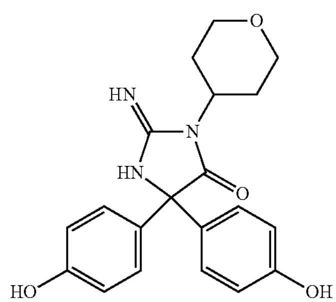 [SMILES: N=C1NC(c2ccc(O)cc2)(c2ccc(O)cc2)C(=O)N1C1CCOCC1] | ¹H NMR (400 MHz, MeOD) δ 7.15 (m, 4H), 6.80 (m, 4H), 4.47 (m, 1H), 3.61 (m, 4H), 2.24 (m, 1H), 2.13 (m, 1H), 1.95 (m, 1H), 1.87 (m, 1H) | 368.1 |
| 551 | 3-cyclohexyl-5-cyclopropyl-5-(4-hydroxyphenyl)-2-iminoimidazolidin-4-one | 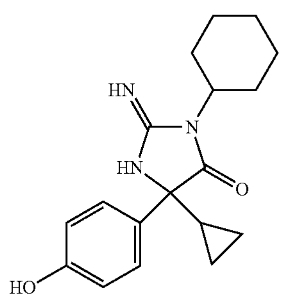 [SMILES: N=C1NC(c2ccc(O)cc2)(C2CC2)C(=O)N1C1CCCCC1] | ¹H NMR (400 MHz, d⁶-DMSO) δ 9.70 (s, 1H), 9.33 (brs, 1H), 7.31 (d, J = 8.8 Hz, 2H), 6.81 (d, J = 8.8 Hz, 2H), 3.96 (m, 1H), 2.01 (m, 2H), 1.75 (s, 4H), 1.46 (m, 2H), 1.28 (m, 2H), 1.13 (m, 1H), 0.69 (m, 1H), 0.56 (m, 1H), 0.44 (m, 1H), 0.34 (m, 1H) | 314.1 |
| 563 | 5-(4'-chloro-[1,1'-biphenyl]-3-yl)-5-cyclopropyl-2-imino-3-(tetrahydro-2H-pyran-4-yl)imidazolidin-4-one | 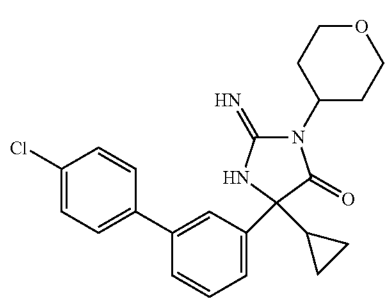 [SMILES: N=C1NC(c2cccc(-c3ccc(Cl)cc3)c2)(C2CC2)C(=O)N1C1CCOCC1] | ¹H NMR (400 MHz, d⁶-DMSO) δ 7.81 (s, 1H), 7.53-7.64 (m, 6H), 7.42-7.45 (m, 1H), 6.57 (m, 1H), 3.86-3.93 (m, 3H), 3.25-3.30 (m, 2H), 2.33-2.37 (m, 2H), 1.43-1.52 (m, 3H), 0.34-0.42 (m, 3H), 0.17 (m, 1H) | 410.1 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 564 | 4-((4-(1-cyclohexyl-4-cyclopropyl-2-imino-5-oxoimidazolidin-4-yl)phenoxy)methyl)benzonitrile | 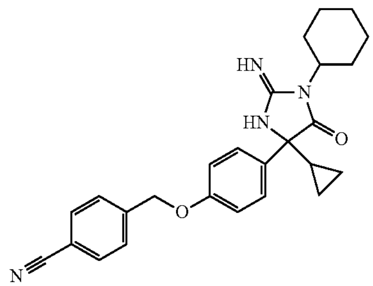 [SMILES: N#Cc1ccc(COc2ccc(C3(C4CC4)NC(=N)N(C4CCCCC4)C3=O)cc2)cc1] | ¹H NMR (400 MHz, CDCl$_3$) δ 7.66 (d, J = 7.6 Hz, 2H), 7.51 (m, 4H), 6.91 (d, J = 8.8 Hz, 2H), 5.10 (s, 2H), 3.80 (m, 1H), 2.08 (m, 2H), 1.85 (m, 2H), 1.70 (m, 3H), 1.40 (m, 1H), 1.37-1.17 (m, 3H), 0.56-0.40 (m, 4H) | 429.2 |
| 565 | 3-cyclohexyl-5-cyclopropyl-2-imino-5-(2-methoxyphenyl)imidazolidin-4-one | 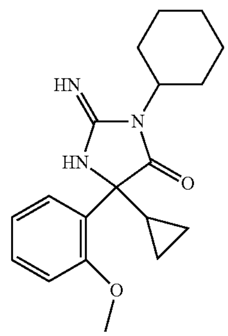 [SMILES: COc1ccccc1C1(C2CC2)NC(=N)N(C2CCCCC2)C1=O] | ¹H NMR (400 MHz, CDCl$_3$) δ 7.80 (d, J = 8.8 Hz, 1H), 7.27 (m, 1H), 6.96 (m, 1H), 6.86 (d, J = 8.8 Hz, 1H), 3.93 (m, 1H), 3.74 (s, 3H), 3.42 (s, 2H), 2.21 (m, 2H), 1.87-1.66 (m, 5H), 1.48-1.21 (m, 4H), 0.72 (m, 1H), 0.43 (m, 2H), 0.27 (m, 1H) | 328.1 |
| 566 | 5-cyclopropyl-5-(2-hydroxyphenyl)-2-imino-3-(tetrahydro-2H-pyran-4-yl)imidazolidin-4-one | 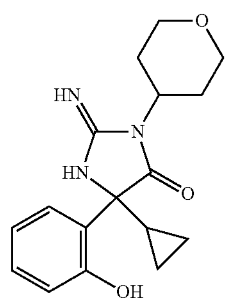 [SMILES: N=C1NC(c2ccccc2O)(C2CC2)C(=O)N1C1CCOCC1] | ¹H NMR (400 MHz, CDCl$_3$) δ 7.84 (m, 1H), 7.12 (m, 1H), 6.81 (m, 1H), 3.24-3.96 (m, 7H), 2.03 (m, 1H), 1.73 (m, 3H), 1.43 (m, 1H), 1.25 (m, 2H), 0.61 (m, 1H), 0.21-0.44 (m, 3H) | 316.1 |
| 567 | 4-((3-(1-cyclohexyl-4-cyclopropyl-2-imino-5-oxoimidazolidin-4-yl)phenoxy)methyl)benzonitrile | 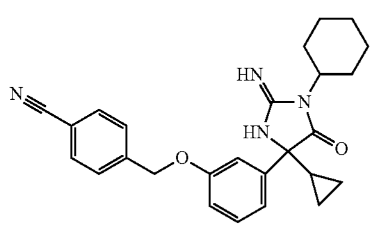 [SMILES: N#Cc1ccc(COc2cccc(C3(C4CC4)NC(=N)N(C4CCCCC4)C3=O)c2)cc1] | ¹H NMR (400 MHz, d$^6$-DMSO) δ 7.86 (d, J = 7.6 Hz, 2H), 7.64 (d, J = 7.6 Hz, 2H), 7.27-7.31 (m, 1H), 7.11-7.15 (m, 2H), 6.95 (d, J = 7.6 Hz, 1H), 5.21 (s, 2H), 3.74 (m, 1H), 1.99-2.06 (m, 2H), 1.75 (m, 2H), 1.51-1.60 (m, 3H), 1.09-1.23 (m, 4H), 0.37-0.39 (m, 3H), 0.20 (s, 1H) | 429.2 |
| 568 | 4-((3-(1-cyclohexyl-4-cyclopropyl-2-imino-5-oxoimidazolidin-4-yl)phenoxy)methyl)benzamide | 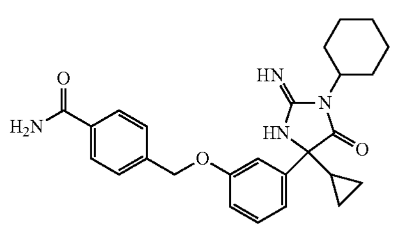 [SMILES: N=C1NC(c2cccc(OCc3ccc(C(N)=O)cc3)c2)(C2CC2)C(=O)N1C1CCCCC1] | ¹H NMR (400 MHz, d$^6$-DMSO) δ 7.97 (s, 1H), 7.88 (d, J = 8.0 Hz, 2H), 7.51 (d, J = 8.0 Hz, 2H), 7.36 (s, 1H), 7.12-7.24 (m, 3H), 6.92 (m, 1H), 5.13 (s, 2H), 3.65 (m, 1H), 1.99-2.08 (m, 2H), 1.74 (m, 2H), 1.46-1.59 (m, 4H), 1.09-1.24 (m, 4H), 0.35 (m, 3H), 0.12 (s, 1H) | 447.2 |

TABLE 6-continued

Examples 270 and 404 to 577. This table includes both compounds of the present invention as well as comparison compounds.

| Ex. | IUPAC Name | Structure | ¹H NMR | LC-MS m/z (M + H) |
|---|---|---|---|---|
| 570 | 3-cyclohexyl-5-cyclopropyl-2-imino-5-(3-phenoxyphenyl)imidazolidin-4-one | 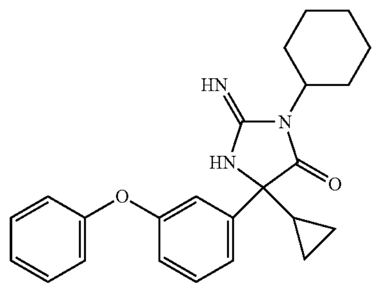 [SMILES: N=C1NC(c2cccc(Oc3ccccc3)c2)(C2CC2)C(=O)N1C1CCCCC1] | 1H NMR (400 MHz, d⁶-DMSO) δ 7.34-7.40 (m, 4H), 7.12-7.16 (m, 2H), 6.99 (d, J = 8.0 Hz, 2H), 6.87 (s, 1H), 6.43 (s, 1H), 3.61-3.62 (m, 1H), 2.00-2.06 (m, 2H), 1.73 (m, 2H), 1.38-1.59 (m, 4H), 1.08-1.23 (m, 3H), 0.28-0.35 (m, 3H), 0.09 (m, 1H) | 390.2 |
| 572 | 5-cyclopropyl-5-(3,4-dichlorophenyl)-2-imino-3-(tetrahydro-2H-pyran-4-yl)imidazolidin-4-one | 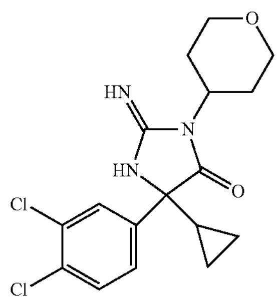 [SMILES: N=C1NC(c2ccc(Cl)c(Cl)c2)(C2CC2)C(=O)N1C1CCOCC1] | ¹H NMR (400 MHz, d⁶-DMSO) δ 7.73 (s, 1H), 7.61 (d, J = 8.4 Hz, 1H), 7.56 (d, J = 8.4 Hz, 1H), 6.70 (s, 1H), 3.90 (m, 3H), 3.23-3.29 (m, 2H), 2.30 (m, 2H), 1.45 (m, 3H), 0.33 (m, 3H), 0.14 (s, 1H) | 368.1 |
| 573 | 3-cyclohexyl-5-cyclopropyl-5-(2-hydroxyphenyl)-2-iminoimidazolidin-4-one | 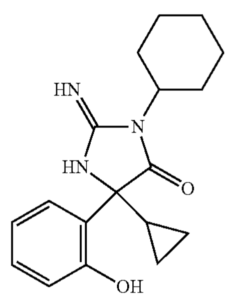 [SMILES: N=C1NC(c2ccccc2O)(C2CC2)C(=O)N1C1CCCCC1] | ¹H NMR (400 MHz, d⁶-DMSO) δ 8.10 (brs, 1H), 7.40 (m, 1H), 7.12 (s, 1H), 6.77 (m, 2H), 3.60 (m, 1H), 1.56-1.82 (m, 6H), 1.11-1.30 (m, 5H), 0.45 (m, 3H), 0.09 (m, 1H) | 314.2 |
| 574 | 5-(4-chlorophenyl)-5-cyclohexyl-2-imino-3-(tetrahydro-2H-pyran-4-yl)imidazolidin-4-one | 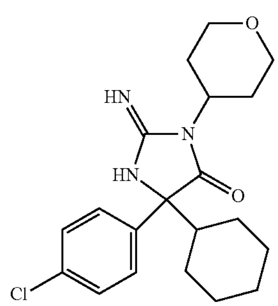 [SMILES: N=C1NC(c2ccc(Cl)cc2)(C2CCCCC2)C(=O)N1C1CCOCC1] | ¹H NMR (400 MHz, d⁶-DMSO) δ 7.55 (d, J = 8.8 Hz, 2H), 7.36 (d, J = 8.8 Hz, 2H), 6.54 (brs, 1H), 3.87 (m, 3H), 3.27 (m, 2H), 2.30 (m, 2H), 1.90 (s, 1H), 1.65 (m, 1H), 1.56 (s, 1H), 1.44 (m, 2H), 1.33 (m, 1H), 1.23-1.32 (m, 1H), 1.03 (m, 5H) | 376.1 |
| 575 | 5-(4-chlorophenyl)-3,5-dicyclohexyl-2-iminoimidazolidin-4-one | 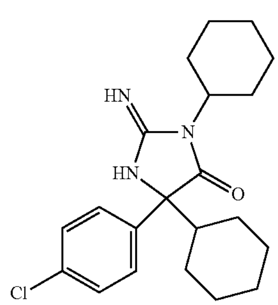 [SMILES: N=C1NC(c2ccc(Cl)cc2)(C2CCCCC2)C(=O)N1C1CCCCC1] | ¹H NMR (400 MHz, d⁶-DMSO) δ 7.54 (d, J = 7.6 Hz, 2H), 7.35 (d, J = 7.6 Hz, 2H), 6.47 (brs, 1H), 3.65 (s, 1H), 2.03 (m, 2H), 1.89 (m, 1H), 1.69 (m, 3H), 1.52 (m, 4H), 1.37 (m, 2H), 0.83-1.24 (m, 9H) | 374.2 |

TABLE 6-continued

Examples 270 and 404 to 577. This table includes both compounds of the present invention as well as comparison compounds.

| Ex. | IUPAC Name | Structure | $^1$H NMR | LC-MS m/z (M + H) |
|---|---|---|---|---|
| 577 | 5-(4-chlorophenyl)-3-cyclohexyl-5-cyclopropyl-2-iminoimidazolidin-4-one | 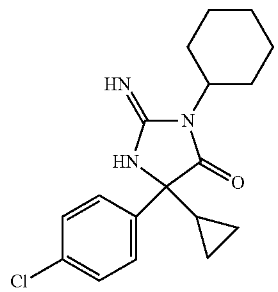 [SMILES: N=C1NC(c2ccc(Cl)cc2)(C2CC2)C(=O)N1C1CCCCC1] | $^1$H NMR (400 MHz, d$^6$-DMSO) δ 7.56 (d, J = 8.0 Hz, 2H), 7.37 (d, J = 7.2 Hz, 2H), 6.49 (s, 2H), 3.63 (m, 1H), 2.01-2.07 (m, 2H), 1.73 (m, 2H), 1.40-1.59 (m, 4H), 1.09-1.24 (m, 3H), 030-0.35 (m, 3H), 0.11 (s, 1H) | 332.1 |

Examples 569 and 571

Preparation of N-Benzylated Examples

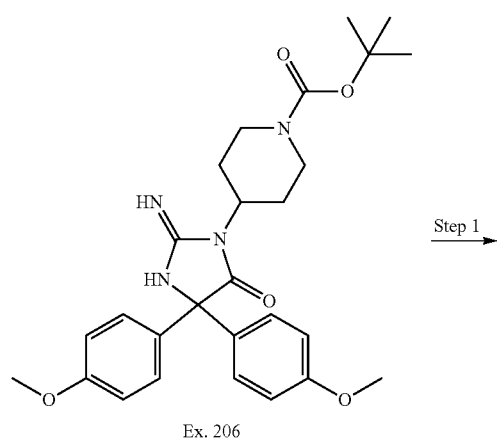

Ex. 206

Step 1

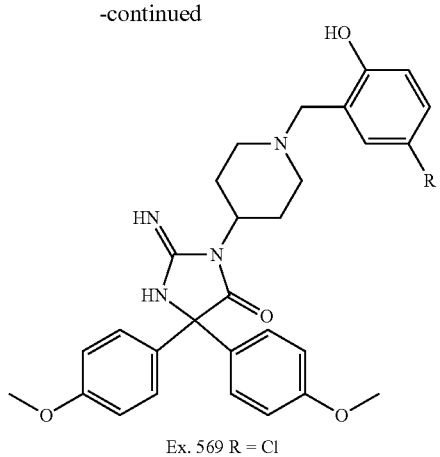

Ex. 569 R = Cl
Ex. 571 R = H

Step 1. Preparation of 2-imino-5,5-bis(4-methoxyphenyl)-3-(piperidin-4-yl)imidazolidin-4-one (207)

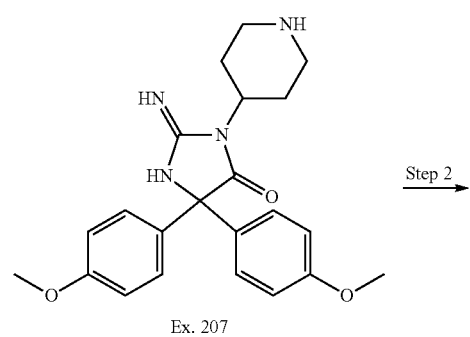

Ex. 207

Step 2

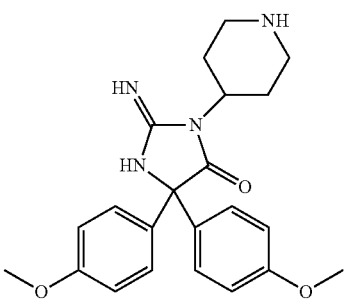

To a solution of 206 (2.6 g, 5.25 mmol) in DCM (10 ml) was added 10 ml of TFA and the resulting solution was stirred at room temperature for 1 h. The mixture was concentrated in vacuo and the residue was neutralized by NaHCO$_3$ and extracted with dichloromethane. The combined organic phases were dried over sodium sulfate and concentrated in vacuo. The residue was used without further purification.

Step 2. Preparation of 3-(1-(5-chloro-2-hydroxybenzyl)piperidin-4-yl)-2-imino-5,5-bis(4-methoxyphenyl)imidazolidin-4-one (569)

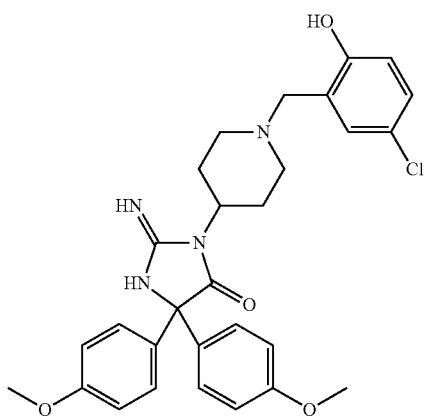 [SMILES: COc1ccc(C2(c3ccc(OC)cc3)NC(=N)N(C3CCN(Cc4cc(Cl)ccc4O)CC3)C2=O)cc1]

5-Chlorosalicylaldehyde (0.24 g, 1.53 mmol), sodium cyanoborohydride (0.33 g, 5.25 mmol) and 2-imino-5,5-bis(4-methoxyphenyl)-3-(piperidin-4-yl)imidazolidin-4-one (0.41 g, 1.04 mmol) were dissolved in ethanol and the solution was stirred at room temperature overnight. The mixture was extracted with dichloromethane. The combined organic phases were dried over sodium sulfate and concentrated in vacuo. The residue was purified over a silica column (MeOH/DCM=1/20) to give the title compound as a white solid (0.18 g, 33% yield).

3-(1-(2-hydroxybenzyl)piperidin-4-yl)-2-imino-5,5-bis(4-methoxyphenyl)imidazolidin-4-one (571) was prepared in a similar manner.

TABLE 7

Examples 569 and 571.

| Ex. | IUPAC Name | Structure | $^1$H NMR | LC-MS m/z (M + H) |
|---|---|---|---|---|
| 569 | 3-(1-(5-chloro-2-hydroxybenzyl)piperidin-4-yl)-2-imino-5,5-bis(4-methoxyphenyl)-imidazolidin-4-one | 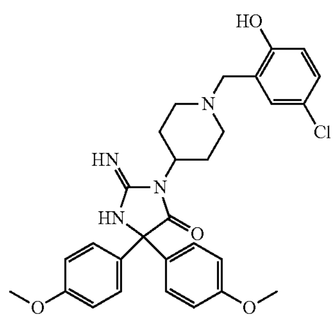 [SMILES: COc1ccc(C2(c3ccc(OC)cc3)NC(=N)N(C3CCN(Cc4cc(Cl)ccc4O)CC3)C2=O)cc1] | $^1$H NMR (400 MHz, d$^6$-DMSO) δ 7.24 (d, J = 8.0 Hz, 4H), 7.16 (s, 1H), 7.11 (d, J = 8.8 Hz, 1H), 6.85 (d, J = 7.6 Hz, 4H), 6.75 (d, J = 8.4 Hz, 1H), 6.5 (s, 1H), 3.71 (s, 6H), 3.60 (s, 2H), 2.91 (m, 2H), 2.38 (m, 2H), 2.08 (m, 2H), 1.54 (m, 2H) | 535.1 |
| 571 | 3-(1-(2-hydroxybenzyl)piperidin-4-yl)-2-imino-5,5-bis(4-methoxyphenyl)-imidazolidin-4-one | 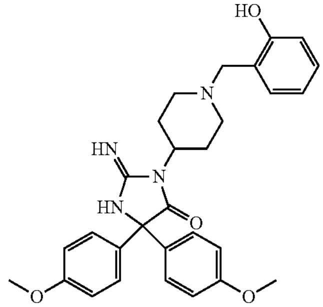 [SMILES: COc1ccc(C2(c3ccc(OC)cc3)NC(=N)N(C3CCN(Cc4ccccc4O)CC3)C2=O)cc1] | $^1$H NMR (400 MHz, d$^6$-DMSO) δ 7.25 (d, J = 8.0 Hz, 4H), 7.07 (m, 2H), 6.83 (d, J = 8.0 Hz, 4H), 6.72 (m, 2H), 6.51 (s, 1H), 3.70 (s, 6H), 3.62 (s, 2H), 2.93 (m, 2H), 2.38 (m, 2H), 2.07 (m, 2H), 1.54 (m, 2H) | 501.2 |

Structure Activity Relationship Studies

The Pf 3D7 $IC_{50}$ values as well as associated lipophilicity profile for the compounds for representative compounds are shown in Table 1. Compounds prepared in the $R^2/R^3$ p-methoxyphenyl series were approximately 10-fold more potent than those in the unadorned phenyl series. Simple replacement of the phenylbutyl side chain with smaller alkyl groups, such as methyl, ethyl, and propyl, resulted in size-dependent losses in potency. Large flexible groups, such as benzyl and phenethyl, and secondary branched alkyls, such as isopropyl, were generally well tolerated. Cyclic alkyl groups generally provided an optimal combination of potency and reduced lipophilicity.

Cyclohexyl analog 117 was selected for further optimization studies without adding additional stereocenters to the compounds. The pyran derivative has equivalent potency to cyclohexyl while reducing the lipophilicy by 2 orders of magnitude. Extension of the cyclohexyl and pyran rings by one carbon often lead to nearly identical potencies to those of the corresponding analogs 117 and 176.

Having identified the structure activity relationship (SAR) based upon modifications to the phenylbutyl side chain, the SAR of the aryl rings while keeping R1 constant as the cyclohexyl ring was explored. Moving the methoxy groups to the 3-position results in a slight reduction of potency while deletion of the second methoxy group only had a negligible effect on potency. The more lipophilic methyl and chloro derivatives were tolerated in the 4- and 3-positions but did not generally enhance potency of the compound.

Many aminohydantoin inhibitors of BACE exhibit an aryl group in the 3-position of the aromatic ring and this modification to the $R^2/R^3$ position was also explored. Without being bound by theory, it is believed that this substitution pattern allows the biaryl group of the inhibitor to occupy both the S1 and the S3 binding pockets simultaneously. Since similar aspartic protease active site topography is believed to be present in the *Plasmodium* target, biaryl derivatives were prepared. Aryl derivatives showed similar potency while heteroaryl derivatives such as one with a 3-pyridyl ring results in improved potency. Interestingly, the methoxy group on the second aryl ring generally has a negligible effect on potency. 4-Pyridyl substitution has a similar effect to that of 3-pyridyl while 2-pyridyl generally has a slightly lower potency. Phenyl and benzyl ethers also appear to be equally efficacious.

Biological Assay Results

The activity of the compounds of the present invention was tested in the following assays. The results of testing in the assays are shown in Tables 8-13 below.

In Vitro Antimalarial Assays (3D7 and Dd2)

In vitro antimalarial activity was determined by a malaria SYBR Green I-based fluorescence (MSF) method described previously by Smilkstein et al. (2004, which is incorporated herein by reference) with slight modification (Winter, et al., 2006, which is incorporated herein by reference). Stock solutions of each test drug were prepared in DMSO at a concentration of 20 mM. The drug solutions were serially diluted with culture medium and distributed to asynchronous parasite cultures on 96-well plates in quadruplicate in a total volume of 100 µL to achieve 0.5% parasitemia with a 2% hematocrit in a total volume of 100 pt. The plates were then incubated for 72 h at 37° C. After incubation, 100 µL of lysis buffer with 0.2 µL/mL SYBR Green I was added to each well. The plates were incubated at 37° C. for an hour in the dark and then placed in a 96-well fluorescence plate reader (Spectramax Gemini-EM; Molecular Diagnostics) with excitation and emission wavelengths at 497 nm and 520 nm, respectively, for measurement of fluorescence. The 50% inhibitory concentration ($IC_{50}$) was determined by nonlinear regression analysis of logistic dose-response curves (GraphPad Prism software).

Antimalarial potency of compounds was determined by this technique for both *Plasmodium falciparum* 3D7 (CQ-sensitive) and Dd2 (multi-drug resistant) strains. The $IC_{50}$ values for some of these compounds are reported in Tables 8 and 9 below as 3D7 $IC_{50}$ and Dd2 $IC_{50}$ values.

Plasmepsin-2 and Plasmepsin-4 Enzyme Inhibition Assay (PM-2 and PM-4)

Plasmepsin-2 (PM-2; Plm II) and Plasmepsin (PM-4; Plm IV) expression and purification was performed following the published protocols (Istvan E S and Goldberg D E, 2005). The final purified protein was activated by diluting the protein to 0.3 mg/mL in activating buffer (0.1 M citrate pH 4.5, 0.1% Tween-20, 50 mM dithiothreitol) and incubated at room temperature for 40 min, then the activated enzyme was diluted in assay buffer (50 mM sodium acetate pH 4.7, 0.01% Tween-20). The enzymatic inhibition reaction was performed in 384 well plates with a total volume of 20 µl. 10 µl of diluted PM-2 or PM-4 enzyme was added to the 384-well plate except blank wells (blank wells add 10 µL of assay buffer) and 20 nL of serials of diluted 1000× compounds were added to the wells with 520 Echo® Liquid Handling System (Labcyte Inc.). 10 µL PM-2 peptide substrate (AnaSpec, Cat#, 62050) with assay buffer was then added to final concentration of 20 µM to start the reaction. After incubation the reaction at room temperature for 60 min, the fluorescence intensity at Ex/Em=360 nm/535 nm was measured using EnVision multilabel plate reader (Perkin-Elmer). The $IC_{50}$ values were obtained using Graph Pad Prism 4 and are reported in Tables 8 and 9 below as PM-2 $IC_{50}$ values.

β-Secretase (BACE1), Cathepsin D, and Cathepsin E Enzyme Inhibition Assay

The recombinant human BACE1, Cathepsin D, and Cathepsin E enzymes were purchased from R&D Systems (catalog numbers are 931-AS, 1014AS and 1294AS, respectively). The enzymatic inhibition activity assays were determined using the fluorescence resonance energy transfer (FRET) assay. The assays were performed in a 384-well plate format. The recombinant human BACE-1 enzyme (R&D Systems, catalog#931-AS) was diluted to 20 ng/µL in assay buffer (100 mM sodium acetate pH 4.0), 10 point 1:3 serial dilutions of compound in DMSO were preincubated with the enzyme for 15 min at room temperature. The concentration of Cathepsin D was 20 ng/µL, and 1 ng/µL of Cathepsin E was used. CatD and CatE were activated by incubation in assay buffer (0.1 M NaOAc, 0.2 M NaCl, pH 3.5) at room temperature for 30 min. Subsequently, the rhBACE-1 substrate (R&D Systems, catalog# ES004), the Cathepsin D and Cathepsin E substrate (R&D Systems, Catalog # ES001) were added accordingly to final concentration 20 µM to initiate the reaction. After 60 min incubation at room temperature, the time-resolved fluorescence at Ex/Em=360 nm/460 nm was measured on an EnVision multilabel plate reader (Perkin-Elmer). The analytical software, GraphPad Prism 5.0 (GraphPad Software, Inc., USA) was used to generate $IC_{50}$ values via non-linear regression analysis, which are reported in Tables 8-13 below as BACE1 $IC_{50}$ values.

Cytochrome P450 Inhibitory Assay

The cytochrome P450 inhibitory potentials of compounds for human recombinant CYP1A2, CYP2C9, CYP2C19, CYP2D6, and CYP3A were determined using Vivid CYP450 blue screening kits (Invitrogen, USA). All of the procedures were performed according the instruction provided by the manufacturer. Briefly, serials of diluted compounds were incubated the vivid CYP450 reaction systems including CYP450 BACULOSOMES with different recombinant human CYP450 isozymes and the appropriate vivid CYP450 substrates, and rabbit NADPH-P450 reductase, and the regeneration system. Ketoconazole was used as reference CYP450 inhibitor. After 30 minutes incubation at room temperature, the fluorescence was measured with an excitation at 400 nm and an emission at 460 nm using Envision 2104 multi-label Reader (Perkin Elmer, USA). The $IC_{50}$ values were calculated by nonlinear regressions using GraphPad Prism 5.

HepG2 Cytotoxicity Assay

HepG2 cells (ATCC Cat. No. HB-8065) were maintained in DMEM supplemented with 10% fetal bovine serum and L-glutamine. Cells were grown at 37° C. and 5% $CO_2$ on flasks coated with poly-d-lysine. To assess compounds for potential cytotoxic properties cells were plated at 10,000 cells per well on 96-well poly-d-lysine plates at 10,000 cells per well. HepG2 cells were allowed to adhere for at least 4 hours prior to application of test compounds. Cells were incubated with test compounds for 72 hours before measuring cellular viability. Cellular viability was measured using PrestoBlue® Cell Viability Reagent (Life Technologies). Briefly, 11 µL of 10× PrestoBlue reagent was added to 100 µl in each assay well. Cells were incubated at 37° C. and 5% $CO_2$ for 30 minutes prior to reading on Tecan Safire2, excitation at 560 nm, 10 nm bandwidth and emission at 590 nm, 10 nm bandwidth. GraphPad Prism 5.0 (GraphPad Software, Inc., USA) was used to generate $IC_{50}$ values via non-linear regression analysis.

MLM, RLM, and HLM Assays

In this protocol, the metabolic stability of compounds at 1 µM was determined in Mouse Liver Microsome (MLM), rat liver microsomes (RLM) or human liver microsomes (HLM). Each test compound was incubated in an aqueous reaction mixture (0.6 mL total volume) consisting of animal or human liver microsomal protein and NADPH (1.2 mM) in the presence of 100 mM potassium phosphate buffer (pH 7.4), and 3.3 mM $MgCl_2$. The final concentration of each substrate was 1 µM, and the microsomal protein concentration was 0.25 µM (concentration of substrate and microsome are subject to change according to individual case). After incubation at 37° C. for a specific time period (0, 5, 10, 20 and 30 min), the reaction was terminated by the addition of 200 µL ice cold acetonitrile containing internal standard (100 ng/mL) after 100 µL aliquots of reaction mixture was removed. The quenched reaction mixtures were centrifuged at 3200 rpm for 5 min, and 100 µL of the supernatant were transferred to 96-well deep plate. The samples in 96 well plate were analyzed by LC-MS/MS using an Applied Biosystems-Sciex model API 3000 mass spectrometer. The data were analyzed using the following equations.

Compound response=Analyte Area/IS Area

Relative concentration=$(T_{response}/T_{0\ response})*100\%$

Half life$(T_{1/2})$(min)=0.693/Kdep $V$(µL/mg)=volume of incubation(mL)/protein in the incubation(mg)

Clearance(CL)(µL/min/mg protein)=$V \times 0.693/T_{1/2}$

Human Plasma Protein Binding (hPPB) Assay

Human Plasma Protein Binding (hPPB) of test compounds was measured by rapid equilibrium dialysis device using the RED Device Inserts. In the reaction of 5 h, the drug concentration of the sample chamber and buffer chamber can be determined, through which we can calculated hPPB of test compounds. RED Device Inserts and Single-Use RED Base Plate were purchased from the Linden Bioscience, Woburn, Mass. (Taiwan, Thermo scientific). Human plasma was obtained from one healthy volunteer. Pooled human plasma from healthy individuals in this study was obtained from the Southern Medical University (China) and was stored frozen at −20° C. until use. SHZ-88A Reciprocating thermostatic oscillator was purchased from Taicang City Experimental Equipment Co. (China). Chlorpromazine (>99% in purity, positive control) and Phenacetin (>99% in purity, internal standard, IS) were all purchased from the Sigma Chemical Co. (China). Chlorpromazine HCl was used as a positive control. An aliquot (300 L) of plasma was accurately added into the sample chamber, and 6 µL compounds solution (500 µM, 50% DMSO) was added (n=3). An aliquot (500 µL) of Dulbecco solution was added into the buffer chamber. These solution were all oscillated for 5 hours (37° C., 90 rpm). Then, 50 µL solution in sample chamber was removed, 50 µL Dulbecco solution was added, and mixed. Also, 50 µL solution in buffer chamber was removed, 50 µL plasma was added, and mixed. 200 µL ACN (including internal Standard, 100 ng/mL) were added separately, oscillated, mixed, and centrifuged (20 min, 15000 g). An aliquot (50 µL) of the supernatant was accurately transferred to a clean 1.5 mL test tube and 100 µL $H_2O$ was added, mixed. 10 µL of mixture was separately injected into LC-MS system for determination of the drug concentration in the sample chamber and buffer chamber. The data were analyzed using the following equation: % hPPB=$[1-(Concentration_{buffer\ chamber}/Concentration_{plasma\ chamber})]*100\%$ (Barre, et al., 1985, which is incorporated herein by reference).

Rat Pharmacokinetic (PK) Analysis

Male SD rats, weighing 180-220 g (Southern China Medical University, China) were utilized for the studies. Animals were maintained on standard animal chow and water ad libitum, in a climate controlled room (23±1° C.), 30-70% relative humidity, a minimum of 10 exchanges of room air per hour and a 12-h light/dark cycle) for one week prior to experiments. The test compound was dissolved in suitable solvent. Pharmacokinetic properties were determined following i.v. and oral administration. Animals were randomly distributed into two experimental groups (n=4). The oral groups were given 5 mg/kg of the test compound by gastric gavage. The other group was dosed by injection into the tail vein (1 mg/kg). After single administration, whole blood samples (100-200 µL) were obtained from the orbital venous plexus at the following time points after dosing: 5, 10, 30 min and 1, 2, 3, 4, 6, 8, 11 and 24 h (p.o.); 2, 10, 30 min and 1, 2, 3, 4, 6, 8, 11 and 24 h (i.v.). Whole blood samples were collected in heparinized tubes. The plasma fraction was immediately separated by centrifugation (8,000 rpm, 6 min, 4° C.) and stored at −20° C. until LC-MS analysis. The rats were humanely euthanasia by carbon dioxide 24 hours after experiment without pain.

Plasma Sample Analysis. Standard Curve Sample Preparation:

The compound was dissolved in DMSO at a concentration of 2 mg/mL and diluted with 50% methanol solution to series concentration as follow: 20, 50, 100, 500, 1000, 2000, 4000, 6000, 12000, 40000 ng/mL. 10 µL series concentration solution and 50 µL blank plasma were added to 1.5 mL tube and vortex for 3 min, then 150 µL acetonitrile containing internal standard were added and vortex for 5 min, finally spin tube in centrifuge at 16000 g for 40 min at 4° C. Plasma sample preparation: The plasma samples were prepared using protein precipitation method. 10 µL 50% methanol water solution and 50 µL plasma samples were added to 1.5 mL tube and vortex for 3 min, then 150 µL acetonitrile containing internal standard were added and vortex for 5 min, finally spin tube in centrifuge at 16000 g for 40 min at 4° C. LC/MS/MS analysis: After centrifuge, 100 µL supernatant was transfer to the 96 well plate and analyzed by LC-MS/MS using an Applied Biosystems-Sciex model API 3000 mass spectrometer. The pharmacokinetics parameters were calculated by analyzing the compound concentration in plasma samples using the pharmacokinetic software DAS.2.0.

Protease Selectivity

Figure 2:
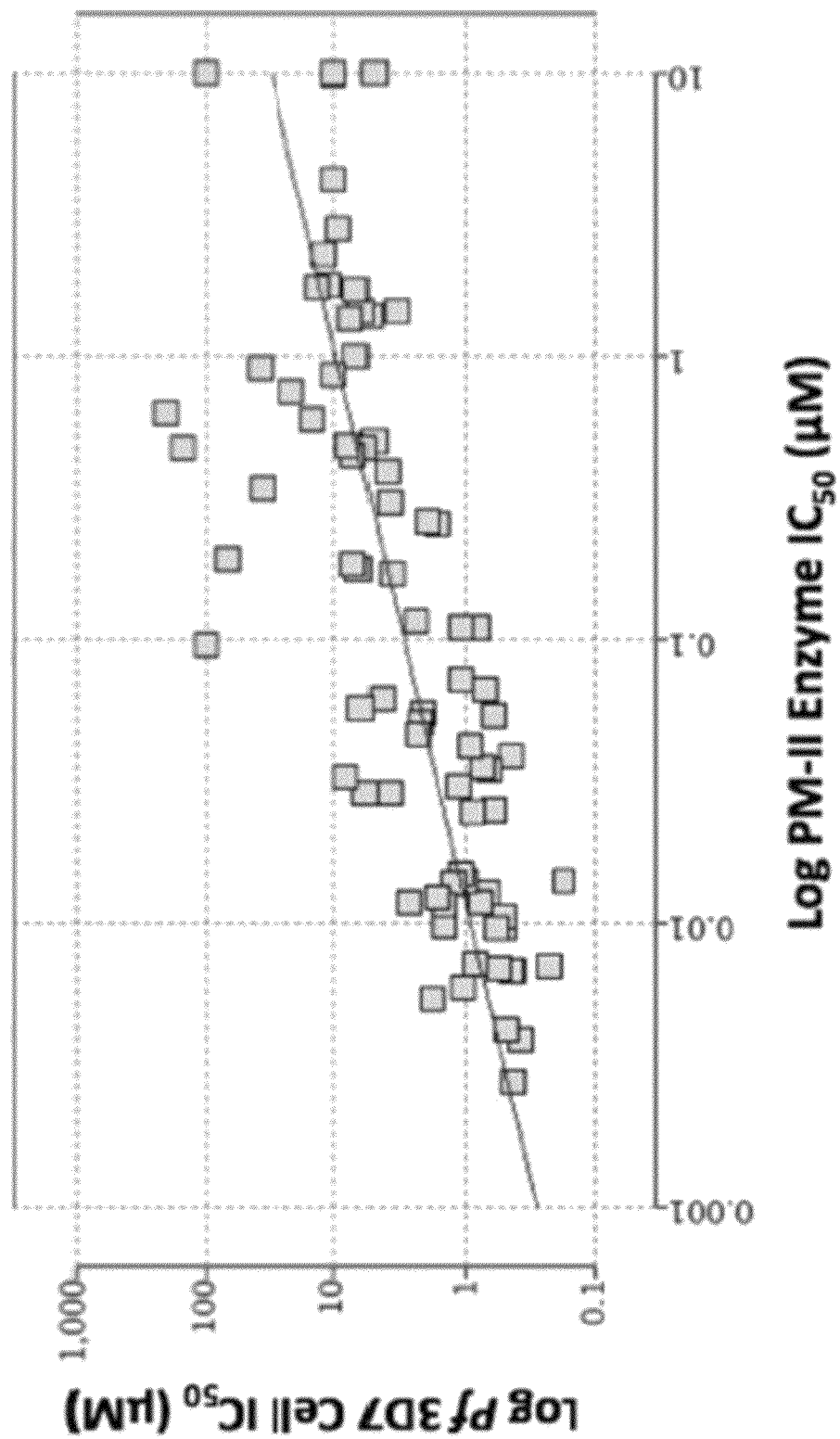
FIG. 2—General Correlation between PM-II Enzyme Activity and Antimalarial 3D7 Activity. This figure shows a graph plotting the $IC_{50}$ of the compound in PM-II versus the $IC_{50}$ of the compound in Pf3D7 cell

A subset of these antimalarial compounds were analyzed for inhibition of *Plasmodium* aspartic proteases PM-II and PM-IV. See Table 8. Most of the aminohydantoins evaluated are potent inhibitors of both PM-II and PM-IV, some in the single digit nanomolar range. Compounds with weaker 3D7 potency generally also had weaker PM-II and PM-IV activity. Approximately 80 analogs were assayed for PM-II activity and plotted this potency versus 3D7 potency (FIG. 2). While there is a loose correlation between PM-II potency and 3D7 potency, there is a 30-100 fold shift in potency. Without being bound by theory, these data suggest that the observed PM-II and PM-IV activity may be indicative of inhibition of one or more additional, albeit unidentified, *Plasmodium* aspartic proteases.

It is also evident that while these compounds are potent inhibitors of *Plasmodium* PM-II and PM-IV, they are poor inhibitors of human aspartic proteases BACE, CatD, and CatE (Table 8). Compound 117 is >1000-fold selective for PM-II over BACE and CatD and −300-fold over CatE. Compounds containing the S3-occupying aryl ring, such as 136, also retained greater than 1000-fold selectivity over BACE and CatD and −200-fold over CatE. Furthermore, a comparison compound with a methyl group in place of the cyclohexyl substituent in the $R^1$ position demonstrates the importance of the cyclohexyl group (or a secondary alkyl group) in enhancing antimalarial 3D7 and PMII potency while reducing potency against BACE. Compounds with larger but more flexible $R^1$ side chains generally were found to be less selective.

TABLE 8

Protease Selectivity Profile

| Compound | Pf 3D7 IC$_{50}$ | PM-II IC$_{50}$ | PM-IV IC$_{50}$ | BACE IC$_{50}$ | CatD IC$_{50}$ | CatE IC$_{50}$ |
|---|---|---|---|---|---|---|
| (structure 1) | 2.76 | 0.012 | 0.045 | 2.3 | 0.385 | 0.099 |
| (structure 2) | >10 | >10 | >10 | nd | nd | nd |

TABLE 8-continued

Protease Selectivity Profile

| Compound | Pf 3D7 IC$_{50}$ | PM-II IC$_{50}$ | PM-IV IC$_{50}$ | BACE IC$_{50}$ | CatD IC$_{50}$ | CatE IC$_{50}$ |
|---|---|---|---|---|---|---|
| [cyclohexyl bis-methoxyphenyl thiohydantoin structure] | >5 | >10 | nd | nd | nd | nd |
| 117 | 0.463 | 0.004 | 0.015 | 12.0 | >10 | 1.19 |
| 176 | 0.453 | 0.007 | 0.018 | ~10 | >10 | 0.511 |
| 207 | >5 | 0.505 | 0.192 | nd | nd | nd |
| 166 | 0.697 | 0.035 | 0.109 | nd | nd | nd |
| 206 | 0.383 | 0.002 | 0.010 | 6.01 | 0.52 | 0.233 |
| 275 | 0.463 | 0.017 | 0.059 | 2.07 | 0.934 | 0.841 |
| 128 | 0.768 | 0.036 | 0.041 | 28.9 | 1.10 | 1.86 |
| 171 | 0.595 | 0.007 | 0.007 | ~7.15 | ~14.9 | 4.01 |
| 136 | 0.75 | 0.013 | 0.031 | 1.68 | >10 | >10 |

Inhibition Profile and Selectivity

In order to evaluate this series for its potential as oral antimalarial agents, compound 117 and closely related compounds 176, 206, and 275 were further profiled through the studies outlined in Table 9. All four compounds retained nearly equivalent potency against 3D7 at 48 h and against the chloroquine- and pyrimethamine-resistant Dd2 strain, indicating the novel mechanism of action and the potential utility of this class of antimalarials in targeting drug resistant parasites.

The compounds were also profiled against a number of human enzymes and cell lines. The compounds were found to have limited activity in a HepG2 cytotoxicity assay and against most CYP enzymes evaluated, with the exception of CYP3A4. Compound 117 showed good metabolic stability in mouse, rat, and human liver microsomes (MLM, RLM, and HLM, respectively) and is orally bioavailable in rats with a half-life of 2.9 h.

TABLE 9

Profile of inhibition of selected inhibitors

| Assay | 117 | 176 | 206 | 275 |
|---|---|---|---|---|
| MW | 393 | 395 | 408 | 409 |
| cLogP | 4.0 | 2.1 | 4.3 | 2.6 |
| Pf 3D7 IC$_{50}$ (μM, 72 hr) | 0.463 | 0.459 | 0.383 | 0.463 |
| Pf Dd2 IC$_{50}$ (μM, 72 hr) | 0.480 | 0.526 | 0.367 | 0.442 |
| Pf 3D7 IC$_{50}$ (μM, 48 hr) | 0.751 | 0.404 | 0.339 | 0.571 |
| HepG2 IC$_{50}$ (μM) | 9.4 | >50 | 8.0 | 30 |
| CYP1A2 IC$_{50}$ (μM) | >10 | nd | nd | nd |
| CYP2C19 IC$_{50}$ (μM) | 5.48 | nd | nd | nd |
| CYP2D6 IC$_{50}$ (μM) | >10 | nd | nd | nd |
| CYP3A4 IC$_{50}$ (μM) | 0.449 | nd | nd | nd |
| MLM t$_{1/2}$ (min) | 81 | nd | 26 | nd |
| RLM t$_{1/2}$ (min) | 61 | 83 | 14 | 35 |
| HLM t$_{1/2}$ (min) | 29 | 36 | nd | nd |
| hPPB (%) | 98.5 | 78.1 | 99.7 | 88.7 |
| Rat PK t$_{1/2}$ (h) | 2.9 | 1.1 | 1.2 | nd |
| Rat PK oral bioavailability (% F) | 16 | 21 | nd | nd |

Lipophilicity and IC$_{50}$ of Inhibitors cLogP values were calculated using the JChem calculators from ChemAxon.

TABLE 10

Lipophilicity Data and IC$_{50}$ for Selected R$^1$ Modified Inhibitors

| Compound | Pf3D7 IC$_{50}$ (μM) | cLogP |
|---|---|---|
| [imidazolidinone structure with phenyl ethyl substituent] | 2.76 | 5.3 |
| 102 | 8.29 | 4.2 |
| 162 | 0.855 | 3.9 |
| 158 | 4.11 | 2.6 |
| 204 | 0.722 | 3.0 |
| 159 | 0.611 | 3.5 |
| 100 | 3.85 | 4.2 |
| 117 | 0.463 | 3.9 |
| 220 | 0.427 | 4.4 |
| 176 | 0.459 | 2.1 |
| 207 | >5.0 | 1.8 |
| 166 | 0.697 | 2.2 |
| 206 | 0.436 | 3.1 |
| 221 | 0.383 | 4.3 |
| 275 | 0.463 | 2.6 |

TABLE 11

Lipophilicity Data and IC$_{50}$ for Selected R$^2$ and R$^3$ Modified Inhibitors

| Compound | Pf 3D7 IC$_{50}$ (μM) | cLogP |
|---|---|---|
| 128 | 0.768 | 3.9 |
| 141 | 0.533 | 4.1 |
| 153 | 0.917 | 4.1 |
| 201 | 2.2 | 7.1 |
| 157 | 0.466 | 4.6 |
| 156 | 1.26 | 5.3 |
| 237 | 0.533 | 5.3 |
| 155 | 1.07 | 5.5 |
| 267 | 1.06 | 5.5 |
| 177 | 1.49 | 5.7 |
| 171 | 0.595 | 4.5 |
| 214 | 0.787 | 4.5 |
| 136 | 0.75 | 4.7 |
| 210 | 1.81 | 4.9 |
| 225 | 0.318 | 4.5 |
| 269 | 0.725 | 5.1 |
| 238 | 0.424 | 5.7 |
| 228 | 0.641 | 5.8 |

TABLE 12

Impact of Cyclic R$^1$ on Antimalarial 3D7 Potency and Aspartic Protease Selectivity.

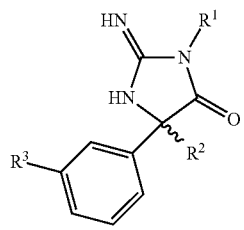

| Example | R$^1$ | R$^2$ | R$^3$ | 3D7 IC$_{50}$ (μM) | PM-2 IC$_{50}$ (μM) | BACE1 IC$_{50}$ (μM) | BACE1/PM2 Ratio |
|---|---|---|---|---|---|---|---|
| 135 | Me | Ph | 3-Pyr | 6.88 | 1.01 | 1.68 | 1.7 |
| 136 | cHex | Ph | 3-Pyr | 0.75 | 0.013 | 18.1 | 1392 |
| 327 | Me | Ph | 3-MeO—Ph | 4.97 | 0.240 | 0.392 | 1.6 |
| 326 | cHex | Ph | 3-MeO—Ph | 1.34 | 0.0331 | ~9 | ~270 |
| 324 | —(CH$_2$)$_2$O(CH$_2$)$_2$— | Ph | 3-MeO—Ph | 1.46 | 0.0113 | 2.46 | 218 |
| 330 | Me | cPr | 3-MeO—Ph | ~2.4 | 0.751 | 0.278 | 0.370 |
| 328 | cHex | cPr | 3-MeO—Ph |  | 0.104 | ~7 | 67 |
| 329 | —(CH$_2$)$_2$O(CH$_2$)$_2$— | cPr | 3-MeO—Ph | 0.746 | 0.0831 | ~4 | 48 |

TABLE 13

Biological Assay Results.

| Example | 3D7 IC$_{50}$ (μM) | Dd2 IC$_{50}$ (μM) | PM-2 IC$_{50}$ (μM) | BACE1 IC$_{50}$ (μM) |
|---|---|---|---|---|
| 100 | 3.85 |  | 0.0287 | >10 |
| 102 | 8.29 |  | 0.0331 |  |
| 105 | 6.31 |  | 0.0574 |  |
| 117 | 0.475 | 0.48 | 0.00396 | 12 |
| 128 | 0.768 |  | 0.0359 | 28.9 |
| 136 | 0.75 |  | 0.013 | 18.1 |
| 141 | 0.533 |  | 0.0106 |  |
| 142 | 10.8 |  | 1.79 |  |
| 153 | 0.917 |  | 0.0249 |  |
| 154 | 1.48 |  | 0.0099 |  |
| 155 | 1.07 |  | 0.006 |  |
| 156 | 1.26 |  | 0.014 |  |
| 157 | 0.466 |  | 0.00687 |  |
| 158 | 4.11 |  | 0.392 | >10 |
| 159 | 0.611 |  | 0.0251 |  |
| 162 | 0.855 |  | 0.0073 |  |
| 166 | 0.697 |  | 0.0347 |  |
| 167 | 9.32 |  | 2.83 |  |
| 168 | 1.09 |  | 0.11 |  |
| 171 | 0.595 |  | 0.00697 | ~7.15 |
| 172 | 0.533 |  | 0.00964 |  |
| 173 | 0.614 |  | 0.0547 |  |
| 176 | 0.459 | 0.526 | 0.00681 | ~10.1 |
| 177 | 1.49 |  | 0.0117 |  |
| 198 | >2.5 |  | 0.118 |  |
| 201 | 2.2 |  | 0.0551 |  |
| 202 | 0.349 |  | 6.75 |  |
| 203 | 1.13 |  | 0.0149 |  |
| 204 | 0.722 |  | 0.0674 |  |
| 206 | 0.436 |  | 0.00276 |  |
| 207 | >5.0 |  | 0.505 |  |
| 210 | 1.81 |  | 0.00547 |  |
| 211 | 1.03 |  | 0.0141 |  |
| 212 | 1.71 |  | 0.0123 |  |
| 214 | 0.787 |  | 0.012 |  |
| 219 | 0.582 |  | 0.00962 |  |
| 220 | 0.427 |  | 0.00237 |  |
| 221 | 0.207 | 0.367 | 0.00239 | 6.01 |
| 223 | 0.644 |  |  |  |
| 225 | 0.318 |  |  |  |
| 227 | 0.657 |  |  |  |
| 228 | 0.641 |  | 0.00289 |  |
| 229 | 0.682 |  |  |  |
| 230 | 0.828 |  |  |  |
| 231 | 0.795 |  |  |  |
| 232 | 1.27 |  |  |  |
| 233 | 0.554 |  |  |  |
| 234 | 0.894 |  |  |  |
| 235 | 0.684 |  |  |  |
| 236 | 0.708 |  |  |  |

TABLE 13-continued

Biological Assay Results.

| Example | 3D7 IC$_{50}$ (μM) | Dd2 IC$_{50}$ (μM) | PM-2 IC$_{50}$ (μM) | BACE1 IC$_{50}$ (μM) |
|---|---|---|---|---|
| 237 | 0.533 | | | |
| 238 | 0.424 | | 0.0022 | |
| 248 | 0.294 | | 0.028 | |
| 249 | 1.52 | | | |
| 250 | 2.74 | | | |
| 252 | 0.266 | | 0.00528 | |
| 253 | 0.381 | | | |
| 267 | 1.06 | | | |
| 269 | 0.725 | | | |
| 270 | 0.724 | | | |
| 272 | 0.976 | | | |
| 273 | 1.38 | | | |
| 274 | 0.633 | | 0.0114 | |
| 275 | 0.521 | 0.442 | 0.0169 | 2.07 |
| 276 | 0.336 | | 0.002 | 7.85 |
| 277 | 1.57 | | 0.00439 | |
| 278 | 1.04 | | 0.00276 | |
| 302 | 1.07 | | 0.0488 | >10 |
| 303 | 1.01 | | 0.0031 | |
| 304 | 1.34 | | 0.00188 | |
| 305 | 81% inh @ 1 μM | | 0.0093 | 6.7 |
| 306 | 5.23 | | | |
| 307 | 5.56 | | | |
| 308 | 0.677 | | 0.0754 | >10 |
| 310 | 72% inh @ 1 μM | | 0.00584 | ~2.6 |
| 311 | 81% inh @ 1 μM | | 0.002 | ~6.8 |
| 313 | 27% inh @ 1 μM | | 0.011 | ~2.2 |
| 322 | 34% inh @ 1 μM | | 0.0202 | >10 |
| 323 | 31% inh @ 1 μM | | 0.0743 | ~10 |
| 324 | 1.46 | | 0.0113 | 2.46 |
| 325 | 0.752 | | 0.426 | >10 |
| 326 | 1.34 | | 0.0331 | ~8.9 |
| 328 | 0.746 | | 0.104 | ~6.8 |
| 329 | 0.621 | | 0.0831 | ~3.6 |
| 331 | 0.354 | | 0.0581 | ~10 |
| 332 | 25% inh @ 1 μM | | 0.216 | >10 |
| 333 | 9% inh @ 1 μM | | 0.639 | >10 |
| 334 | 14% inh @ 1 μM | | 0.0859 | >10 |
| 335 | 0.377 | | 0.0907 | >10 |
| 336 | 70% inh @ 1 μM | | 0.395 | >10 |
| 389 | >5.0 | | | |
| 390 | 4.08 | | | |
| 404 | 7% inh @ 1 μM | | | |
| 412 | 4.21 | | | |
| 413 | 1.99 | | | |
| 414 | 0.293 | | | |
| 447 | 0.494 | | 0.0674 | 17.3 |
| 486 | 1.46 | | | |
| 487 | 0.248 | | 0.512 | 8.65 |
| 488 | 0.362 | | 0.443 | 2.98 |
| 489 | 0.268 | | 0.211 | 1.16 |
| 490 | 0.515 | | | |
| 491 | 0.47 | | 0.0517 | 8.32 |
| 492 | 1.11 | | | |
| 493 | 0.64 | | | |
| 494 | 0.68 | | | |
| 495 | 0.93 | | | |
| 496 | 0.35 | | | |
| 497 | 1.15 | | | |
| 498 | 1.29 | | | |
| 499 | 1.39 | | | |
| 500 | 2.36 | | | |
| 501 | 1.54 | | | |
| 512 | 0.38 | | 0.126 | 16.8 |
| 513 | 0.40 | | 0.219 | 6.64 |
| 514 | 0.97 | | | |
| 515 | 0.81 | | | |
| 516 | 0.28 | | | |
| 517 | 0.35 | | 0.125 | 14.7 |
| 518 | 5.32 | | | |
| 519 | 5.65 | | | |
| 547 | 0.85 | | | |
| 548 | | | | |
| 549 | 1.33 | | | |
| 550 | 2.48 | | | |
| 551 | 0.78 | | | |
| 563 | | | | |
| 564 | | | | |
| 565 | | | | |
| 566 | | | | |
| 567 | | | | |
| 568 | | | | |
| 569 | 0.45 | | | |
| 570 | 2.87 | | | |
| 571 | 0.4 | | | |
| 572 | | | | |
| 573 | >20 | | | |
| 574 | 0.27 | | | |
| 575 | 1.09 | | | |
| 577 | 1.67 | | | |

In vivo Antimalarial Efficacy Suppressive Assay

In vivo antimalarial activity was determined for compounds against the rodent *Plasmodium* chabaudi ASS and ASCQ strains according to the 4-day suppressive test (Peters, 1975, which is incorporated herein by reference). Briefly, NIH mice (n=8 per group) were inoculated i.p. with 2×10$^7$ parasitized (*Plasmodium* chabaudi ASS or ASCQ) red blood cells. Thereafter, the compounds were administered orally to the animals once daily at 4 h, 24 h, 48 h and 72 h post inoculation. Groups (n=6) including a vehicle control and chloroquine (CQ) as a reference drug were included. Parasitemia levels were determined on the day following the last treatment (Day 4). Results for 117 are shown in FIG. 1 and Table 14 contains results for compounds 117, 176, 206, and 275.

TABLE 14

Oral in vivo Efficacy of Inhibitors

| Compound | dose (mpk)[b] | % Inhibition of parasitemia[c] | Plasma [compound][d] (ng/mL) | | |
|---|---|---|---|---|---|
| | | | 1 hr | 6 hr | 24 hr |
| CQ | 4.5 | 99.99 | nd[a] | nd | nd |
| 117 | 100 | 89 | 2790 | 3393 | 575 |
| 176 | 110 | 63 | 4140[e] | nd | 29 |
| 206 | 100 | 73 | 2517 | 2187 | 7 |
| 275 | 100 | 41 | 10363 | 3027 | 123 |

[a]nd = not determined.
[b]Four hours after infection, compounds were dosed orally once daily for four days.
[c]Determined on Day 4 postinoculation.
[d]Compound concentration in the plasma determined 1, 6, and 24 h post last dose on Day 3.
[e]Determined at 30 minu post dose.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IV. References

The following references, to the extent that they provide exemplary procedural or other details supplementary to those set forth herein, are specifically incorporated herein by reference:

U.S. Pat. No. 2,798,053
U.S. Pat. No. 3,755,560
U.S. Pat. No. 4,418,534
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,567,430
U.S. Pat. No. 5,698,210
U.S. Pat. No. 5,824,328
U.S. Pat. No. 5,846,553
U.S. Pat. No. 5,858,384
U.S. Pat. No. 5,858,386
U.S. Pat. No. 5,885,605
U.S. Pat. No. 5,902,596
U.S. Pat. No. 5,983,390
U.S. Pat. No. 6,001,382
U.S. Pat. No. 6,335,027
U.S. Pat. No. 6,337,078
U.S. Pat. No. 6,346,262
U.S. Pat. No. 6,350,461
U.S. Pat. No. 6,387,386
U.S. Pat. No. 6,391,328
U.S. Pat. No. 7,090,147
U.S. Pat. No. 7,306,167
U.S. Patent Publn. 2006/0260183
U.S. Patent Publn. 2007/0160637
Acree et al., *Science*, 161:1346-1347, 1968.
Antonny et al., *J. Biol. Chem.*, 268:2393-2402, 1993.
Baumann et al., *Embo. J.*, 13:5040-5050, 1994.
Benton et al., *Cell*, 136:149-162, 2009.
Benton et al., *PLoS Biol.*, 4:e20, 2006.
Bernier et al., *Anal. Chem.*, 71:1-7, 1999.
Boekhoff et al., *J. Comparative Physiol. B*, 160:99-103, 1990.
Bohbot et al., *Insect. Mol. Biol.*, 16:525-537, 2007.
Brady et al., *Ann. Trop. Med. Parasitol.*, 91:S121-122, 1997.
Breer et al., *Nature*, 345:65-68, 1990.
Calderon et al., *ACS Med. Chem. Lett.*, 2:741-46, 2011.
Carnevale et al., *Bull. World Health Organ.*, 56:147-154, 1978.
Clyne et al., *Neuron.*, 22:327-338, 1999.
Clyne et al., *Science*, 287:1830-1834, 2000.
Cork and Park, *Med. Vet. Entomol.*, 10:269-276, 1996.
CTFA Cosmetic Ingredient Handbook, Vol. 3, p. 3187-3192
Curtis, Parasitology Today, 11:316-318, 1986.
De Jong and Knols, *Acta Trop.*, 59:333-335, 1995.
De Jong and Knols, *Experientia*, 51:80-84, 1995.
Dekker et al., *J. Med. Entomol.*, 38:868-871, 2001a.
Dekker et al., *Physiol. Entomol.*, 26:124-134, 2001b.
Dobritsa et al., *Neuron.*, 37:827-841, 2003.
Eiras and Jepson, *Bull. Entomol. Res.*, 81:151-160, 1991.
Elmore and Smith, *Insect Biochem. Mol. Biol.*, 31:791-798, 2001.
Engsontia et al., *Insect Biochem. Mol. Biol.*, 38:387-397, 2008.
Fox et al., *Proc. Natl. Acad. Sci. USA*, 98:14693-14697, 2001.
Gao and Chess, *Genomics*, 60:31-39, 1999.
Gilles, *Bull. Entomol. Res.*, 70:525-532, 1980.
Goldman et al., *Neuron.*, 45:661-666, 2005.
Hallem and Carlson, *Cell*, 125:143-160, 2006.
Hallem et al., *Cell*, 117:965-979, 2004a.
Hallem et al., *Nature*, 427:212-213, 2004b.
Hildebrand and Shepherd, *Annu. Rev. Neurosci.*, 20:595-631, 1997.
Hill et al., *Science*, 298:176-178, 2002.
Holt et al., *Science*, 298:129-149, 2002.
Jones et al., *Curr. Biol.*, 15:R119-R121, 2005.
Jones et al., *Nature*, 445:86-90, 2007.
Kellogg, *J. Insect. Physiol.*, 16:99-108, 1970.
Kim et al., *Bioinformatics*, 16:767-775, 2000.
Krieger and Breer, *Science*, 286:720-723, 1999.
Krieger et al., *Eur. J. Neurosci.*, 16:619-628, 2002.
Krieger et al., *Insect. Biochem. Mol. Biol.*, 29:255-267, 1999.
Krieger et al., *J. Comp. Physiol. A Neuroethol. Sens. Neural. Behav. Physiol.*, 189:519-526, 2003.
Krotoszynski et al., *J. Chromotographic Sci.*, 15:239-244, 1977.
Kwon et al., *Proc. Natl. Acad. Sci. USA*, 104:3574-3578, 2007.
Labows Jr., *Perfumer & Flavorist*, 4:12-17, 1979.
Larsson et al., *Neuron.*, 43:703-714, 2004.
Laue et al., *Cell Tissue Res.*, 288:149-158, 1997.
Lindsay et al., *J. Med. Entomol.*, 30:308-373, 1993.
Lu et al., *Curr. Biol.*, 17:1533-1544, 2007.
Liu et al., *PLoS Biology* 8(8): e1000467, 2010.
Lundin et al., *FEBS Lett.*, 581(29):5601-5604, 2007.
Mboera and Takken, *Rev. Med. Vet. Entomol.*, 85:355-368, 1997.
McCutcheon's, Detergents and Emulsifiers, North American Edition, 1986.
Meijerink and van Loon, *J. Insect Physiol.*, 45:365-373, 1999.
Meijerink et al., *J. Insect Physiol.*, 47:455-464, 2001.
Merrill et al., *Insect Molecul. Biol.*, 12:641-650, 2003.
Merrill et al., *J. Neurobiol.*, 63:15-28, 2005.
Merrill et al., *Proc. Natl. Acad. Sci. USA*, 99:1633-1638, 2002.
Mombaerts, *Annu. Rev. Neurosci.*, 22:487-509, 1999.
Muirhead-Thomson, *Brit. Med. J., I*:1114-1117, 1951.
Pelosi and Maida, *Comp. Biochem. Physiol. B Biochem. Mol. Biol.*, 111:503-514, 1995.
Pitts et al., *Proc. Natl. Acad. Sci. USA*, 101:5058-5063, 2004.
Qiu et al., *Chem. Senses*, 31:845-863, 2006b.
Qiu et al., *Med. Vet. Entomol.*, 20:280-287, 2006a.
*Remington's Pharmaceutical Sciences*, 18th Ed. Mack Printing Company, 1289-1329, 1990.
Robertson and Wanner, *Genome Res.*, 16:1395-1403, 2006.
Robertson et al., *Proc. Natl. Acad. Sci. USA*, 100(2):14537-14542, 2003.
Rutzler et al., *J. Comp. Neurol.*, 499:533-545, 2006.
Sato et al., *Nature*, 452(7190):1002-1006, 2008.
Schreck et al., *J. Am. Mosq. Control Assoc.*, 6:406-410, 1990.
Scott et al., *Cell*, 104:661-673, 2001.
Smilkstein, et al., *Antimicrob. Agents Chemother.*, 48:1803-1806, 2004.
Smith, *Neuron.*, 22:203-204, 1999.
Stengl, *J. Comp. Physiol. [A]*, 174:187-194, 1994.

Storkuhl and Kettler, *Proc. Natl. Acad. Sci. USA*, 98:9381-9385, 2001.
Suh et al., *Curr. Biol.*, 17:905-908, 2007.
Takken and Knols, *Annu. Rev. Entomol.*, 44:131-157, 1999.
Takken et al., *J. Insect Behavior*, 10:395-407, 1997.
Takken, *Insect Sci. Applns.*, 12:287-295, 1991.
Thomas, *Brit. Med. J.*, 2:1402, 1951.
Vosshall et al., *Cell*, 102:147-159, 2000.
Vosshall et al., *Cell*, 96:725-736, 1999.
Vosshall, *Chem. Senses*, 26:207-213, 2001.
Wetzel et al., *Proc. Natl. Acad. Sci. USA*, 98:9377-9380, 2001.
Wicher et al., *Nature*, 452(7190):1007-1011, 2008.
Winter, et al., *Exp. Parasitol.*, 114:47-56, 2006.
Wistrand et al., *Protein Sci.*, 15:509-521, 2006.
Xia et al., *Proc. Natl. Acad. Sci. USA*, 105:6433-6438, 2008.
Zwiebel and Takken, *Insect Biochem. Molec. Biol.*, 34:645-652, 2004.

What is claimed is:

1. A compound of Formula I:

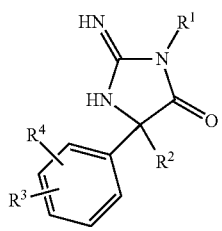

Formula I wherein:
$R^1$ is heterocycloalkyl$_{(C3-7)}$ or substituted heterocycloalkyl$_{(C3-7)}$;
$R^2$ is aryl$_{(C6-10)}$, -arenediyl$_{(C6-10)}$-alkoxy$_{(C1-7)}$, -arenediyl$_{(C6-10)}$-heteroaryl$_{(C1-5)}$, or a substituted version of any of these groups;
$R^3$ is:
hydroxy, halo, —C(O)NH$_2$, —C(O)NHCH$_3$, —C(O)N(CH$_3$)$_2$, or —CN; or
alkyl$_{(C1-7)}$, haloalkyl$_{(C1-7)}$, alkoxy$_{(C1-7)}$, haloalkoxy$_{(C1-7)}$, aryl$_{(C6-10)}$, —O-aryl$_{(C6-10)}$, heteroaryl$_{(C1-9)}$, —O-heteroaryl$_{(C1-9)}$, —O—CH$_2$-aryl$_{(C6-10)}$, -arenediyl$_{(C6-C10)}$-alkynyl$_{(C2-6)}$, substituted -arenediyl$_{(C6-C10)}$-alkynyl$_{(C2-6)}$, -heteroarenediyl$_{(C6-C10)}$-alkynyl$_{(C2-6)}$, substituted -heteroarenediyl$_{(C6-C10)}$-alkynyl$_{(C2-6)}$, —O—CH$_2$-heteroaryl$_{(C1-9)}$, substituted aryl$_{(C6-10)}$, substituted —O-aryl$_{(C6-10)}$, substituted heteroaryl$_{(C1-9)}$, substituted —O-heteroaryl$_{(C1-9)}$, substituted —O—CH$_2$-aryl$_{(C6-10)}$, or substituted —O—CH$_2$-heteroaryl$_{(C1-9)}$; and
$R^4$ is:
H, halo, hydroxy, or —CN; or
alkyl$_{(C1-7)}$, haloalkyl$_{(C1-7)}$, alkoxy$_{(C1-7)}$, or haloalkoxy$_{(C1-7)}$;
provided that when $R^2$ is cyclopropyl, $R^3$ is not 3-chlorophenyl;
or a pharmaceutically acceptable salt thereof.

2. The compound of claim 1, wherein $R^1$ is tetrahydropyranyl, piperidin-4-yl, 1-methylpiperidin-4-yl, N-Boc-piperidin-4-yl, 1-benzylpiperidin-4-yl, 1-acetylpiperidin-4-yl, 1-benzoylpiperidin-4-yl, or 1-[3-(dimethylamino)propanoyl]piperidin-4-yl.

3. The compound of claim 1, wherein $R^3$ is alkoxy$_{(C1-7)}$.

4. The compound of claim 3, wherein $R^3$ is methoxy, ethoxy or 2-methylpropoxy.

5. A compound of Formula III:

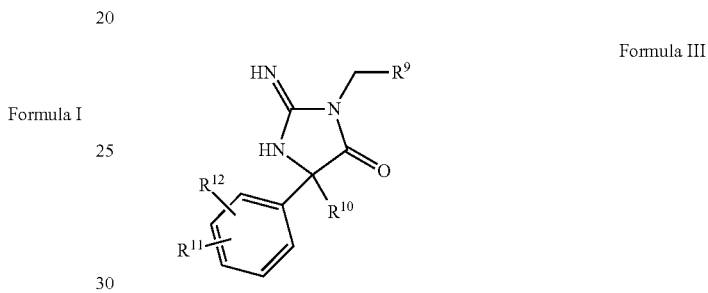

Formula III wherein:
$R^9$ is t-butyl, adamantanyl, aryl$_{(C6-10)}$, heteroaryl$_{(C1-6)}$ or substituted versions of any of these groups;
$R^{10}$ is 3-methoxyphenyl or 4-methoxyphenyl;
$R^{11}$ is:
hydroxy, methoxy, methyl, trifluoromethyl, trifluoromethoxy, halo, or —CN; or
aryl$_{(C6-10)}$, heteroaryl$_{(C1-9)}$, substituted aryl$_{(C6-10)}$, or substituted heteroaryl$_{(C1-9)}$; and
$R^{12}$ is H, halo, hydroxy, or —CN;
or a pharmaceutically acceptable salt thereof.

6. The compound of claim 5, wherein $R^9$ is pyridyl or picolinyl.

7. The compound of claim 5, wherein $R^{11}$ is 4-methoxy or 3-methoxy.

8. A compound further defined as:
3-cyclohexyl-2-imino-5,5-bis(4-methoxyphenyl)imidazolidin-4-one;
or a pharmaceutically acceptable salt thereof.

* * * * *